United States Patent
Dally et al.

(10) Patent No.: US 11,028,074 B2
(45) Date of Patent: Jun. 8, 2021

(54) CD73 INHIBITORS

(71) Applicant: Eli Lilly and Company, Indianapolis, IN (US)

(72) Inventors: Robert Dean Dally, Carmel, IN (US); Maria Cristina Garcia Paredes, Indianapolis, IN (US); Lawrence Joseph Heinz, II, Pittsboro, IN (US); Jennifer Marie Howell, Indianapolis, IN (US); Frank George Njoroge, Carmel, IN (US); Yan Wang, Carmel, IN (US); Genshi Zhao, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 16/481,146

(22) PCT Filed: Feb. 22, 2019

(86) PCT No.: PCT/US2019/019074
§ 371 (c)(1),
(2) Date: Jul. 26, 2019

(87) PCT Pub. No.: WO2019/168744
PCT Pub. Date: Sep. 6, 2019

(65) Prior Publication Data
US 2021/0002257 A1    Jan. 7, 2021

Related U.S. Application Data

(60) Provisional application No. 62/636,978, filed on Mar. 1, 2018, provisional application No. 62/775,553, filed on Dec. 5, 2018.

(51) Int. Cl.
*C07D 403/04* (2006.01)
*A61P 35/00* (2006.01)

(52) U.S. Cl.
CPC ............ *C07D 403/04* (2013.01); *A61P 35/00* (2018.01)

(58) Field of Classification Search
CPC ................................ C07D 403/04; A61P 35/00
See application file for complete search history.

(56) References Cited

U.S. PATENT DOCUMENTS 7,727,988 B2    6/2010    Bertani et al.

FOREIGN PATENT DOCUMENTS

| WO | 2007/135195 A1 | 11/2007 | |
|---|---|---|---|
| WO | 2017/120508 A1 | 7/2017 | |
| WO | WO 2017/120508 * | 7/2017 | ............ A61K 31/70 |
| WO | 2017/153952 A1 | 9/2017 | |

OTHER PUBLICATIONS

International Search Report of the International Searching Authority pertaining to International Application No. PCT/US2019/019074; dated May 13, 2019.
Written Opinion of the International Searching Authority pertaining to International Application No. PCT/US2019/019074; dated May 13, 2019.
Gong, Y. P., et al., "Evaluation of WO2017098421: GSK's benzothiazine compounds as CD73 inhibitor filings," *Expert opinion on therapeutic patents*, 28(2): 167-171 (Nov. 17, 2017).
Rahimova, R., et al., (2018). "Identification of allosteric inhibitors of the ecto-5'-nucleotidase (CD73) targeting the dimer interface. *PLoS computational biology*, 14(1), e1005943," DOI: 10.1371/journal.pcbi.1005943 (Jan. 29, 2018).
Allard D, et al., "CD73-adenosine: a next-generation target in immune-oncology," *Immunotherapy* 8: 145-163 (2016).
Antonioli L, et al., "Switching off CD73: a way to boost the activity of conventional and targeted antineoplastic therapies," *Drug Discovery Today* 22: 1686-1696 (Nov. 2017).
Antonioli L, et al., "Anti-CD73 immunotherapy: a viable way to reprogram the tumor microenvironment," *Oncoimmunology* 5(9): e1216292, doi: 10.1080/2162402X.2016.1216292, 3 pages (2016).
Antonioli L, et al., "Anti-CD73 in Cancer Immunotherapy: Awakening New Opportunities," *Trends in Cancer* 2: 95-109 (2016).
Beavis PA, et al., "CD73: a potent suppressor of antitumor immune responses," *Trends Immunol.* 33: 231-7 (2012).
Beavis, PA, et al., "Adenosine Receptor 2A Blockade Increases the Efficacy of Anti-PD-1 through Enhanced Antitumor T-cell Responses," *Cancer Immunol Res.* 3: 506-17 (2015).
Hay CM, et al., "Targeting CD73 in the tumor microenvironment with MEDI9447," *Oncoimmunology* 5(8): e1208875, doi: 10.1080/2162402X.2016.1208875 (2016).
Inoue Y, et al., "Prognostic impact of CD73 and A2A adenosine receptor expression in non-small-cell lung cancer," *Oncotarget* 2017; 8: 8738-8751 (Jan. 31, 2017).
Jin D, et al., "CD73 on Tumor Cells Impairs Antitumor T-Cell Responses: A Novel Mechanism of Tumor-Induced Immune Suppression," *Cancer Res.* 70: 2245-2255 (2010).
Loi S, et al., "CD73 promotes anthracycline resistance and poor prognosis in triple negative breast cancer," *Proc. Natl. Acad. Sci. USA* 110: 11091-11096 (2013).
Stagg J, et al., "CD73-Deficient Mice Have Increased Antitumor Immunity and Are Resistant to Experimental Metastasis," *Cancer Research* 71: 2892-2900 (2011).

(Continued)

*Primary Examiner* — Erich A Leeser
(74) *Attorney, Agent, or Firm* — Michael R. Asam

(57) ABSTRACT

The present invention provides 5-[5]-[2-cycloalkyl]-6-pyridazin-3-yl]-1H-pyrimidine-2,4-dione compounds, or pharmaceutically acceptable salts thereof, that inhibit the activity of CD73 and are useful in treating cancer.

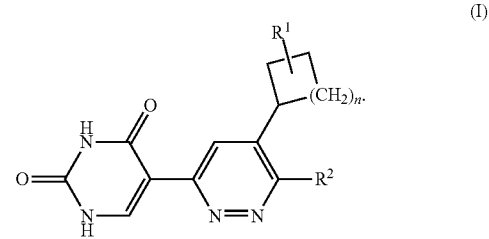

22 Claims, No Drawings

(56) References Cited

OTHER PUBLICATIONS

Zhang B, "CD73: A novel target for cancer immunotherapy," *Cancer Research* 70: 6407-6411 (2010).
Billingsley, Kelvin L., Kevin W. Anderson, and Stephen L. Buchwald. "A Highly Active Catalyst for Suzuki—Miyaura Cross-Coupling Reactions of Heteroaryl Compounds." Angewandte Chemie 118.21 (2006): 3564-3568.
Duncton, Matthew Aj, and Rajinder Singh. "Synthesis of trans-2-(Trifluoromethyl) cyclopropanes via Suzuki reactions with an Nmethyliminodiacetic acid boronate." Organic letters 15.17 (2013): 4284-4287.
Goudgaon, Naganna M., Geraldine Fulcrand El-Kattan, and Raymond F. Schinazi. "Boron containing pyrimidines, nucleosides, and oligonucleotides for neutron capture therapy." Nucleosides, Nucleotides & Nucleic Acids 13.1-3 (1994): 849-880.
Soderquist, John A., Ramon Huertas, and Gisela LeonColon. "Aryl and vinyl cyclopropanes through the in situ generation of B-cyclopropy19-BBN and its Suzuki—Miyaura coupling." Tetrahedron Letters 41.22 (2000): 4251-4255.
Wan, Zehong, Adrian Hall, Yun Jin, Jia-Ning Xiang, Eric Yang, Andrew Eatherton, Beverley Smith et al. "Pyridazine-derived y-secretase modulators." Bioorganic & medicinal chemistry letters 21, No. 13 (2011): 4016-4019.

\* cited by examiner

CD73 INHIBITORS

The present invention relates to 5-[5]-[2-cycloalkyl]-6-pyridazin-3-yl]-1H-pyrimidine-2,4-dione compounds, or pharmaceutically acceptable salts thereof, and pharmaceutical compositions comprising the compounds, that inhibit the activity of CD73 and are useful for treating cancer.

CD73, also known as 5'-nucleotidase or ecto-5'nucleotidase (EC 3.1.3.5), is an enzyme that converts 5' mononucleotides to nucleosides. CD73 is expressed in many tissues, and is upregulated in cancerous tissues, and the CD73 pathway promotes tumor growth by limiting antitumor T cell immunity via adenosine receptor signaling (Zhang B, *Cancer Research* 2010; 70: 6407-6411; Antonioli L, et al., *Drug Discovery Today* 2017; 22: 1686-1696).

CD73-deficient mice have increased antitumor immunity, and are resistant to experimental metastasis (Stagg J, et al., *Cancer Research* 2011; 71: 2892-2900). Extracellular adenosine generated by tumor CD73 accumulates in the tumor microenvironment, impairs antitumor T cell immunity (Zhang B, *Cancer Research* 2010; 70: 6407-6411; Antonioli L, et al., *Drug Discovery Today* 2017; 22: 1686-1696), and is linked to immune escape by tumors, proliferation, migration, neovascularization, metastasis and chemoresistance of tumor cells (Inoue Y, et al., *Oncotarget* 2017; 8: 8738-8751).

Elevated CD73 expression has also been reported to be associated with increased immune suppression (Jin D, et al., *Cancer Res.* 70: 2245-2255 (2010); Beavis P A, et al., *Trends Immunol* 33: 231-7 (2012); Beavis, P A, et al., *Cancer Immunol Res.* 3: 506-17 (2015); Loi S, et al., *Proc. Natl. Acad. Sci. USA* 110: 11091-11096 (2013)). Thus, the CD73 pathway exerts an immune-suppressive effect, and it has been suggested that blocking the CD73 pathway can be useful in treating cancer (Antonioli L, et al., *Oncoimmunol.* 2016; 5: e1216292, doi: 10.1080/2162402X.2016.1216292; Antonioli L, et al., *Trends in Cancer* 2016; 2: 95-109; Allard D, et al., *Immunotherapy* 2016; 8: 145-163). CD73 inhibitors are in clinical trials for the treatment of cancer (Hay C M, et al., *Oncoimmunol.* 2016; 5(8): e1208875; Allard D, et al., *Immunotherapy* 2016; 8: 145-163).

There remains a need to provide alternative CD73 inhibitors, more particularly, for the treatment of cancer. In particular, there remains a need for orally available small molecule CD73 inhibitors, and which exhibit more complete target inhibition in the tumor microenvironment.

Accordingly, the present invention provides CD73 inhibitor compounds which may be useful for treating cancer. The present invention provides the compound of Formula I:

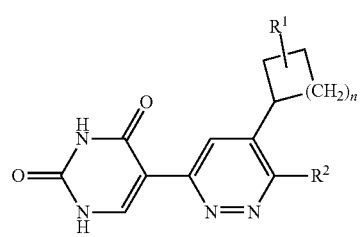

wherein n is 0-3;
wherein $R^1$ is —H, —F, -gem-difluoro, -gem-dimethyl, —$C_{1-4}$ alkyl, —$CHF_2$, —$CHF_2CH_3$ or —$CH_2CH_2F$; and
$R^2$ is selected from —H, —$CH_3$, —F, —Cl, —CN, or —$OCH_3$;
or a pharmaceutically acceptable salt thereof.

In another embodiment, the present invention provides the compound of Formula I, wherein n is 0, $R^1$ is —$C_{1-4}$ alkyl, and $R^2$ is —$CH_3$, or a pharmaceutically acceptable salt thereof.

In another embodiment, the compound is

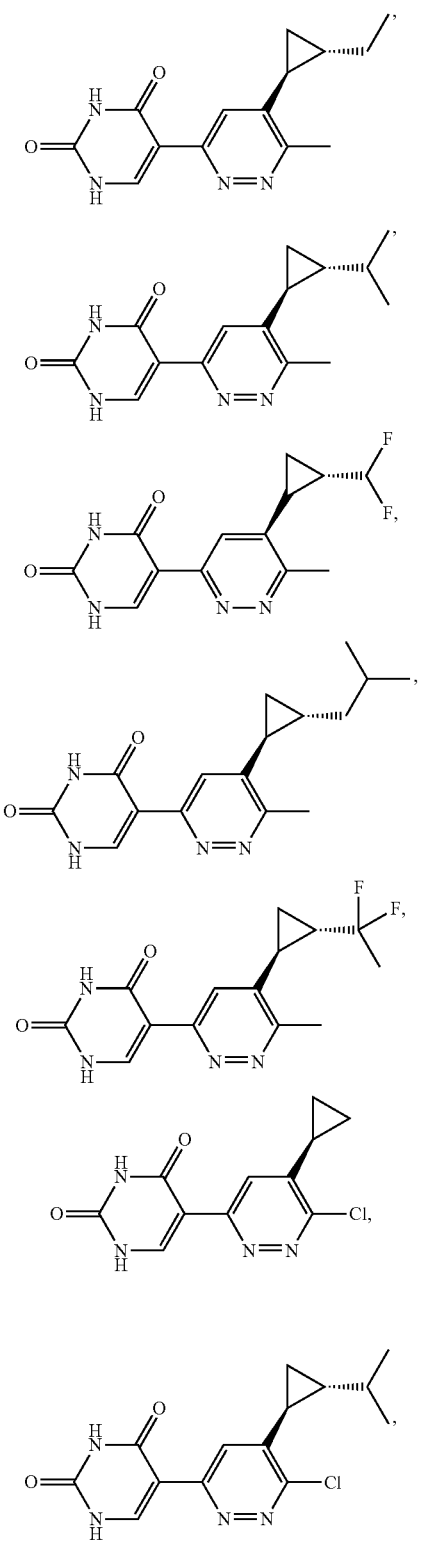

-continued
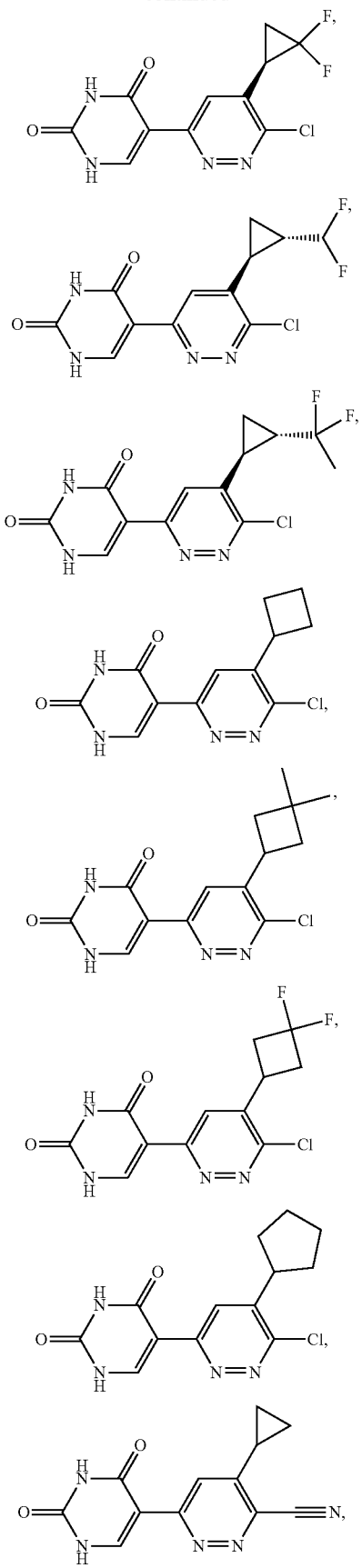
-continued
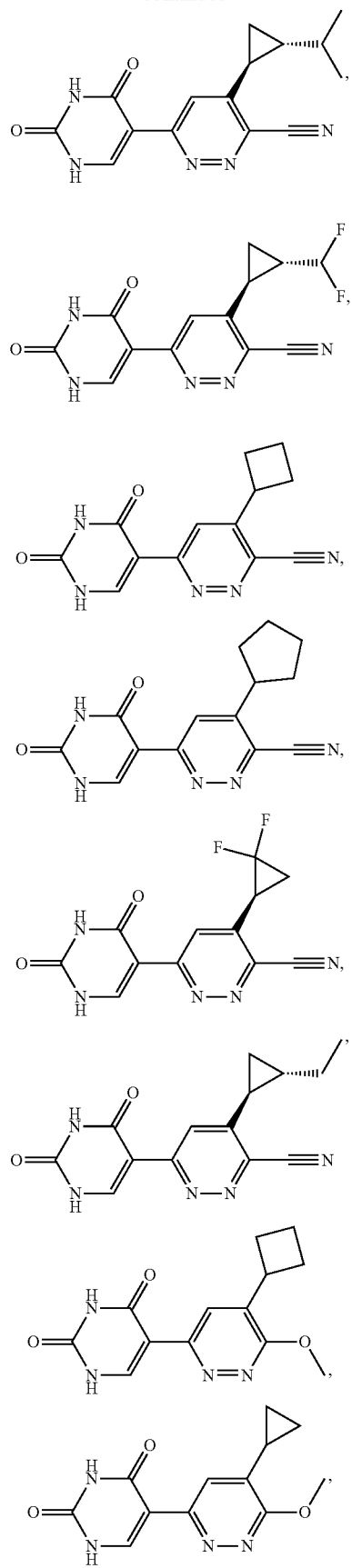

-continued
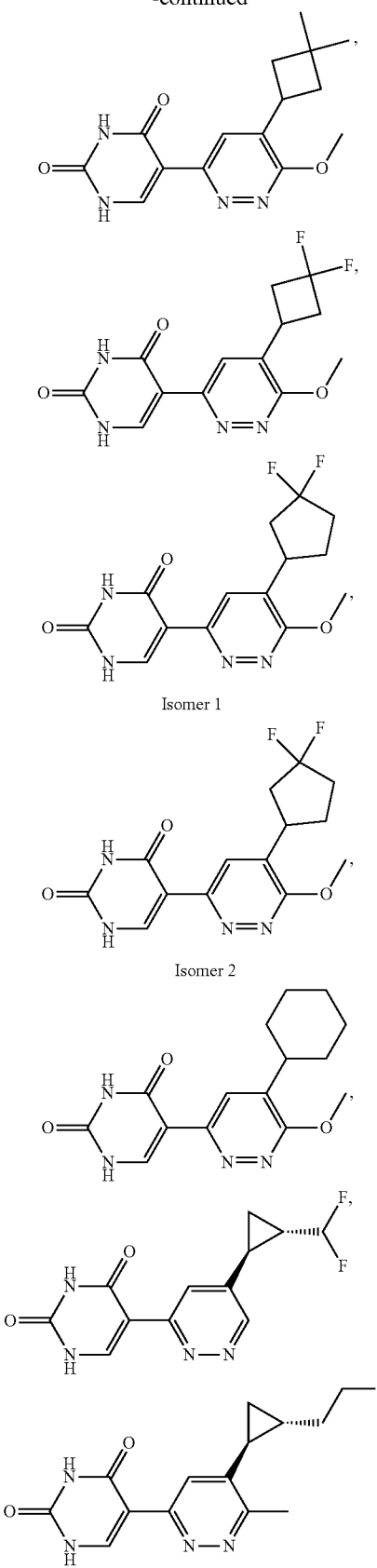
Isomer 1
Isomer 2
or a pharmaceutically acceptable salt thereof.
In another embodiment, the compound is
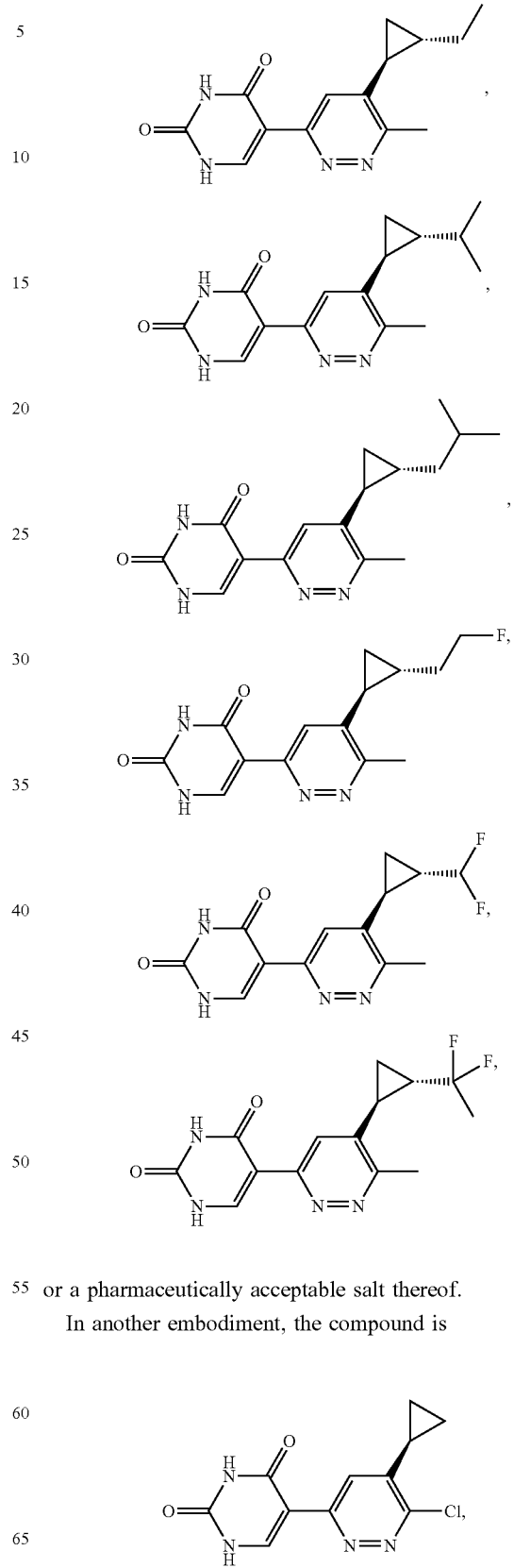
or a pharmaceutically acceptable salt thereof.
In another embodiment, the compound is -continued
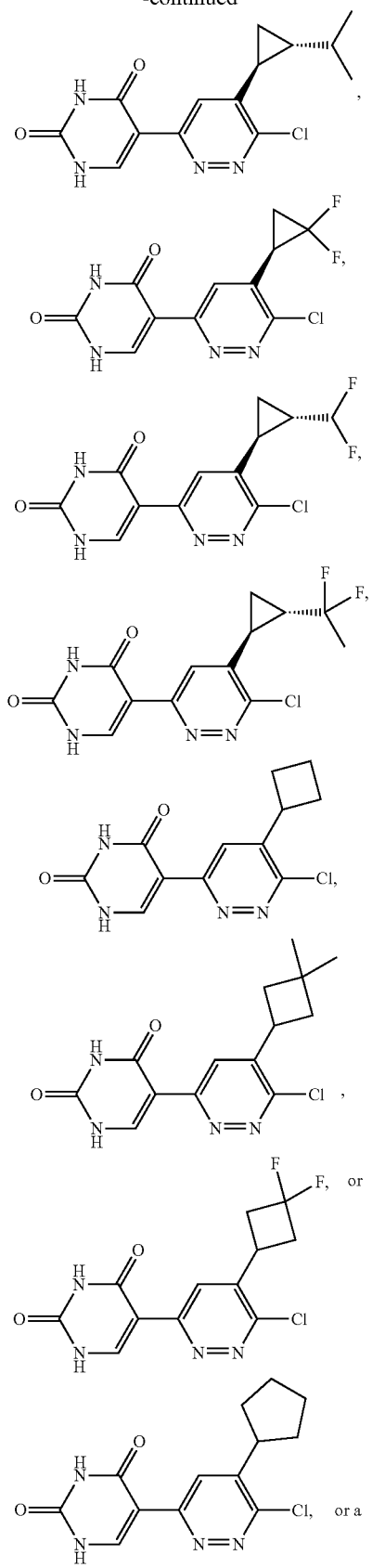
pharmaceutically acceptable salt thereof.
In another embodiment, the compound is
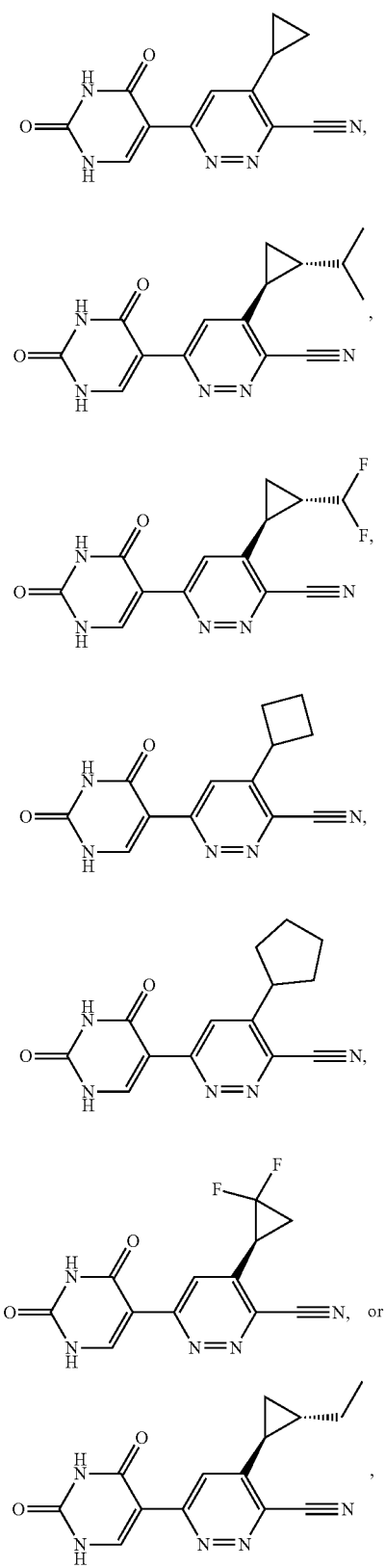
or a pharmaceutically acceptable salt thereof.

In another embodiment, the compound is

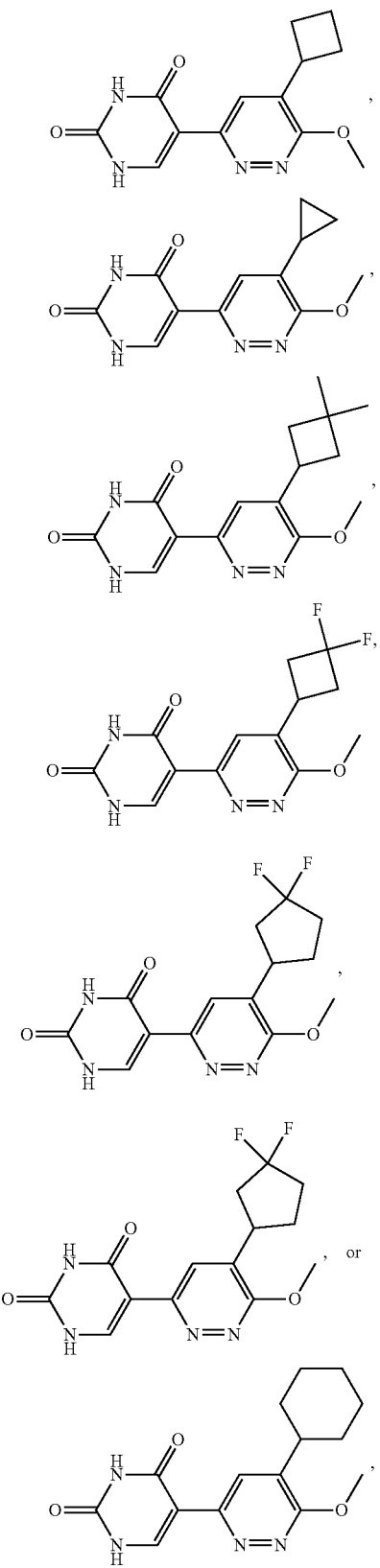

or a pharmaceutically acceptable salt thereof.

In another embodiment, the compound is

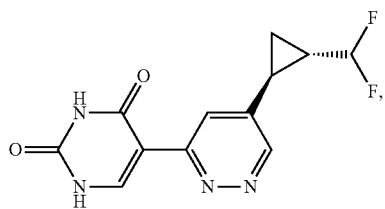

or a pharmaceutically acceptable salt thereof.

In one embodiment, the compound of Formula I is of the Formula:

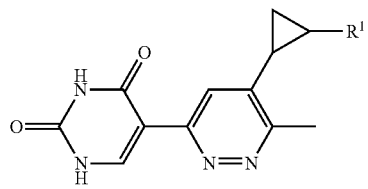

wherein $R^1$ is —CH$_2$CH$_3$ or —CH(CH$_3$)$_2$, or a pharmaceutically acceptable salt thereof. In another embodiment, $R^1$ is —CH$_2$CH$_3$, or a pharmaceutically acceptable salt thereof. In another embodiment, $R^1$ is —CH(CH$_3$)$_2$, or a pharmaceutically acceptable salt thereof.

In another embodiment, the compound of Formula I is of the Formula:

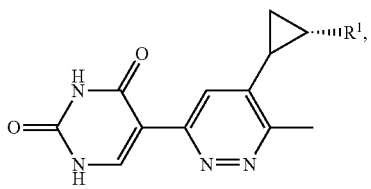

or

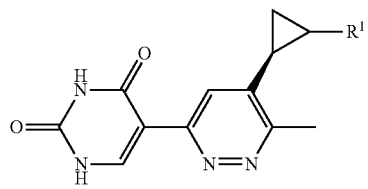

wherein $R^1$ is CH$_2$CH$_3$ or CH(CH$_3$)$_2$, or a pharmaceutically acceptable salt thereof.

In another embodiment, the compound of Formula I is of the Formula:

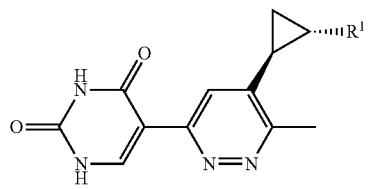

wherein R¹ is —CH₂CH₃ or —CH(CH₃)₂, or a pharmaceutically acceptable salt thereof.

In another embodiment, the present invention provides the compound:

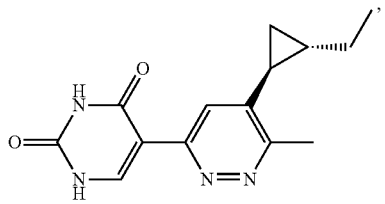 [SMILES: CC[C@H]1C[C@@H]1c1cc(-c2c[nH]c(=O)[nH]c2=O)nnc1C]

or a pharmaceutically acceptable salt thereof.

In one embodiment, the present invention provides the compound:

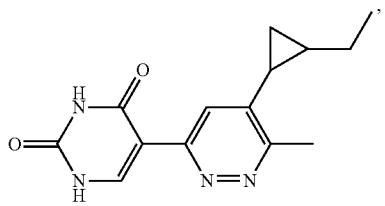 [SMILES: CCC1CC1c1cc(-c2c[nH]c(=O)[nH]c2=O)nnc1C]

or a pharmaceutically acceptable salt thereof.

In another embodiment, the present invention provides the compound:

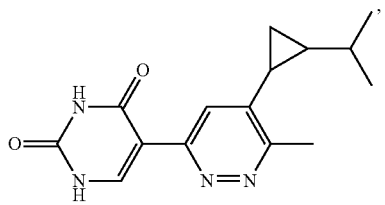 [SMILES: Cc1nnc(-c2c[nH]c(=O)[nH]c2=O)cc1C1CC1C(C)C]

or a pharmaceutically acceptable salt thereof.

In another embodiment, the present invention provides the compound:

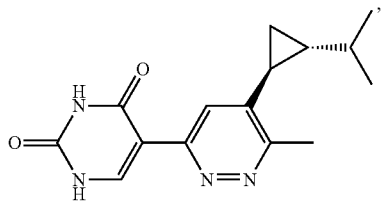 [SMILES: Cc1nnc(-c2c[nH]c(=O)[nH]c2=O)cc1[C@H]1C[C@@H]1C(C)C]

or a pharmaceutically acceptable salt thereof.

In one embodiment, the present invention provides a compound which is 5-[5-[(1S,2S)-2-ethylcyclopropyl]-6-methyl-pyridazin-3-yl]-1H-pyrimidine-2,4-dione, or a pharmaceutically acceptable salt thereof.

In another embodiment, the present invention provides a compound which is 5-[5-[(1S,2R)-2-isopropylcyclopropyl]-6-methyl-pyridazin-3-yl]-1H-pyrimidine-2,4-dione, or a pharmaceutically acceptable salt thereof.

In one embodiment, the present invention provides a pharmaceutical composition comprising 5-[5-[(1S,2S)-2-ethylcyclopropyl]-6-methyl-pyridazin-3-yl]-1H-pyrimidine-2,4-dione, or a pharmaceutically acceptable salt thereof, and one or more pharmaceutically acceptable carriers, diluents, or excipients.

In another embodiment, the present invention provides a pharmaceutical composition comprising 5-[5-[(1S,2R)-2-isopropylcyclopropyl]-6-methyl-pyridazin-3-yl]-1H-pyrimidine-2,4-dione, and one or more pharmaceutically acceptable carriers, diluents, or excipients.

In one embodiment, the present invention provides a method for treating cancer comprising administering to a patient in need thereof an effective amount of 5-[5-[(1S,2S)-2-ethylcyclopropyl]-6-methyl-pyridazin-3-yl]-1H-pyrimidine-2,4-dione, or a pharmaceutically acceptable salt thereof.

In another embodiment, the present invention provides a method for treating cancer comprising administering to a patient in need thereof an effective amount 5-[5-[(1S,2R)-2-isopropylcyclopropyl]-6-methyl-pyridazin-3-yl]-1H-pyrimidine-2,4-dione, or a pharmaceutically acceptable salt thereof.

In one embodiment, the present invention provides 5-[5-[(1S,2S)-2-ethylcyclopropyl]-6-methyl-pyridazin-3-yl]-1H-pyrimidine-2,4-dione, or a pharmaceutically acceptable salt thereof, for use in therapy.

In another embodiment, the present invention provides 5-[5-[(1S,2R)-2-isopropylcyclopropyl]-6-methyl-pyridazin-3-yl]-1H-pyrimidine-2,4-dione, or a pharmaceutically acceptable salt thereof, for use in therapy.

In one embodiment, the present invention provides 5-[5-[(1S,2S)-2-ethylcyclopropyl]-6-methyl-pyridazin-3-yl]-1H-pyrimidine-2,4-dione, or a pharmaceutically acceptable salt thereof, for use in the treatment of cancer.

In another embodiment, the present invention provides 5-[5-[(1S,2R)-2-isopropylcyclopropyl]-6-methyl-pyridazin-3-yl]-1H-pyrimidine-2,4-dione, or a pharmaceutically acceptable salt thereof, for use in the treatment of cancer.

In one embodiment, the present invention provides a pharmaceutical composition for use in treating cancer, the pharmaceutical composition comprising 5-[5-[(1S,2S)-2-ethylcyclopropyl]-6-methyl-pyridazin-3-yl]-1H-pyrimidine-2,4-dione, or a pharmaceutically acceptable salt thereof.

In another embodiment, the present invention provides a pharmaceutical composition for use in treating cancer, the pharmaceutical composition comprising 5-[5-[(1S,2R)-2-isopropylcyclopropyl]-6-methyl-pyridazin-3-yl]-1H-pyrimidine-2,4-dione, or a pharmaceutically acceptable salt thereof.

In one embodiment, the present invention provides the use of 5-[5-[(1S,2S)-2-ethylcyclopropyl]-6-methyl-pyridazin-3-yl]-1H-pyrimidine-2,4-dione, or a pharmaceutically acceptable salt thereof, in the manufacture of a medicament for the treatment of cancer.

In another embodiment, the present invention provides the use of 5-[5-[(1S,2R)-2-isopropylcyclopropyl]-6-methyl-pyridazin-3-yl]-1H-pyrimidine-2,4-dione, or a pharmaceutically acceptable salt thereof, in the manufacture of a medicament for the treatment of cancer.

In one embodiment, the present invention provides the preparation and the use of 4-chloro-6-(2,4-dimethoxypyrimidin-5-yl)-3-methyl-pyridazine, which can be structurally represented as:

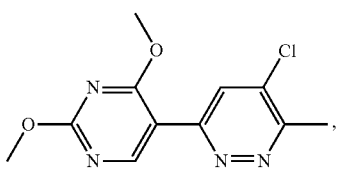

which is useful in the manufacture of a compound or a medicament for the treatment of cancer. In another embodiment, the present invention provides 4-chloro-6-(2,4-dimethoxypyrimidin-5-yl)-3-methyl-pyridazine for use in the manufacture of a compound or a medicament.

In one embodiment, the present invention provides the preparation and the use of 4,4,5,5-tetramethyl-2-(2-substituted-cyclopropyl)-1,3,2-dioxaborolane, which can be structurally represented as:

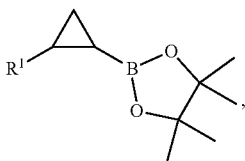

wherein $R^1$=$CH_2CH_3$ or $CH(CH_3)_2$, which is useful in the manufacture of a medicament for the treatment of cancer. In one embodiment, R=$CH_2CH_3$. In another embodiment, R=$CH(CH_3)_2$. In another embodiment, the present invention provides 4,4,5,5-tetramethyl-2-(2-substituted-cyclopropyl)-1,3,2-dioxaborolane, for use in the manufacture of a compound or a medicament.

In one embodiment, the present invention provides the preparation and the use of 2-[(1S,2S)-2-ethyl-cyclopropyl]-4,4,5,5-tetramethyl-1,3,2-dioxaborolane, which can be structurally represented as:

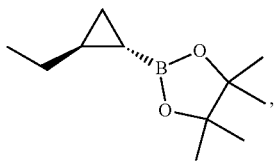

which is useful in the manufacture of a compound or a medicament for the treatment of cancer. In another embodiment, the present invention provides 2-[(1S,2S)-2-ethylcyclopropyl]-4,4,5,5-tetramethyl-1,3,2-dioxaborolane for use in the manufacture of a compound or a medicament.

In one embodiment, the present invention provides the preparation and the use of 2-[(1S,2S)-2-isopropylcyclopropyl]-4,4,5,5-tetramethyl-1,3,2-dioxaborolane, which can be structurally represented as:

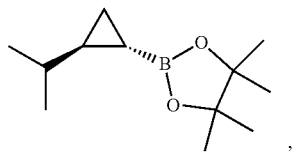

which is useful in the manufacture of a compound or a medicament for the treatment of cancer. In another embodiment, the present invention provides 2-[(1S,2S)-2-isopropylcyclopropyl]-4,4,5,5-tetramethyl-1,3,2-dioxaborolane for use in the manufacture of a compound or a medicament.

In one embodiment, the present invention provides for the chiral synthesis of 2-[(1S,2S)-2-ethylcyclopropyl]-4,4,5,5-tetramethyl-1,3,2-dioxaborolane, using (1,3-dioxoisoindolin-2-yl) (1S,2S)-2-ethylcyclopropane carboxylate, which may be structurally represented as:

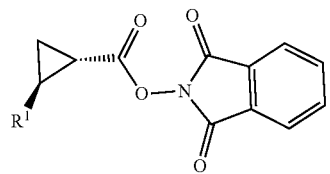

wherein $R^1$=$CH_2CH_3$ or $CH(CH_3)_2$, which is useful in the manufacture of a compound or a medicament for the treatment of cancer. In another embodiment, the present invention provides (1,3-dioxoisoindolin-2-yl) (1S,2S)-2-ethylcyclopropane carboxylate for use in the manufacture of a compound or a medicament.

In one embodiment, the present invention provides for the chiral synthesis of 2-[(1S,2S)-2-isopropylcyclopropyl]-4,4,5,5-tetramethyl-1,3,2-dioxaborolane, using (1,3-dioxoisoindolin-2-yl) (1S,2R)-2-isopropylcyclopropanecarboxylate, which may be structurally represented as:

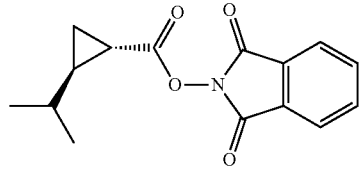

which is useful in the manufacture of a compound or a medicament for the treatment of cancer. In another embodiment, the present invention provides (1,3-dioxoisoindolin-2-yl) (1S,2R)-2-isopropylcyclopropanecarboxylate for use in the manufacture of a compound or a medicament.

The CD73 protein is expressed in many tissues, including brain, thyroid gland, adrenal gland, bone marrow, lymph node, tonsil, spleen, heart muscle, smooth muscle, lung, nasopharynx, liver, gallbladder, pancreas, salivary gland, oral mucosa, esophagus, stomach, duodenum, small intestine, colon, rectum, kidney, urinary bladder, testis, prostate, fallopian tube, vagina, breast, cervix, uterus, endometrium, ovary, soft tissue and skin (proteinatlas.org/ENSG00000135318-NT5E/tissue). CD73 is overexpressed in multiple types of tumors (Antonioli L, et al., *Nat. Rev. Cancer* 13, 842-857 (2013); Antonioli L, et al., *Trends Cancer* 2: 95-109 (2016). CD73 is also expressed in normal and pathological human hepatobiliopancreatic tissues, including hepatocytes, pancreatic ductal adenocarcinoma, and extrahepatic cholangiocellular carcinoma (Sciarra, A., et al., *Cancer Immunol Immunother* 2019; doi.org/10.1007/s00262-018-2290-1).

Elevated CD73 expression and activity are associated with tumor invasiveness and metastasis, and with shorter patient survival time (Jin D, et al., *Cancer Research* 2010; 70: 2245-2255). Increased CD73 expression has been associated with poor prognosis (Inoue K, et al., *Oncotarget* 8: 8738-8751 (2017); Turcotte K, et al., *Cancer Res.* 5: 4494-4503 (2015); Lu Y T, et al., *World J. Gastroenterol.* 19: 1912-1918 (2013); Wu X R, et al., *J. Surg. Oncol.* 106: 130-137 (2012); Buisseret S, et al., *Ann. Oncol.* 29: 1056-1062 (2017); Leclerc R, et al., *Clin. Cancer Res.* 22: 158-66 (2016)).

CD73 expression in triple-negative breast cancer is associated with worse clinical outcomes and increased resistance to anthracycline chemotherapy (Allard B, et al., *Expert Opin. Ther. Targets* 2014; 18: 863-881). CD73 is associated with poor prognosis in head and neck squamous cell carcinoma (Ren Z-H, et al., *Oncotargets* 2016; 7: 61690-61702). CD73 expression is also associated with the progression of renal cell carcinoma (Yu Y, et al., *Oncol. Lett.* 2015; 9: 2485-2494).

CD73 is overexpressed in endometrial tumors (Aliagas E, et al., *Mediators of Inflammation* 2014; doi: 10.1155/2014/509027), prostate tumor tissue (Leclerc B G, et al., *Clin. Cancer Res.* 2016; 22: 158-166), non-small cell lung cancer tissue (Inoue Y, et al., *Oncotarget* 2017; 8: 8738-8751). CD73 has been reported to be overexpressed in tumors, including breast cancer, colorectal cancer, ovarian cancer, gastric cancer and gallbladder cancer (Gao Z-W and Zhang H-Z, *Biomed Res. Int.* 2014; doi: 10.1155/2014/460654). CD73 has been reported to be overexpressed in cancer cell lines, including glioblastoma, melanoma, breast, ovarian, medulloblastoma, and bladder cancer cell lines (Gao Z-W and Zhang H-Z, *Biomed Res. Int.* 2014; doi: 10.1155/2014/460654).

CD73-adenosine has been reported to reduce immune responses and survival in ovarian cancer patients (Gaudreau P-O, et al., *Oncoimmunology* 2016; 5(5): e1127496).

CD73 blockade in vivo with a the selective CD73 inhibitor α,β-methyleneadenosine 5'-diphosphate has been reported to reduce tumor growth in syngeneic mice injected subcutaneously with EG7 (lymphoma), MC38 (colon), AT-3 (breast) and B16F10 (melanoma) tumor cells (Stagg J, et al., *Cancer Research* 2011; 71: 2892-2900; Forte G, et al., *J. Immunol.* 2012; 189: 2226-2233). Anti-CD73 antibody therapy has been reported to inhibit breast tumor growth and metastasis (Stagg J, et al., *PNAS* 2010; 107: 1547-1552; Terp M G, *J. Immunol.* 2013; 191: 4165-4173).

In addition, adenosine and CD73 enzyme activity has been reported to be increased in cancer patients (Huang N, et al., *Cancer Res.* 75:1538 (2015), and patients who do not respond to the immune checkpoint inhibitors have been reported to have a higher adenosine level than those who respond (Giannakis H X, et al., *J. Clin. Oncol.* 35: 15 Suppl. 3036-3036 (2017)).

Oncogenic activation and estrogen receptor loss has been reported to associate with increased CD73 expression (Reinhardt J, et al., *Cancer Res.* 77: 4697-4709 (2017); Spychala J, et al., *Clin. Cancer Res.* 10:708-17 (2004); Ascierto and McArthur J., *Transl. Med.* 15: 173 (2017); Young A, et al, *Cancer Res.* 77:4684-4696 (2017)).

Subjects that can benefit from CD73 inhibitor treatment include those with tumors resistant or refractory to the anti-PD1/PDL-1 inhibitors, such as non-small cell lung cancer, bladder cancer, and melanoma; those with EGFR/BRAF/Kras mutant cancers, such as non-small cell lung cancer, bladder cancer, melanoma, colon, and pancreas; those with estrogen receptor (−) cancers, such as triple negative breast cancer; subjects with high expression level of CD73, such as pancreatic cancer and colorectal cancer. If desired, such subject can be selected for therapy with a compound disclosed herein, or a pharmaceutically acceptable salt thereof, based on the presence of high CD73 expression levels in their tumors, as measured by an IHC assay; or based on the presence of EGFR and BRAF mutations in their tumors as detected by RT-PCR assays; or based on the loss of estrogen receptor in their tumors, as detected by an IHC or RT-PCR assay; or based on the presence of high levels of adenosine and AMP in their tumors or plasma as detected by an LC-MS assay. For pharmacodynamic assessment, an LC-MS based ex vivo assay described herein can be used to measure the effect of a CD73 inhibitor on the conversion of AMP to adenosine in the blood.

The present invention also provides a method of treating cancer in a patient, comprising administering to a patient in need thereof an effective amount of a compound of Formula I, or a pharmaceutically acceptable salt thereof.

The present invention also provides a method of treating cancer, comprising administering to a subject in need thereof an effective amount of a compound of Formula I herein, or a pharmaceutically acceptable salt thereof, in which the cancer is bladder cancer, breast cancer, cholangiocarcinoma, colorectal cancer, colon cancer, gastric cancer, gallbladder cancer, glioblastoma, head and neck cancer, liver cancer, lung cancer, lymphoma, medulloblastoma, melanoma, ovarian cancer, pancreatic cancer, prostate cancer or renal cancer. In one embodiment, the breast cancer is triple-negative breast cancer. In another embodiment, the lung cancer is non-small cell lung cancer. In one preferred embodiment, the compound is 5-[5-[(1S,2R)-2-isopropylcyclopropyl]-6-methyl-pyridazin-3-yl]-1H-pyrimidine-2,4-dione.

In one embodiment, the patient is one in whom the serum CD73 activity has been determined. In one preferred embodiment, "determining CD73 activity" means determining if CD73 activity is present. Methods for determining the level of CD73 expression or CD73 activity are known to those of ordinary skill in the art, e.g., see S Morello, et al., *J. Trans. Med.* 2017; 15:244. In another preferred embodiment, "determining CD73 activity" means quantifying the level of AMP conversion to adenosine by CD73, and an LC-MS based assay is provided herein that facilitates quantifying the level of CD73 activity.

In another embodiment, the patient is one in whom CD73 expression in tissue has been determined. In another embodiment, the tissue is tumor tissue. Methods for determining the level of CD73 expression in tissue are known to those of ordinary skill in the art, e.g., using western blotting or immunohistochemistry (X-R Wu, et al., *J. Surg. Oncol.* 2012; 106: 130-137).

The present invention also provides a method, comprising determining CD73 expression in tissue from a patient to whom the compound according to any one of claims 1-12, or a pharmaceutically acceptable salt thereof, has been administered. In a preferred embodiment, the tissue is tumor tissue.

The present invention also provides a method, comprising determining CD73 activity in the serum from a patient to whom the compound according to a compound of Formula I herein, or a pharmaceutically acceptable salt thereof, has been administered. This method is sensitive, does not involve tumor biopsies, does not involve antibodies or immunohistochemistry, facilitates quantification of CD73 activity (e.g., by facilitating the calculation of an $EC_{50}$). In one preferred embodiment, the compound is 5-[5-[(1S,2R)-2-Isopropylcyclopropyl]-6-methyl-pyridazin-3-yl]-1H-pyrimidine-2,4-dione. In another preferred embodiment, the method further comprises assaying CD73 activity using radiolabeled adenosine monophosphate (AMP) and determining the radiolabeled AMP concentration using mass spectrometry. In another preferred embodiment, the radiolabeled AMP is 13C5_15N5-AMP.

In another preferred embodiment, the method comprises (a) providing serum from the patient in each of a plurality of containers (e.g., a microtitre plate) that are configured to contain various concentrations of the compound that administered to the patient, (b) providing the 13C10_15N5_AMP in each container in the plurality of containers, (c) incubating the plurality of containers under conditions that facilitate mixing (e.g., shaking), (d) centrifuging the plurality of containers, (e) transferring the supernatant from each container to a new respective container, (f) providing an extraction solution containing internal standard in each of the new respective containers, (g) centrifuging the new respective containers, (h) transferring the supernatant from each new respective container to a respective analysis container, (i) assaying the supernatant in each respective analysis container for 13C10_15N5_adenosine, 13C10_15N4_inosine and 15N4 hypoxanthine by LC/MS, as described herein ("Mass Spectroscopy for Adenosine and Adenosine Purification"), and (j) calculating the $EC_{50}$. In one preferred embodiment, the compound is 5-[5-[(1S,2R)-2-Isopropylcyclopropyl]-6-methyl-pyridazin-3-yl]-1H-pyrimidine-2,4-dione. In a preferred embodiment, the internal standard is 13C5-AMP, 13C5-Adenosine, 15N4-inosine, and 13C5-Hypoxanthine.

The present invention also provides use of a compound of Formula I herein, or a pharmaceutically acceptable salt thereof, in therapy. In one embodiment, the therapy is the treatment of cancer. In another embodiment, the cancer is bladder cancer, breast cancer, cholangiocarcinoma, colorectal cancer, colon cancer, gastric cancer, gallbladder cancer, glioblastoma, head and neck cancer, liver cancer, lung cancer, lymphoma, medulloblastoma, melanoma, ovarian cancer, pancreatic cancer, prostate cancer or renal cancer. In one embodiment, the breast cancer is triple-negative breast cancer. In another embodiment, the lung cancer is non-small cell lung cancer. In one preferred embodiment, the compound is 5-[5-[(1S,2R)-2-Isopropylcyclopropyl]-6-methyl-pyridazin-3-yl]-1H-pyrimidine-2,4-dione.

The present invention also provides use of a compound of Formula I herein, or a pharmaceutically acceptable salt thereof, for the manufacture of a medicament for the treatment of cancer. In one embodiment, the cancer is bladder cancer, breast cancer, cholangiocarcinoma, colorectal cancer, colon cancer, gastric cancer, gallbladder cancer, glioblastoma, head and neck cancer, liver cancer, lung cancer, lymphoma, medulloblastoma, melanoma, ovarian cancer, pancreatic cancer, prostate cancer or renal cancer. In one embodiment, the breast cancer is triple-negative breast cancer. In another embodiment, the lung cancer is non-small cell lung cancer. In one preferred embodiment, the compound is 5-[5-[(1S,2R)-2-Isopropylcyclopropyl]-6-methyl-pyridazin-3-yl]-1H-pyrimidine-2,4-dione.

In one embodiment, the present invention provides a method of treating cancer, comprising administering an effective amount of a compound of Formula I herein, or a pharmaceutically acceptable salt thereof, in simultaneous, separate, or sequential combination with one or more anti-tumor agents. Non-limiting examples of anti-tumor agents include ramucirumab, necitumumab, olaratumab, gemcitabine, pemetrexed, galunisertib, abemaciclib, gefitinib, vemurafenib, dabrafenib, trametinib, cisplatin, carboplatin, dacarbazine, liposomal doxorubicin, docetaxel, cyclophosphamide and doxorubicin, navelbine, eribulin, paclitaxel, paclitaxel protein-bound particles for injectable suspension, ixabepilone, capecitabine, FOLFOX (leucovorin, fluorouracil, and oxaliplatin), FOLFIRI (leucovorin, fluorouracil, and irinotecan), cetuximab, an EGFR inhibitor, a Raf inhibitor, a B-Raf inhibitor, an ERK inhibitor, a CDK4/6 inhibitor, an idoleamine 2,3-dioxygenase inhibitor, a TGFβ inhibitor, and a TGFβ receptor inhibitor.

In a another embodiment, the present invention provides a method of treating cancer, comprising administering an effective amount of a compound of Formula I herein, or a pharmaceutically acceptable salt thereof, in simultaneous, separate, or sequential combination with one or more immuno-oncology agents. In one preferred embodiment, the immune-oncology agent is an anti-PD-1 antibody, an anti-PD-L1 antibody, an anti-CD137 agonist antibody, or an anti-CTLA4 antibody. Non-limiting examples of immuno-oncology agents include nivolumab, ipilimumab, pidilizumab, pembrolizumab, tremelimumab, urelumab, lirilumab, atezolizumab, durvalumab, and the anti-PD-L1 antibody LY3300054 (the heavy and light chain sequences of which are forth in WO 2017/034916 and US 2017/0058033 as SEQ ID NOS: 10 and 11, respectively). In one preferred embodiment, the immune-oncology agent is an anti-PD-1 antibody. In another preferred embodiment, the immune-oncology agent is an anti-PD-L1 antibody. In another preferred embodiment, the compound is 5-[5-[(1S,2R)-2-isopropylcyclopropyl]-6-methyl-pyridazin-3-yl]-1H-pyrimidine-2,4-dione, and the immune-oncology agent is LY3300054.

In one embodiment, the present invention provides a method of treating non-small cell lung cancer, comprising administering an effective amount of a compound of Formula I herein, or a pharmaceutically acceptable salt thereof, in simultaneous, separate, or sequential combination with another agent. In one preferred embodiment, the other agent is osimertinib, cetuximab or abemaciclib. In another preferred embodiment, the other agent is osimertinib. In another preferred embodiment, the other agent is cetuximab. In another preferred embodiment, the other agent is abemaciclib.

In another embodiment, the present invention provides a method of treating melanoma, comprising administering an effective amount of a compound of Formula I herein, or a pharmaceutically acceptable salt thereof, in simultaneous, separate, or sequential combination with another agent. In one preferred embodiment, the other agent is a BRAF inhibitor, an anti-PD-1 antibody, or an anti-PD-L1 antibody. In another preferred embodiment, the other agent is a BRAF inhibitor. In another preferred embodiment, the other agent is an anti-PD-1 antibody. In another preferred embodiment, the other agent is an anti-PD-L1 antibody. In another preferred embodiment, the anti-PD-L1 antibody is LY3300054. In another preferred embodiment, the compound is 5-[5-[(1S,2R)-2-isopropylcyclopropyl]-6-methyl-pyridazin-3-yl]-1H-pyrimidine-2,4-dione and the other agent is the anti-PD-L1 antibody is LY3300054.

In another embodiment, the present invention provides a method of treating colorectal cancer, comprising administering an effective amount of a compound of Formula I herein, or a pharmaceutically acceptable salt thereof, in simultaneous, separate, or sequential combination with another agent. In one preferred embodiment, the other agent is abemaciclib. In another preferred embodiment, the compound is 5-[5-[(1S,2R)-2-isopropylcyclopropyl]-6-methyl-pyridazin-3-yl]-1H-pyrimidine-2,4-dione, and the other agent is abemaciclib.

In another embodiment, the present invention provides a method of treating pancreatic cancer, comprising administering an effective amount of a compound of Formula I herein, or a pharmaceutically acceptable salt thereof, in simultaneous, separate, or sequential combination with another agent. In one preferred embodiment, the other agent is abemaciclib. In another preferred embodiment, the compound is 5-[5-[(1S,2R)-2-isopropylcyclopropyl]-6-methylpyridazin-3-yl]-1H-pyrimidine-2,4-dione, and the other agent is abemaciclib.

In another embodiment, the present invention provides a method of treating triple-negative breast cancer, comprising administering an effective amount of a compound of Formula I herein, or a pharmaceutically acceptable salt thereof, in simultaneous, separate, or sequential combination with another agent. In one preferred embodiment, the compound is 5-[5-[(1S,2R)-2-isopropylcyclopropyl]-6-methylpyridazin-3-yl]-1H-pyrimidine-2,4-dione.

The present invention also provides a method of inhibiting CD73 enzymatic activity in a patient, comprising administering to a patient in need thereof an effective amount of a compound of Formula I, or a pharmaceutically acceptable salt thereof. The present invention also provides a method of inhibiting the conversion of AMP to adenosine in a patient, comprising administering to a patient in need thereof an effective amount of a compound of Formula I, or a pharmaceutically acceptable salt thereof.

In another embodiment, the present invention provides a method of treating cancer, comprising the administration of an effective amount of a compound of Formula I herein, or a pharmaceutically acceptable salt thereof, in simultaneous, separate, or sequential combination with one or more agents that modulate adenosine. Non-limiting examples of agents that modulate adenosine include an anti-CD73 antibody and an adenosine receptor antagonist.

The present invention also provides a pharmaceutical composition, comprising a compound of Formula I, or a pharmaceutically acceptable salt thereof, with one or more pharmaceutically acceptable carriers, diluents, or excipients. The invention further provides a process for preparing a pharmaceutical composition, comprising admixing a compound of Formula I, or a pharmaceutically acceptable salt thereof, with one or more pharmaceutically acceptable carriers, diluents, or excipients. This invention also encompasses novel intermediates and processes for synthesis of the compounds of Formula I.

As used above, and throughout the description of the invention, the following terms, unless otherwise indicated, shall be understood to have the following meanings:

A "pharmaceutically acceptable carrier, diluent, or excipient" is a medium generally accepted in the art for the delivery of biologically active agents to mammals, e.g., humans.

The terms "treatment," "treat," "treating," and the like, are meant to include slowing or reversing the progression of a disorder. These terms also include alleviating, ameliorating, attenuating, eliminating, or reducing one or more symptoms of a disorder or condition, even if the disorder or condition is not actually eliminated and even if progression of the disorder or condition is not itself slowed or reversed.

"Effective amount" means the amount of the compound, or pharmaceutically acceptable salt thereof, of the present invention or pharmaceutical composition containing a compound, or pharmaceutically acceptable salt thereof, of the present invention that will elicit the biological or medical response of or desired therapeutic effect on a patient by a treating clinician. In one embodiment, the compound, or a pharmaceutically acceptable salt thereof, inhibits the conversion of AMP to adenosine in an in vitro or ex vivo CD73 enzyme assay. In another embodiment, the compound, or a pharmaceutically acceptable salt thereof, inhibits the conversion of AMP to adenosine in mouse whole blood from animals treated with different doses of the compound.

"Gem-difluoro" refers to two fluorine atoms bonded to the same carbon.

"Gem-dimethyl" refers to two methyl groups bonded to the same carbon.

As used herein, the term "patient" refers to a human.

An effective amount can be readily determined by the attending diagnostician, as one skilled in the art, by the use of known techniques and by observing results obtained under analogous circumstances. In determining the effective amount for a patient, a number of factors are considered by the attending diagnostician, including, but not limited to: the species of patient; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compounds of the present invention can be used over a wide dosage range. For example, dosages per day normally fall within the range of about 0.01 to about 50 mg/kg of body weight.

The compounds of the present invention are preferably formulated as pharmaceutical compositions administered by any route which makes the compound bioavailable, including oral, intravenous, and transdermal routes. Most preferably, such compositions are for oral administration. Such pharmaceutical compositions and processes for preparing same are well known in the art. (See, e.g., Remington: The Science and Practice of Pharmacy (D. B. Troy, Editor, 21st Edition, Lippincott, Williams & Wilkins, 2006).

It will be understood by the skilled artisan that compounds of the present invention are capable of forming salts. The compounds of the present invention contain basic heterocycles, and accordingly react with any of a number of inorganic and organic acids to form pharmaceutically acceptable acid addition salts. Such pharmaceutically acceptable acid addition salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2008)

"Pharmaceutically acceptable salts" or "a pharmaceutically acceptable salt" refers to the relatively non-toxic, inorganic and organic salt or salts of the compound of the present invention (S. M. Berge, et al., "Pharmaceutical Salts", *Journal of Pharmaceutical Sciences*, Vol 66, No. 1, January 1977).

The designation of "isomer 1" in a compound name signifies that the corresponding intermediate or compound of the present invention is the first of two eluting enantiomers when a mixture of a pair of enantiomers is separated by chiral chromatography under the conditions described in the "Preparations and Examples" below. The designation of "isomer 2" in a compound name represents that the corresponding intermediate or compound of the present invention that is the second of two eluting enantiomers when the mixture of a pair of enantiomers is separated by chiral chromatography under the conditions described in the "Preparations and Examples" below.

The compounds of the present invention can be prepared according to synthetic methods well known and appreciated in the art. Suitable reaction conditions for the steps of these reactions are well known in the art and appropriate substitutions of solvents and co-reagents are within the skill of the art. Likewise, it will be appreciated by those skilled in the art that synthetic intermediates may be isolated and/or purified by various well known techniques as needed or desired, and that frequently, it will be possible to use various intermediates directly in subsequent synthetic steps with little or no purification. Furthermore, the skilled artisan will appreciate that in some circumstances, the order in which moieties are introduced is not critical. The particular order of steps required to produce the compounds of the present invention is dependent upon the particular compound being synthesized, the starting compound, and the relative liability of the substituted moieties, as is well appreciated by the skilled chemist. All substituents, unless otherwise indicated, are as previously defined, and all reagents are well known and appreciated in the art.

As used herein, the following terms have the meanings indicated: "ACN" refers to acetonitrile; "DAST" refers to diethylaminosulfur trifluoride, "DCM" refers to dichloromethane; "DMAP" refers to 4-dimethylaminopyridine; "dmso" or "DMSO" refers to dimethyl sulfoxide; "ee" refers to enantiomeric excess; "ES/MS" refers to Electrospray Mass Spectrometry; "EtOAc" refers to ethyl acetate; "Et$_2$O" refers to diethyl ether; "FBS" refers to fetal bovine serum; "GC-MS" refers to Gas Chromatography-Mass Spectometry; "HBSS" refers to Hank's Balanced Salt Solution; "IC$_{50}$" refers to half maximal inhibitory concentration; "LAH" refers to lithium aluminum hydride; "LC-ES/MS" refers to Liquid Chromatography Electrospray Mass Spectometry; "MS" refers to Mass Spectrometry; "MeOH" refers to methanol; "MTBE" refers to methyl tert-butyl ether; "nBuLi" refers to n-butyllithium; "nm" refers to nanometer or nanometers; "NMR" refers to nuclear magnetic resonance; "OAc" refers to acetate; "psi" refers to pounds per square inch; "RT" refers to room temperature or ambient temperature; "SCX" refers to StrongCation Exchange; "SFC" refers to Super-critical Fluid Chromatography; "S$_N$Ar" refers to nucleophilic aromatic substitution; "TEA" refers to triethylamine; "THF" refers to tetrahydrofuran; "t$_R$" refers to retention time; and "w/w" refers to weight/weight proportions in solution.

Compounds of the present invention may be synthesized as illustrated in the following schemes.

Scheme 1

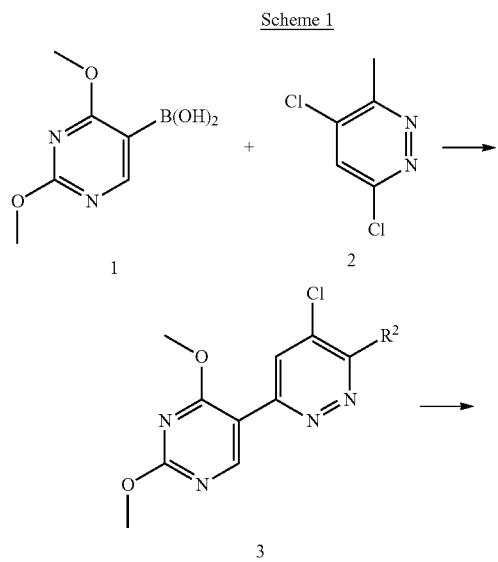

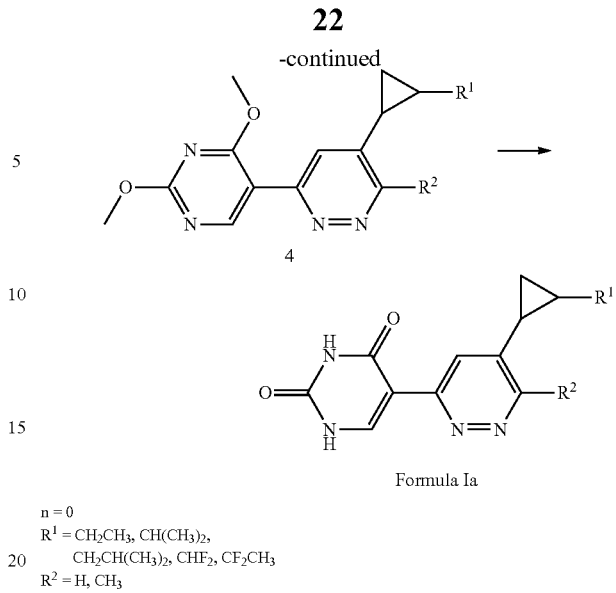

Formula Ia n = 0
R$^1$ = CH$_2$CH$_3$, CH(CH$_3$)$_2$,
  CH$_2$CH(CH$_3$)$_2$, CHF$_2$, CF$_2$CH$_3$
R$^2$ = H, CH$_3$ Scheme 1 depicts the preparation of the compounds of Formula Ia. Using well-known Suzuki-type conditions, commercially available (2,4-dimethoxypyrimidin-5-yl)boronic acid 1 may be coupled to 4,6-dichloro-3-methylpyridazine. Subsequent Suzuki-coupling of the chloro moiety of 3 with an appropriately substituted trans-cyclopropylboronate may be accomplished to obtain 4. The skilled artisan will recognize that the enantiomers of compound 4 may be separated using chiral separation techniques well known in the art. Compounds of Formula Ia may be prepared by deprotection of the methoxy groups in 4 under an array of demethylation conditions well described in the art.

Scheme 2

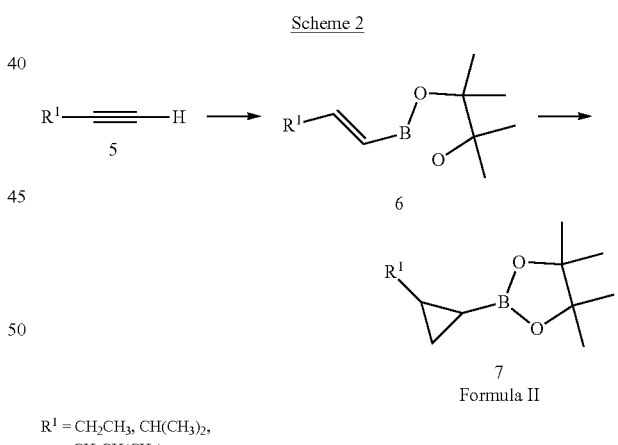

Formula II

R$^1$ = CH$_2$CH$_3$, CH(CH$_3$)$_2$,
  CH$_2$CH(CH$_3$)$_2$

Scheme 2 depicts the requisite cyclopropyl boronic esters needed to prepare compounds of Formula II. The skilled artisan will recognize that hydroboration of the appropriately substituted alkyne 5 may be effected under an array of conditions, especially in the presence of a transition-metal catalyst such as Cu or Zr, to obtain the alkenyl boronate 6. The alkenyl boronate may be cyclopropanated under stabilized carbenoid-type conditions well known in the art, such as Simmons-Smith cyclopropanation, Corey-Chaykovsky reaction, and the method of cyclopropanation with diazomethane (or diazo compounds) both with (e.g., Cu, Pd, or Ni) and without (e.g., thermally or photochemically) transition metal catalysts, to obtain the appropriately substituted trans-cyclopropylboronate 7. The skilled artisan will recognize that the thermodynamically favored cyclopropanation product will be a mixture of trans enantiomers in 7.

complexation of the N-hydroxyphthalimide ester with diboron in a radical coupling facilitated by a pyridine-boron radical, to obtain the trans-cyclopropane boronate 15. (See, e.g., W.-M. Cheng; S. Rui; B. Zhao; W.-L. Xing; Y. Fu. *Org. Lett.* 2017, 19, 4291-4294.) Coupling of the boronate 15

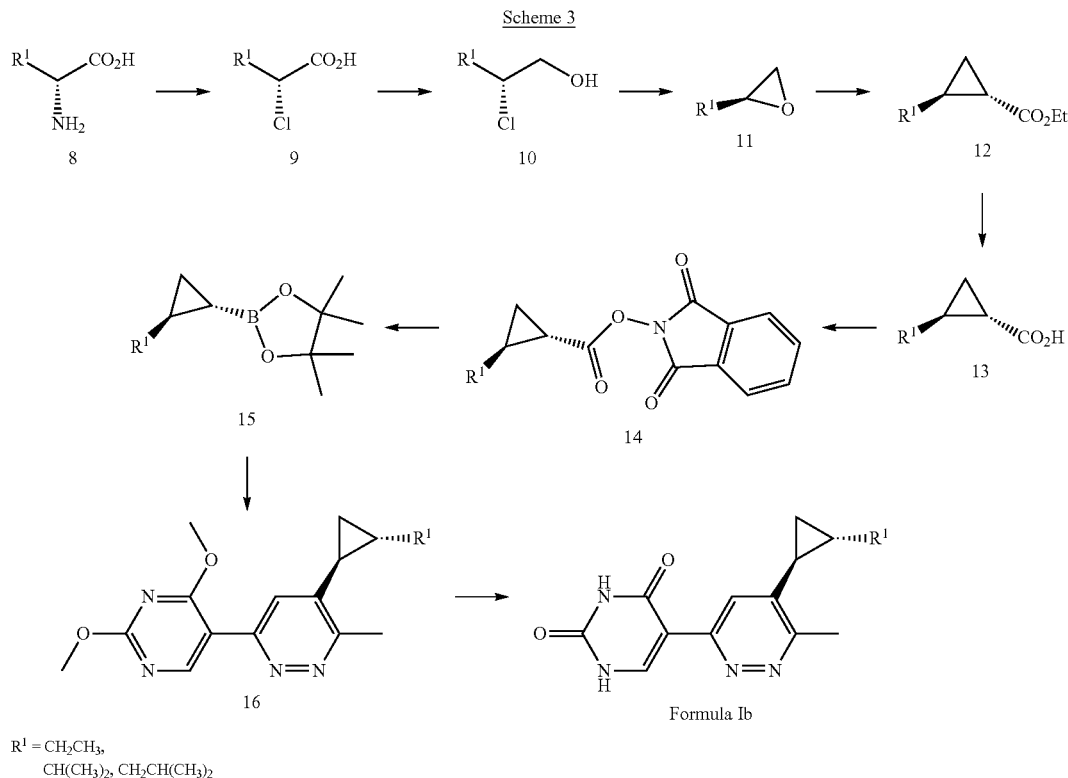

Scheme 3

$R^1 = CH_2CH_3$, $CH(CH_3)_2$, $CH_2CH(CH_3)_2$

Scheme 3 depicts the chiral synthesis of compounds of Formula Ib. Diazotization of the appropriately substituted amino acid 8 under modified Sandmeyer conditions (radical SNAr) to give 9 is well known in the art. Subsequent reduction to alcohol 10 may be accomplished utilizing an array of reducing agents well known in the art, including aluminum hydrides and diborane as reducing agents. Cyclization to the chiral epoxide 11 under basic conditions is well described in the art. A stereoselective Horner-Wadsworth-Emmons reaction may be used by treating the chiral epoxide 11 with a suitable phosphonate ester (e.g., ethyl 2-diethoxyphosphorylacetate or triethylphosphonoacetate) and suitable base (e.g., alkyllithium, metal alkoxides, or metal hydrides) to obtain the trans-cyclopropane derivative 12 (See, e.g., L. Delhaye; A. Merschaert; P. Delbeke; W. Brione. *Org. Proc. Res. & Dev.* 2007, 11, 689-692.) Hydrolysis of compound 12 to the corresponding acid 13 may be accomplished under a wide array of basic conditions well described in the art. Subsequent coupling of acid 13 with an appropriately substituted N-hydroxy phthalimide is well described in the art, utilizing a suitable acid-activating agent, e.g., carbonyldiimidazole, in the presence of a mild non-nucleophilic base, to prepare compound 14. Decarboxylative borylation of the N-hydroxypthalimide ester 14 may be accomplished under many conditions known in the art, including in the presence of a transition metal catalyst (e.g., Suzuki-Miyaura reaction), under photolytic conditions, or by single electron transfer reactions, including, for example, with arylchloride 4 and subsequent demethylation may be performed similarly to that described in Scheme 1 to obtain the chiral compound types of Formula Ib.

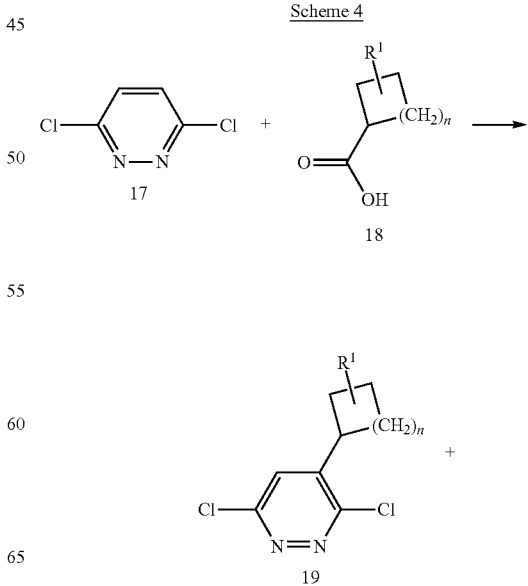

Scheme 4

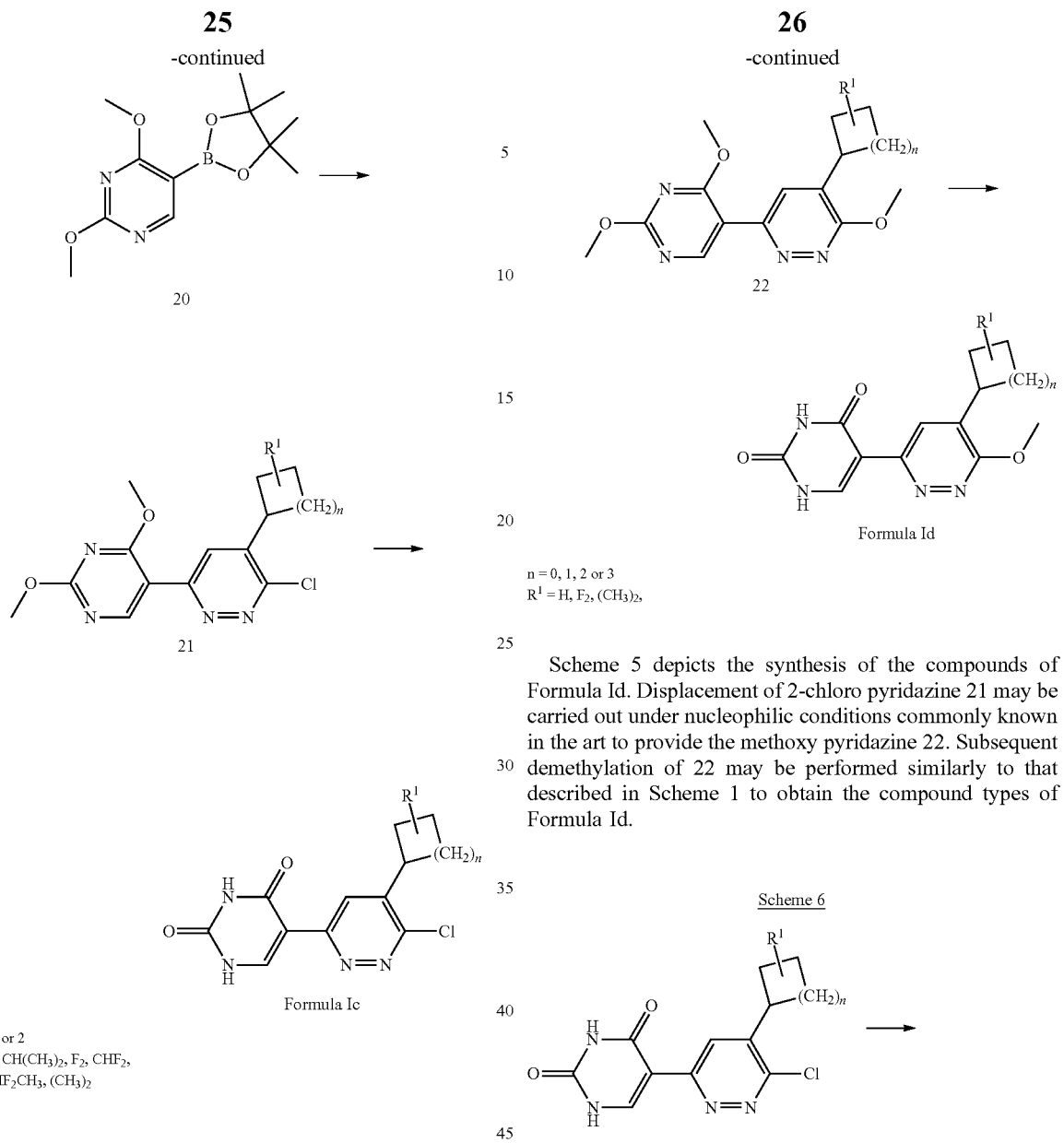

Scheme 5 depicts the synthesis of the compounds of Formula Id. Displacement of 2-chloro pyridazine 21 may be carried out under nucleophilic conditions commonly known in the art to provide the methoxy pyridazine 22. Subsequent demethylation of 22 may be performed similarly to that described in Scheme 1 to obtain the compound types of Formula Id.

Scheme 4 depicts the synthesis of compounds of Formula Ic. Nucleophilic substitution of dichlorpyridazine 17 may be carried out under radical conditions (e.g., Minisci Reaction) well known in the art to obtain substituted pyridazine 19. Coupling of the boronate 20 with arylchloride 19 and subsequent demethylation may be performed similarly to that described in Scheme 1 to obtain the compound types of Formula Ic.

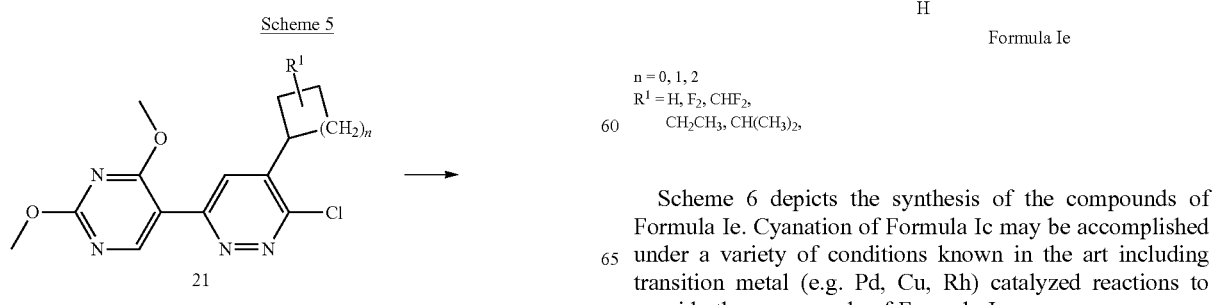

Scheme 6 depicts the synthesis of the compounds of Formula Ie. Cyanation of Formula Ic may be accomplished under a variety of conditions known in the art including transition metal (e.g. Pd, Cu, Rh) catalyzed reactions to provide the compounds of Formula Ie.

Scheme 7

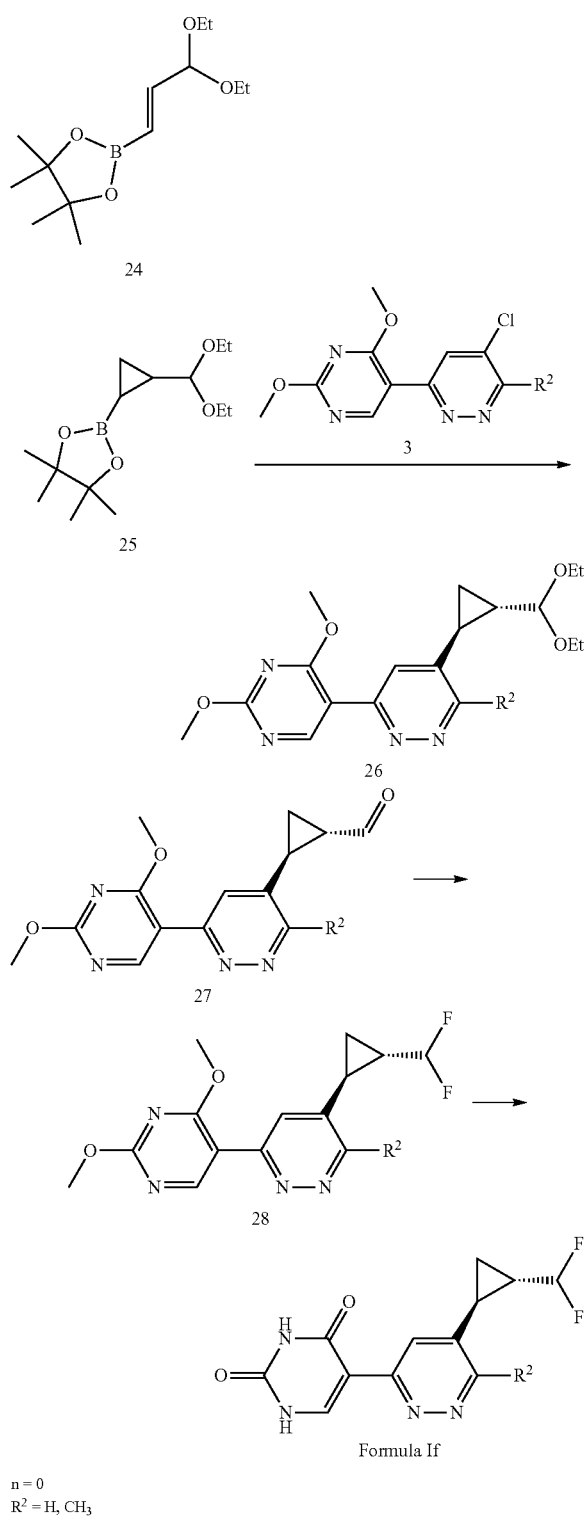

n = 0
R² = H, CH₃

Scheme 7 depicts the synthesis of the compounds of Formula If. The alkenyl boronate may be cyclopropanated similarly to that described in Scheme 2. Coupling of the boronate 25 with arylchloride 3 may be performed similarly to that described in Scheme 1 to obtain the chiral compound 26. Unmasking diethylacetal 26 to aldehyde 27 may be achieved by treatment with the appropriate acid. Treatment of aldehyde 27 with a variety of fluorinating reagents (e.g. DAST, XtalFluor®, Fluolead™ or Deoxo-Fluor®) may provide difluoromethyl 28. Subsequent demethylation of 28 may be performed similarly to that described in Scheme 1 to obtain the compound types of Formula If.

Scheme 8

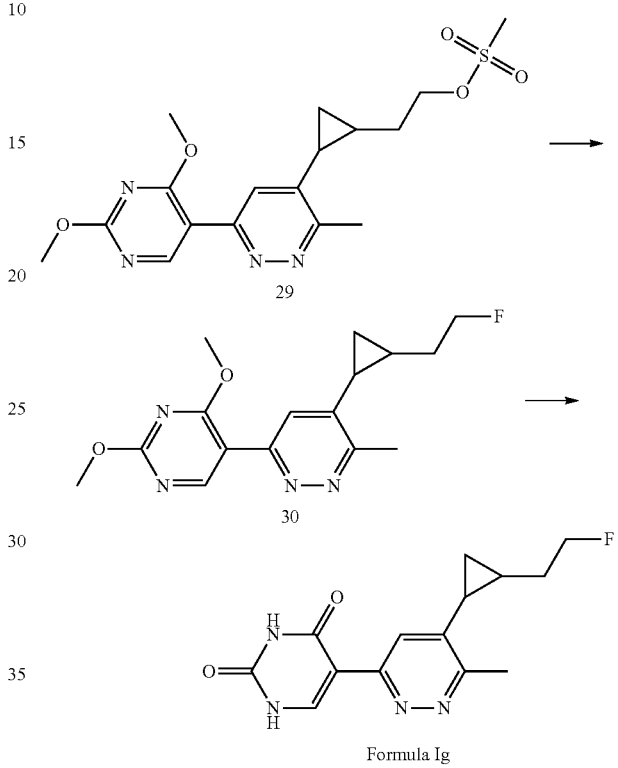

Scheme 8 depicts the synthesis of the compounds of Formula Ig. Methanesulfonate 29 may be converted to fluoride 30 using substitution techniques known to the skilled artisan with reagents such as potassium fluoride or tertbutylammonium fluoride. Subsequent demethylation may be performed similarly to that described in Scheme 1 to obtain the chiral compound of Formula Ig.

PREPARATIONS AND EXAMPLES

The following Preparations and Examples further illustrate the invention and represent typical synthesis of the compounds of the invention, but should not be construed to limit the scope of the invention in any way. The reagents and starting materials are readily available or may be readily synthesized by one of ordinary skill in the art. It should be understood that the Preparations and Examples are set forth by way of illustration and not limitation, and that various modifications may be made by one of ordinary skill in the art.

LC-ES/MS is performed on an Agilent HP1100 liquid chromatography system. Electrospray mass spectrometry measurements (acquired in positive and/or negative mode) are performed on a Mass Selective Detector quadrupole mass spectrometer interfaced to the HP1100 HPLC. LC-MS conditions (low pH): column: PHENOMENEX® GEMINI® NX C-18 2.1×50 mm 3.0 µm; gradient: 5-100%

B in 3 min, then 100% B for 0.75 min column temperature: 50° C.+/−10° C.; flow rate: 1.2 mL/min; Solvent A: deionized water with 0.1% HCOOH; Solvent B: ACN with 0.1% formic acid; wavelength 214 nm. Alternate LC-MS conditions (high pH): column: WATERS™ XTERRA® MS C-18 columns 2.1×50 mm, 3.5 μm; gradient: 5% of solvent A for 0.25 min, gradient from 5% to 100% of solvent B in 3 min and 100% of solvent B for 0.5 min or 10% to 100% of solvent B in 3 min and at 100% of solvent B for 0.75 min; column temperature: 50° C.+/−10° C.; flow rate: 1.2 mL/min; Solvent A: 10 mM NH$_4$HCO$_3$ pH 9; Solvent B: ACN; wavelength: 214 nm.

Preparative reversed phase chromatography is performed on an Agilent 1200 LC-ES/MS equipped with a Mass Selective Detector mass spectrometer and a Leap autosampler/fraction collector. High pH methods are run on a 75×30 mm PHENOMENEX® GEMINI®-NX, 5 μm particle size column with a 10×20 mm guard. Flow rate of 85 mL/min. Eluent is 10 mM ammonium bicarbonate (pH 10) in ACN.

NMR spectra are performed on a Bruker AVIII HD 400 MHz NMR Spectrometer, obtained as CDCl$_3$ or (CD$_3$)$_2$SO solutions reported in ppm, using residual solvent [CDCl$_3$, 7.26 ppm; (CD$_3$)$_2$SO, 2.50 ppm] as a reference standard. When peak multiplicities are reported, the following abbreviations may be used: s (singlet), d (doublet), t (triplet), q (quartet), m (multiplet), br-s (broad singlet), dd (doublet of doublets), dt (doublet of triplets). Coupling constants (J), when reported, are reported in hertz (Hz).

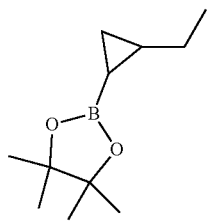

To a solution of 2-[(E)-but-1-enyl]-4,4,5,5-tetramethyl-1,3,2-dioxaborolane (1.65 g, 9.06 mmol) in Et$_2$O (45.30 mL) add Pd(OAc)$_2$ (0.20 g, 0.90 mmol). Sonicate for 5 minutes and cool to −5° C.

In a 250 mL Erlenmeyer flask, add a 40% aqueous solution of KOH (162 mL) followed by Et$_2$O (245 mL). Cool the biphasic mixture to −5° C. in an ice/saturated aqueous NaCl bath. Add N-nitroso-N-methylurea (36.1 g, 350 mmol) portion wise over 10 minutes. Stir for 15 minutes and place in a dry ice/acetone bath. Decant the ether layer into a graduated cylinder and add the Et$_2$O mixture (71 mL, ~10 equivalents of CH$_2$N$_2$) to the solution described above at −5° C. After 2 hours, filter the reaction contents though diatomaceous earth, dry over MgSO$_4$, and concentrate in vacuo to obtain the title compound (1.08 g, 58%). $^1$H NMR (d$_6$-DMSO) δ: −0.51 (dt, J=9.3, 5.7 Hz, 1H), 0.33-0.37 (m, 1H), 0.50-0.54 (m, 1H), 0.76-0.84 (m, 1H), 0.91 (t, J=7.4 Hz, 3H), 1.14 (s, 12H), 1.21-1.30 (m, 2H).

Alternate Procedure for Preparation 1

Add a 1M solution of lithium triethylborohydride in THF (41.3 mL, 41.3 mmol) to a solution of bis(pentamethylcyclopentadienyl)zirconium dichloride (11.1 g, 25.5 mmol) in THF (3.4 L) under nitrogen cooled at 0° C. Warm to RT and stir for 1 hour while protecting the flask from light with aluminum foil.

In a different flask cooled under nitrogen at −78° C., condense 1-but-1-yne (50.6 g, 936 mmol) and add pinacolborane (55.0 g, 425 mmol). Stir the resulting mixture at −78° C. for 30 minutes and add the contents of the first flask via cannula. Add TEA (5.93 mL, 42.6 mmol) and stir the reaction mixture while warming to RT for 20 hours. Quench the reaction by addition of a mixture of ice/water (1.5 L) via cannula, add EtOAc (300 mL), and stir at RT for 30 minutes. Separate the resulting layers and re-extract the aqueous phase with EtOAc (2×200 mL). Combine the organic extracts, dry over Na$_2$SO$_4$, filter, and concentrate in vacuo to afford 2-[(E)-but-1-enyl]-4,4,5,5-tetramethyl-1,3,2-dioxaborolane (53 g, 65%) as a yellow oil. GC-MS (m/z): 182 (M+).

Add a solution of diethylzinc in toluene (15% w/w, 550 mL, 611 mmol) to chloroiodomethane (55 mL, 755 mmol) at −20° C. over 10 minutes, and stir for 35 minutes. Drop wise add a solution of 2-[(E)-but-1-enyl]-4,4,5,5-tetramethyl-1,3,2-dioxaborolane (53 g, 277 mmol) in toluene (100 mL) over 20 minutes while keeping the internal temperature of the reaction at −20° C. Stir the mixture for 2 hours while warming to 0° C. Quench the reaction by a slow addition of saturated aqueous solution NH$_4$Cl (750 mL). Separate the organic layer and re-extract the aqueous phase with EtOAc (2×250 mL). Combine the organic extracts, dry over MgSO$_4$, filter, and evaporate to afford the title compound (48 g, 84%) as oil, suitable for use without additional purification. GC-MS (m/z): 180 (M−16).

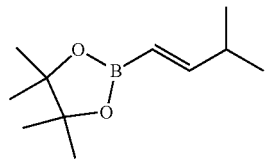

Add pinacol borane (9.5 ml, 64 mmol) drop wise over 5 minutes to ice cold 3-methylbut-1-yne (4.91 g, 72.0 mmol). Seal pressure vessel, warm to RT and stir 18 hours. Add bis(cyclopentadienyl)zirconium(IV) chloride hydride (2.0 g, 7.4 mmol) and TEA (1.1 mL, 7.9 mmol). Seal the pressure vessel, place in a 60° C. oil bath, and stir for 10 minutes. Cool the resulting red solution to RT for 2.5 hours. Dilute the reaction mixture with DCM (200 mL), wash with saturated aqueous NaHCO$_3$ (100 mL), saturated aqueous NaCl (50 mL), dry over MgSO$_4$, filter through a pad of silica gel (150 mL), rinse silica gel with DCM (700 mL), and concentrate in vacuo to afford the title compound (11.5 g, 82%). ES/MS (m/z): 196 (M+H). $^1$H NMR (CDCl$_3$) δ: 1.03 (d, J=6.7 Hz, 6H), 1.29 (s, 12H), 2.37 (m, 1H), 5.40 (dd, 1H), 6.64 (dd, 1H).

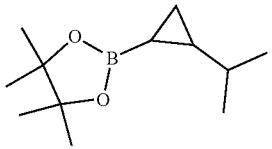

Portion wise, add N-nitroso-N-methylurea to an ice cold biphasic mixture of Et$_2$O (70 mL) and aqueous KOH (30.5 g, 435 mmol, 70 mL H$_2$O). Stir until solids dissolve (<5 minutes). Pipet the resulting diazomethane solution into a rapidly stirring ice cold suspension of Pd(OAc)$_2$ (237 mg, 1.05 mmol) and 4,4,5,5-tetramethyl-2-[(E)-3-methylbut-1-enyl]-1,3,2-dioxaborolane (4.00 g, 20.4 mmol) in Et$_2$O (70 mL). After complete addition, warm the reaction mixture to RT, filter through diatomaceous earth, and concentrate the filtrate in vacuo. Dissolve the resulting residue in DCM, filter through a plug of silica gel (25 g), and concentrate in vacuo to obtain the title compound (4.32 g, >99%). ES/MS (m/z): 210 (M+H). $^1$H NMR (CDCl$_3$) δ: −0.35 (m, 1H), 0.45 (m, 1H), 0.65 (m, 1H), 0.78 (m, 1H), 0.98 (m, 7H), 1.23 (s, 12H).

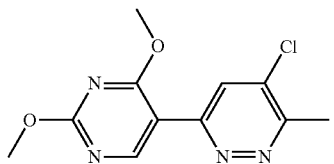

In a pressure vial, combine 2,4-dimethoxy-5-pyrimidinyl-boronic acid (6.75 g, 36.7 mmol), 4,6-dichloro-3-methyl-pyridazine (5.98 g, 36.7 mmol), [1,1'-bis (diphenylphosphino)ferrocene]dichloropalladium (II) (0.55 g, 0.73 mmol), Cs$_2$CO$_3$ (29.9 g, 91.8 mmol) in a 4:1 mixture of 1,4-dioxane/H$_2$O (151 mL). Evacuate the air and backfill with N2. Seal the vessel and heat at 70° C. for 3 hours. Filter the residue over diatomaceous earth and rinse with EtOAc. Wash the organic mixture with water followed by saturated aqueous NaCl, dry over MgSO$_4$, and evaporate to dryness. Purify the resulting black residue by chromatography over silica gel, using a 330 g REDISEP® column with a gradient of 0-30% DCM/(33% MeOH in DCM) over 15 minutes at a flow rate of 200 mL/minute, to afford the title compound (6.2 g, 63%) after evaporation of the chromatographic fractions. ES/MS (m/z) ($^{35}$Cl/$^{37}$Cl) 267/269 [M+1]$^+$ H NMR (d$_6$-DMSO) δ: 2.74 (s, 3H), 4.00 (s, 3H), 4.03 (s, 3H), 8.20 (s, 1H), 8.87 (s, 1H).

Alternate Procedure for Preparation 4

Pass a stream of nitrogen through a mixture of (2,4-dimethoxypyrimidin-5-yl)boronic acid (85 g, 439 mmol), 4,6-dichloro-3-methyl-pyridazine (75 g, 437 mmol) and Cs$_2$CO$_3$ (358 g, 1099 mmol) in 1,4-dioxane (1175 mL) and H$_2$O (340 mL) for 5 minutes. Add [1,1'-bis(diphenylphosphino)ferrocene]dichloropalladium(II) (6.6 g, 8.7 mmol,) and stir the resulting mixture at 75° C. for 16 hours. Cool the reaction to RT, filter the mixture through diatomaceous earth, and rinse the filter cake with EtOAc. Separate the resulting layers and wash the organic phase twice with saturated aqueous NaCl, dry over MgSO$_4$, filter, and concentrate in vacuo. Add water (500 mL) to the resulting residue, stir for 16 hours at RT, and filter the resulting solid. Wash collected solids with H$_2$O and dry under vacuum for 16 hours to obtain the desired compound (70 g, 54%) as a brown solid. ES/MS (m/z) ($^{35}$Cl/$^{37}$Cl) 267/269 [M+1]$^+$ The following examples may be prepared essentially as described in Preparation 4.

| Preparation # | Chemical Name | Chemical Structure | ES/MS (m/z) ($^{35}$Cl/$^{37}$Cl) |
|---|---|---|---|
| 5 | 5-(5-Chloropyridazin-3-yl)-2,4-dimethoxy-pryrimidine | 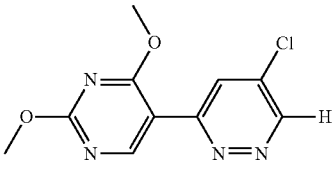 | 253/255 |

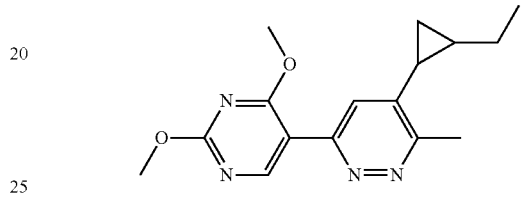

In a 20 mL pressure vial, add 4-chloro-6-(2,4-dimethoxy-pyrimidin-5-yl)-3-methyl-pyridazine (0.6 g, 2.0 mmol), bis(di-tert-butyl(4-dimethylaminophenyl)phosphine)dichloropalladium (II) (114 mg, 0.16 mmol), K$_2$CO$_3$ (0.69 g, 4.9 mmol), H$_2$O (2.25 mL) and racemic trans-2-[2-ethylcyclopropyl]-4,4,5,5-tetramethyl-1,3,2-dioxaborolane (0.66 g, 3.37 mmol). Evacuate the flask and backfill with N2. Seal the vessel and heat at 90° C. overnight. Filter the reaction mixture over diatomaceous earth, wash the organic layer with water followed by saturated aqueous NaCl, dry over MgSO$_4$, and concentrate in vacuo. Purify the resulting residue by reverse phase chromatography, using a 275 g REDISEP® Gold C18 column, eluting with a gradient of 30-50% 10 mM NH$_4$HCO$_3$/ACN over 20 minutes at a flow rate of 150 mL/minute, to afford the title compound, an essentially racemic mixture of isomers (475 mg, 70%), as a white solid, after evaporation of the chromatographic fractions.

The resulting isomers are subjected to purification by SFC (Column: PHENOMENEX® LUX® Cellulose-4, 4.6×150 mm; 40% MeOH/CO$_2$ isocratic; flow rate: 5 mL/minute, UV 250 nm) to afford 0.197 g of isomer 1: t$_R$=2.71 minutes (UV); and 0.195 g of isomer 2: t$_R$ 3.55 minutes (UV), both in >98% ee. ES/MS (m/z): 301 (M+H).

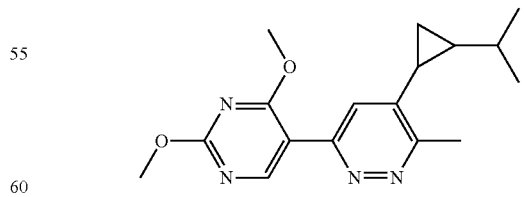

Combine 4-chloro-6-(2,4-dimethoxypyrimidin-5-yl)-3-methyl-pyridazine (1.97 g, 7.39 mmol), rac-trans-2-[2-isopropylcyclopropyl]-4,4,5,5-tetramethyl-1,3,2-dioxaborolane (3.32 g, 15.8 mmol), bis(di-tert-butyl(4-dimethylaminophenyl)phosphine) dichloropalladium (II) (1.35 g, 1.85 mmol), 1,4-dioxane (37 mL), and 1M aqueous Na₂CO₃ (18 mL, 18 mmol). Purge reaction vessel with N2 and heat to 90° C. for 18 hours. Cool to RT, dilute with EtOAc (150 mL), and separate layers. Wash the organic layer sequentially with 1M aqueous Na₂CO₃, saturated aqueous NaCl, dry over MgSO₄, filter, and concentrate the filtrate in vacuo. Purify the resulting residue by chromatography on silica, eluting with a gradient of 60-100% EtOAc/DCM, to afford the title compound as an essentially racemic mixture of isomers (1.48 g, 64%), after evaporation of the chromatographic fractions.

The isomers are subjected to purification by SFC (Column: PHENOMENEX® LUX® Cellulose-4, 4.6×150 mm; 40% MeOH/CO₂ isocratic; flow rate: 5 mL/minutes, UV 250 nm) to afford 647 mg isomer 1: $t_R$=2.56 min and 647 mg isomer 2: $t_R$=3.75 min. ES/MS (m/z): 315 (M+H).

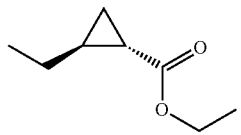

To a solution of ethyl 2-diethoxyphosphorylacetate (62.2 g, 277 mmol) in 1,4-dioxane (400 mL) cooled in an ice/water bath (inner temperature: 8° C.) add a 2.5M solution of nBuLi in hexanes (110 mL, 280 mmol) drop wise over 10 minutes. Remove the cooling bath and stir for 30 minutes at RT. Transfer the solution via cannula to a 1 L pressure vessel and add (2R)-2-ethyloxirane (20 g, 280 mmol). Stir the resulting mixture at 150° C. (50 psi pressure) for 17 hours. Cool the reaction to RT and add water (250 mL). Separate the organic phase and re-extract the aqueous phase with MTBE (2×200 mL). Combine organic extracts, wash with saturated aqueous NaCl (2×150 mL), dry over MgSO₄, and concentrate in vacuo to give crude title compound (49.1 g, quantitative) as a yellow oil, suitable for use without additional purification. GC-MS (m/z): 142 (M+), 97 (M−45).

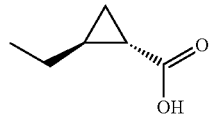

Stir a mixture of ethyl (1S,2S)-2-ethylcyclopropanecarboxylate (39.44 g, 277.4 mmol), 1,4-dioxane (315 mL) and a 25% aqueous solution of sodium hydroxide (315 mL) at 100° C. for 16 hours. Cool the mixture to RT, extract with MTBE (2×300 mL), and discard the organic phase. Acidify the aqueous phase with a 37% aqueous solution of HCl until pH~1-2, extract with MTBE (3×300 ml), separate the layers, wash the organic layer with saturated aqueous NaCl, dry over MgSO₄, and concentrate in vacuo to yield title compound (25.1 g, 75%) as amber oil. ¹H NMR (400 MHz, CDCl₃) δ: 0.79-0.85 (m, 1H), 1.00 (t, J=7.5 Hz, 3H), 1.22-1.26 (m, 1H), 1.32-1.42 (m, 3H), 1.43-1.48 (m, 1H), 9.0-12.0 (br-s, 1H).

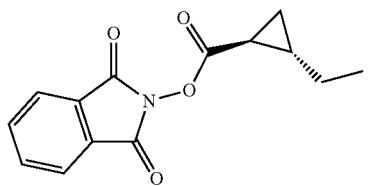 [SMILES: CC[C@H]1C[C@@H]1C(=O)ON1C(=O)c2ccccc2C1=O]

Stir a suspension of (1S,2S)-2-ethylcyclopropanecarboxylic acid (25.1 g, 209 mmol), 2-hydroxyisoindoline-1,3-dione (34.8 g, 209 mmol) and DMAP (2.58 g, 20.9 mmol) in DCM (360 mL) at 0° C. and add N,N'-diisopropylcarbodiimide (29.3 g, 230 mmol) drop wise. Remove the cooling bath and stir the reaction for 2 hours at RT. Filter the suspension through a silica gel plug, eluting with DCM. Evaporate the solvent and purify the resulting residue by chromatography over silica gel, eluting with 15% hexane/acetone, to afford title compound (51.56 g, 84%) as a pale yellow solid, after solvent removal from the chromatographic fractions. ES/MS (m/z): 260 (M+1).

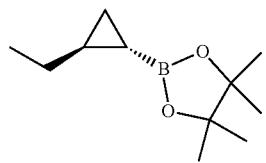

Pass a stream of N₂ through a solution of (1,3-dioxoisoindolin-2-yl) (1S,2S)-2-ethylcyclopropanecarboxylate (51 g, 173.1 mmol) and bis(pinacolato)diboron (87.9 g, 346 mmol) in EtOAc (1 L) for 5 minutes. Add ethyl isonicotinate (5.34 g, 35 mmol) and stir the mixture at 85° C. for 24 hours. Cool the resulting suspension, filter and discard the solids, and concentrate the brown filtrate under reduced pressure. Filter the resulting crude residue over a silica gel plug, eluting with 2% EtOAc/hexanes. Remove the solvent from the filtrate and repurify the resulting residue using chromatography over silica gel, eluting with 3% EtOAc/hexanes, to obtain the title compound (17.1 g, 49%) as colorless oil, after solvent removal from the chromatographic fractions. GC-MS (m/z): 180 (M−16).

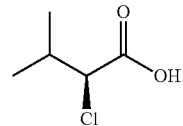

Cool a solution of L-valine (286 g, 2.44 mol) and a 5M aqueous solution of HCl (3.25 L, 16.3 mol) at 0° C. Add dropwise a 4M aqueous solution of NaNO₂ (1 L, 4 mol) over 2 hours, keeping the internal temperature below 5° C. Stir the reaction for 2 hours while warming to RT, and stir an additional 16 hours at RT. Portion wise over 30 minutes, add Na₂CO₃ (242 g, 2.28 mol). Extract the resulting solution with MTBE (3×1000 mL), wash the combined organic extracts with saturated aqueous NaCl (500 mL), dry the organic extracts over MgSO₄, and concentrate in vacuo. Purify the resulting residue by vacuum distillation (15 mbar/140° C.) to afford the title compound (248 g, 68%) as oil. ¹H NMR (400 MHz, CDCl₃) δ: 1.1 (dt, J=6.6, 2.6 Hz, 6H), 2.34-2.42 (m, 1H), 4.19-4.23 (m, 1H), 10.0-12.0 (br-s, 1H).

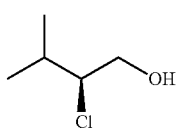

Cool a solution of (2S)-2-chloro-3-methyl-butanoic acid (137 g, 1 mol) in 2-methyltetrahydrofuran (500 mL) to 0° C. Add a 2.3M solution of LAH in methyltetrahydrofuran (480 mL, 1.1 mol) drop wise over 2.5 hours, keeping the internal temperature below 10° C. Warm to RT and stir the mixture for 1 hour at RT and 1 hour at 50° C. Cool the reaction to 0° C. and sequentially and slowly add $H_2O$ (1.48 mL), 15% aqueous solution of NaOH (1.48 mL) and $H_2O$ (4.46 mL). Allow the mixture to warm to RT, filter through a bed of diatomaceous earth, and evaporate the solvent in vacuo to afford title compound (110 g, 81%) as colorless oil. $^1H$ NMR (400 MHz, $CDCl_3$) δ: 0.97-1.1 (m, 6H), 1.94-2.18 (m, 1H), 2.60-3.09 (br-s, 1H), 3.71-3.78 (m, 1H), 3.80-3.85 (m, 1H), 3.90-3.96 (m, 1H).

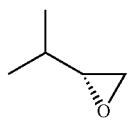

Cool a solution of KOH (195 g, 3.48 mol) in $H_2O$ (195 mL) to 0° C. and add neat (2S)-2-chloro-3-methyl-butan-1-ol (110 g, 801 mmol) over 20 minutes while keeping the internal temperature below 5° C. Allow the reaction mixture to warm to RT. Purify the reaction mixture by vacuum distillation at 100 mbar, warming from 23° C. to 50° C., to afford title compound (47 g, 64%) as colorless oil. $^1H$ NMR (400 MHz, $CDCl_3$) δ: 0.98 (d, J=6.9 Hz, 3H), 1.05 (d, J=6.9 Hz, 3H), 1.51 (o, J=6.9 Hz, 1H), 2.52-2.54 (m, 1H), 2.70-2.75 (m, 2H).

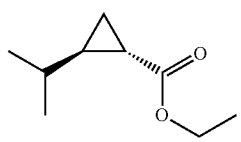

Add a 2.5M solution of nBuLi in hexanes (310 mL, 780 mmol) to a solution of ethyl 2-diethoxyphosphorylacetate (153 mL, 772 mmol) in 1,4-dioxane (870 mL) cooled in an ice/water bath (inner temperature: 8° C.) dropwise over 25 minutes. Warm to RT and stir for 40 minutes. Transfer the solution via cannula to a 3 L pressure vessel and add (2R)-2-isopropyloxirane (70 g, 772 mmol) in 1,4-dioxane (180 mL). Stir the reaction mixture at 150° C. at 50 psi pressure for 14 hours. Cool the reaction mixture to RT and add $H_2O$ (700 mL). Separate the layers and re-extract aqueous phase with MTBE (2×500 mL). Combine the organic phases, wash with saturated aqueous NaCl (2×350 mL), dry over $MgSO_4$, and concentrate in vacuo to obtain the crude title compound (107.7 g, >99%) as yellow oil, suitable for subsequent use without further purification. GC-MS (m/z): 156 (M+).

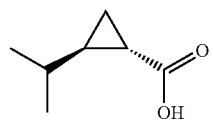

Stir a mixture of ethyl (1S,2R)-2-isopropylcyclopropanecarboxylate (107.7 g, 482.6 mmol) in 1,4-dioxane (800 mL) containing a 25% aqueous solution of NaOH (800 mL) at 100° C. for 7 hours. Cool the mixture to RT, add water (300 mL), extract with MTBE (2×500 mL), and discard the organic phase. Acidify the aqueous phase with a 37% aqueous solution of HCl (approximately 500 mL) until pH~1-2.

Extract the acidified aqueous mixture with MTBE (2×600 mL), wash the organic layer with saturated aqueous NaCl, dry over $MgSO_4$, and concentrate in vacuo, to yield the title compound (54.2 g, 75%) as amber oil. $^1H$ NMR (400 MHz, $CDCl_3$) δ: 0.81-0.86 (m, 1H), 1.01 (dd, J=5.9, 3.7 Hz, 6H), 1.04-1.13 (m, 1H), 1.20-1.24 (m, 1H), 1.28-1.37 (m, 1H), 1.39-1.44 (m, 1H).

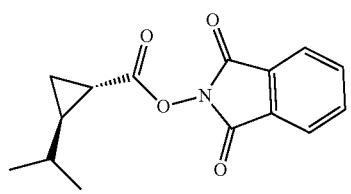 [SMILES: CC(C)[C@H]1C[C@@H]1C(=O)ON1C(=O)c2ccccc2C1=O]

Stir a suspension of (1S,2R)-2-isopropylcyclopropanecarboxylic acid (54.2 g, 359 mmol), 2-hydroxyisoindoline-1,3-dione (59.8 g, 359 mmol) and DMAP (4.44 g, 35.9 mmol) in DCM (690 mL) at 0° C. Add N,N'-diisopropylcarbodiimide (50.4 g, 395 mmol) drop wise, warm to RT, and stir the resulting reaction mixture for 2 hours at RT. Add $H_2O$ (600 mL) and separate the phases. Extract the aqueous phase with DCM (2×300 mL), combine the organic phases, dry over $MgSO_4$, filter, and evaporate. Purify the resulting solid residue by chromatography on silica, eluting with 100% DCM, to afford the title compound (96 g, 88%) as pale yellow solid, after evaporation of the chromatographic fractions. ES/MS (m/z): 274 (M+1).

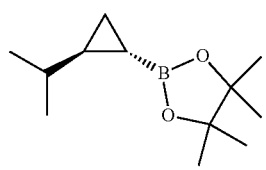

Pass a stream of nitrogen through a solution of (1,3-dioxoisoindolin-2-yl) (1S,2S)-2-isopropylcyclopropanecarboxylate (96 g, 316 mmol) and bis(pinacolato)diboron (160 g, 630 mmol) in EtOAc (480 mL) for 15 minutes. Stir the mixture at 85° C. and add ethyl isonicotinate (24.38 g, 157 mmol) drop wise over 10 minutes. Stir the resulting mixture at 85° C. for 16 hours. Cool the resulting suspension, filter and discard the solids, and evaporate the brown filtrate under reduced pressure. Filter the crude residue over a silica gel plug, eluting with 2% EtOAc/hexanes. Remove the solvent from the filtrate and repurify the resulting residue using chromatography over silica gel, eluting with 3% EtOAc/ hexanes, to obtain the title compound (25.3 g, 38%) as colorless oil, after solvent removal from the chromatographic fractions. ¹H NMR (400 MHz, CDCl₃): −0.33-−0.38 (m, 1H), 0.42-0.47 (m, 1H), 0.63-0.67 (m, 1H), 0.75-0.82 (m, 1H), 0.89-1.02 (m, 1H), 0.98 (m, 6H), 1.24 (s, 12H).

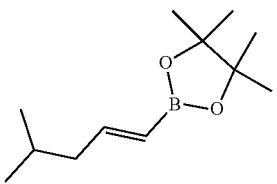

Dissolve [(E)-4-methylpent-1-enyl]boronic acid (0.975 g, 7.62 mmol) and pinacol (1.11 g, 9.14 mmol) in dry DCM (9.7 mL). Add MgSO₄ (0.7313 g, 6.05 mmol) and stir at room temperature for 3 days. Filter insoluble solids and remove solvent under reduce pressure to afford title compound as a clear oil (1.6 g, 100%). 1H NMR (400.13 MHz, DMSO): 0.86 (d, J=6.6 Hz, 6H), 1.08 (s, 6H), 1.19 (s, 12H), 1.62-1.72 (m, 1H), 2.01 (td, J=6.9, 1.4 Hz, 2H), 3.92 (s, 1H), 5.31 (dt, J=17.9, 1.3 Hz, 1H), 6.47 (dt, J=17.9, 6.9 Hz, 1H).

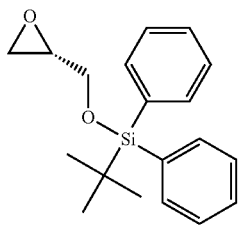 [SMILES: CC(C)(C)[Si](OC[C@@H]1CO1)(c1ccccc1)c1ccccc1]

To an ice cold solution of [(2R)-oxiran-2-yl]methanol (15.0 g, 202.6 mmol) in DMF (135 mL) add imidazole (33.34 g, 489.8 mmol) and stir for 15 minutes. Add tert-butyl-chloro-diphenyl-silane (77 mL, 302.5 mmol,) dropwise over 30 min and stir overnight to room temperature. Dilute with hexanes (1 L), ether (500 ml) and water (1 L). Separate layers and extract aqueous layer with ether (2×1 L). Combine organics and wash with water (3×750 mL), NaHCO₃ sat, saturated aqueous NaCl, and dry over MgSO₄. Evaporate solvent under reduce pressure. Purify by silica gel chromatography: eluent 0-10% EtOAc in hexanes to afford title compound (11.77 g, 18%) as an oil, after solvent removal from the chromatographic fraction. 1H NMR (400.13 MHz, CDCl₃): 1.08 (s, 9H), 2.64 (dd, J=2.6, 5.1 Hz, 1H), 2.77 (t, J=4.6 Hz, 1H), 3.15 (quintet, J=3.5 Hz, 1H), 3.73 (dd, J=4.7, 11.8 Hz, 1H), 3.88 (dd, J=3.2, 11.9 Hz, 1H), 7.40-7.48 (m, 6H), 7.71 (m, 4H).

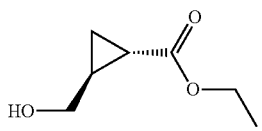

Slowly add triethyl phosphonoacetate (7.5 mL, 38 mmol) to a suspension of sodium tert-butoxide (3.67 g, 37.82 mmol) in 1,4-dioxane (40 mL) at room temperature. After 1 hour add tert-butyl-[[(2S)-oxiran-2-yl]methoxy]-diphenyl-silane (11.77 g, 33.76 mmol) and heat at 140° C. overnight in a sealed pressure vessel. Add additional triethyl phosphonoacetate (2 mL) and heat at 160° C. for an hour. Allow the mixture to cool down and dilute with DCM (300 ml) and water (150 mL). Separate layers, extract aqueous layer with DCM (3×150 mL). Combine organics and wash with saturated aqueous NaHCO₃, saturated aqueous NaCl and dry over MgSO₄. Filter through diatomaceous earth and evaporate solvent under reduce pressure to afford ethyl (1S,2S)-2-[[tert-butyl(diphenyl)silyl] oxymethyl]cyclopropanecarboxylate (18.45 g) as an oil. Dissolve in THF (75 mL) and add tetrabutylammonium fluoride (1 M THF, 67 mL, 67 mmol, 1.0 M) at room temperature. Stir for 48 hours and remove solvent at 130 mbar and 30° C. Purify by silica gel chromatography, eluent: 0-50% EtOAc in hexanes to isolate title compound (3.35 g, 62%) as an oil, after solvent removal from the chromatographic fraction. ES/MS (m/z): 142 (M+1). 1H NMR (400.13 MHz, CDCl₃): 0.90-0.86 (m, 1H), 1.23 (dd, J=4.5, 8.9 Hz, 1H), 1.28 (t, J=7.2 Hz, 4H), 1.56-1.60 (m, 1H), 1.69-1.77 (m, 2H), 2.06 (s, 2H), 3.50 (dd, J=6.9, 11.5 Hz, 1H), 3.64 (dd, J=6.0, 11.4 Hz, 1H), 4.14 (qd, J=7.1, 2.9 Hz, 3H).

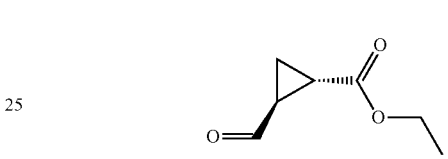

To an ice cooled solution of ethyl (1S,2S)-2-(hydroxymethyl)cyclopropanecarboxylate (12.25 g, 84.9 mmol,) in DCM (425 mL), add pyridinium chlorochromate (26.09 g, 118.6 mmol) in one portion. After 30 minutes remove ice bath and stir at room temperature for 4 hours. Add water (200 mL) and filter through diatomaceous earth. Rinse with additional water (100 mL) and DCM (800 mL). Suspend the diatomaceous earth cake in DCM and filter. Repeat this operation twice. Combine organics, separate the water layer, and filter the organics through a pad of silica. Rinse with additional DCM and evaporate solvent under reduce pressure to afford the title compound (11.0 g, 91%) as an oil. 1H NMR (400.13 MHz, CDCl₃): 1.30 (t, J=7.3 Hz, 3H), 1.57-1.50 (m, 1H), 1.60-1.65 (m, 2H), 2.26-2.30 (m, 1H), 2.45 (td, J=9.0, 4.2 Hz, 1H), 4.13-4.22 (m, 3H), 9.32 (d, J=4.2 Hz, 1H).

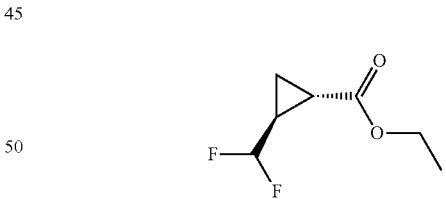

Add diethylaminosulfur trifluoride (24 mL, 172.3 mmol) to an ice cold solution of ethyl (1S,2S)-2-formylcyclopropanecarboxylate (11.00 g, 77.38 mmol) in DCM (220 mL) over 3 minutes. After 1 hour remove from ice bath and stir at room temperature for 2 hours. Add diethylaminosulfur trifluoride (3.5 mL) and stir for additional hour. Cool the mixture in an ice bath and pour carefully into saturated aqueous NaHCO₃. Separate layers and extract aqueous layer with DCM (2×50 mL).

Combine organics and dry over MgSO₄. Filter the sample through a small pad of silica and evaporate solvent under reduce pressure (250 mbar and 30° C.) to provide the title compound (11.10 g, 87%) as an oil. 1H NMR (400.13 MHz, CDCl₃): 1.14-1.19 (m, 1H), 1.29 (m, 1H), 1.30 (t, J=7.2 Hz, 3H), 1.97-1.89 (m, 2H), 4.22 (q, J=7.2 Hz, 3H), 5.79 (td, JH-F=56.8 Hz, J=3.6 Hz, 1H).

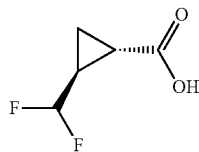

Add 1N NaOH (75 mL) to a solution of ethyl (1S,2S)-2-(difluoromethyl) cyclopropanecarboxylate (11.10 g, 67.62 mmol) in MeOH (75 mL) and stir at RT overnight. Add DCM (70 mL) and separate the layers. Extract aqueous layer with DCM (70 mL). Cool aqueous layer in an ice bath and adjust pH to 1 by addition of 35% HCl. Add DCM (50 mL) and separate the two layers. Extract aqueous layer with DCM. Combine organics, dry over MgSO₄, and evaporate solvent under reduce pressure (200 mbar, 30° C.) to afford the title compound (6.25 g, 68%) as an oil. 1H NMR (400.13 MHz, CDCl₃): 1.26 (dt, J=8.4, 5.9 Hz, 1H), 1.34-1.39 (m, 1H), 1.92-1.96 (m, 1H), 2.01-2.07 (m, 1H), 5.82 (td, JH-F=59 Hz, J=3.2 Hz, 1H).

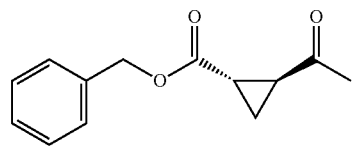 [SMILES: CC(=O)[C@H]1C[C@@H]1C(=O)OCc1ccccc1]

Add K₂CO₃ (36.2 g, 261.93 mmol) to a mixture of benzylbromoacetate (40 g, 174.618 mmol), methyl vinyl ketone (43 mL, 523.85 mmol), 1,4-diazabicyclo[2.2.2]octane (2.3 g, 20.9 mmol) in acetonitrile (400 mL). Stir under N2 at 80° C. overnight. Allow to cool down, filter, and evaporate solvent under reduce pressure. Purify by silica gel chromatography, eluent 0-50% EtOAc/hexane to afford the title compound (13.4 g, 35%), after solvent removal from the chromatographic fractions. 1H NMR (400.13 MHz, d₆-DMSO): 1.33-1.39 (m, 2H), 2.08-2.13 (m, 1H), 2.24 (s, 3H), 2.54-2.59 (m, 2H), 5.13 (s, 2H), 7.39-7.37 (m, 6H).

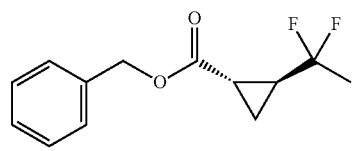 [SMILES: CC(F)(F)[C@H]1C[C@@H]1C(=O)OCc1ccccc1]

Add EtOH (0.05 eq) to a mixture of trans-benzyl-2-acetylcyclopropanecarboxylate (2.76 g, 12.6 mmol) and bis(2-methoxyethyl)aminosulfur trifluoride (23.2 mL, 126 mmol) at 0° C. Allow to warm to room temperature and heat at 50° C. for 40 hours. Dilute with DCM and cool the mixture in an ice bath for the slow addition of saturated NaHCO₃ aqueous solution. Separate the layers and extract the aqueous layer with DCM (2×100 mL). Combine the organics and dry over anhydrous Na₂SO₄. Evaporate solvent under reduced pressure. Purify by silica gel chromatography, eluent: 10% MTBE/hexane to afford the title compound (2.30 g, 76%) as a colorless oil, after solvent removal from the chromatographic fractions. 1H NMR (400.13 MHz, d₆-DMSO): 1.19 (t, J=7.5 Hz, 2H), 1.67 (t, J H-F=16 Hz, 3H), 1.93-1.98 (m, 1H), 2.00-2.08 (m, 1H), 5.13 (s, 2H), 7.38-7.40 (m, 5H).

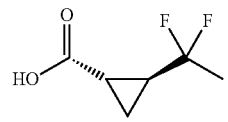

Add 10% Pd/C (1.53 g, 14.4 mmol) to a solution of trans-benzyl-2-(1,1-difluoroethyl)cyclopropanecarboxylate (6.56 g, 27.3 mmol) in EtOAc (136 mL, 0.2 M). Stir at RT under H₂ using a balloon for 3 hours. Filter through diatomaceous earth and rinse with EtOAc. Evaporate solvent under reduced pressure to afford title compound (4.03 g, 98%) as a colorless oil. 1H NMR (400.13 MHz, d₆-DMSO): 1.10 (t, J=7.4 Hz, 2H), 1.66 (t, J H-F=18.4 Hz, 3H), 1.72-1.77 (m, 1H), 1.96-1.99 (m, 1H), 12.49 (s, 1H).

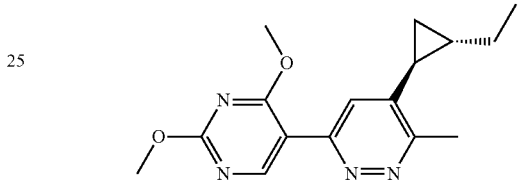

Degas a mixture of 4-chloro-6-(2,4-dimethoxypyrimidin-5-yl)-3-methyl-pyridazine (16 g, 54.0 mmol), 2-[(1S,2S)-2-ethylcyclopropyl]-4,4,5,5-tetramethyl-1,3,2-dioxaborolane (17 g, 83.22 mmol), a 2 M aqueous solution of Na₂CO₃ (70 mL, 140 mmol) and 1,4-dioxane (290 mL) by bubbling N2 through the mixture for 10 minutes. Add bis(di-tert-butyl(4-dimethylaminophenyl)phosphine)dichloropalladium(II) (2.0 g, 2.74 mmol) and stir the resulting mixture at 90° C. for 16 hours. Cool the reaction mixture to RT, dilute with H₂O, and extract with EtOAc. Separate the resulting phases, dry the organic phase over anhydrous MgSO₄, and concentrate in vacuo. Purify the resulting residue by chromatography over silica, eluting with a gradient of 60-100% hexanes/EtOAc, to obtain the title compound (12.95 g, 77%) as an amber oil, after solvent removal from the chromatographic fractions. The oil solidifies on standing at RT to an off-white solid. ES/MS (m/z): 301 (M+1).

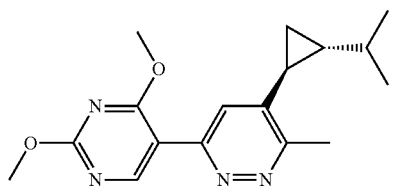 [SMILES: COc1ncc(-c2cc([C@H]3C[C@@H]3C(C)C)c(C)nn2)c(OC)n1]

Mix 4-chloro-6-(2,4-dimethoxypyrimidin-5-yl)-3-methyl-pyridazine (19.1 g, 70.6 mmol), K₃PO₄ (45.9 g, 212 mmol), 1,4-dioxane (300 mL) and H₂O (75 mL) and degas the mixture with N2 for 10 minutes. Add [1,1'-bis(diphenylphosphino)ferrocene]dichloro palladium(II) (7.98 g 10.6 mmol). Bubble with nitrogen for 2 additional minutes and add 2-[(1 S,2S)-2-isopropylcyclopropyl]-4,4,5,5-tetramethyl-1,3,2-dioxaborolane (22.2 g, 106 mmol) in one portion. Stir the resulting mixture at 80° C. for 16 hours. Cool the reaction to RT, add H₂O, and extract with EtOAc. Separate the organic layer, dry over anhydrous MgSO₄, and concentrate under reduced pressure. Purify the resulting residue by chromatography over silica, eluting with 85% hexanes/EtOAc, to isolate title compound (21.5 g, 92%) as an amber oil, after solvent removal from the chromatographic fraction. The oil solidifies on standing at RT to an off-white solid. ES/MS (m/z): 315 (M+1).

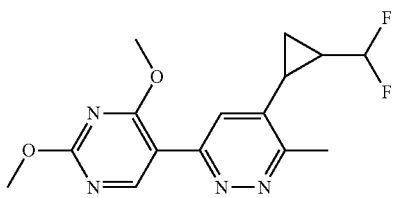 [SMILES: COc1ncc(-c2cc(C3CC3C(F)F)c(C)nn2)c(OC)n1]

Add dimethylzinc (2 M in toluene, 1.5 mL, 3.0 mmol) to a degassed suspension of 3-chloro-4-[(1S,2S)-2-(difluoromethyl)cyclopropyl]-6-(2,4-dimethoxypyrimidin-5-yl)pyridazine (502 mg, 1.46 mmol) and 1,1'-bis(diphenylphosphino)ferrocene-palladium (II)dichloride (53 mg, 0.07 mmol) in THF (6 mL). Heat at 60° C. in a sealed vial for 2 hours. Allow to cool down to room temperature. Add saturated aqeuous NH₄Cl solution and extract with DCM (3×). Combine organics, dry over anhydrous MgSO₄ and remove solvent under reduced pressure. Purify by silica gel chromatography, eluent: EtOAc, to afford title compound as a yellow residue (433 mg, 91.8%), after solvent removal from the chromatographic fractions. ES/MS (m/z): 323 (M+1).

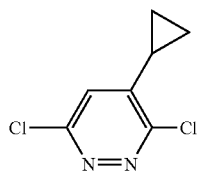 [SMILES: Clc1cc(C2CC2)c(Cl)nn1]

To a suspension of 3,6-dichloropyridazine (10.00 g, 67.12 mmol) in water (300 mL) add 10 mL of concentrated H₂SO₄ and cyclopropanecarboxylic acid (5.85 mL, 73.7 mmol), heat at 70° C. and de-gassed with N₂. Add a solution of AgNO₃ (2.28 g, 13.4 mmol) in 10 mL of H₂O over 30 seconds followed by drop wise addition of a solution of (NH₄)₂S208 (46 g, 201.577 mmol) in 150 mL of H₂O over 30 minutes. After an hour allow the mixture to cooled to RT and poured onto ice, adjust pH to 9 by addition of concentrated NH₄OH. Dilute with EtOAc and separate the organic layer. Extract the aqueous layer with additional EtOAc. Combine the organics, dry over anhydrous Na₂SO₄ and evaporate solvent under reduced pressure. Purify by reverse phase chromatography (C18 Gold 415 g, gradient 25-100% ACN in 10 mM ammonium bicarbonate; 150 mL/min, for 30 min) to isolate title compound (6.83 g, 54%) as a white solid, after solvent removal from the chromatographic fractions. ES/MS (m/z): ($^{35}$Cl/$^{37}$Cl) 189/191.

The following examples may be prepared essentially as described in Preparation 22.

| Preparation # | Chemical Name | Chemical Structure | ES/MS (m/z) ($^{35}$Cl/$^{37}$Cl) |
|---|---|---|---|
| 32 | Rac-trans-3,6-dichloro-4-(2-isopropylcyclopropyl)pyridazine | 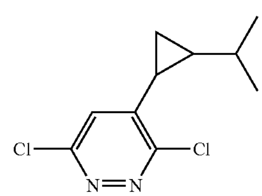 | 231/233 |
| 33 | Rac-trans-3,6-dichloro-4-(2-ethylcyclopropyl)pyridazine | 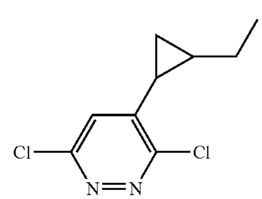 | 217/219 |
| 34 | 3,6-Dichloro-4-(2,2-difluorocyclopropyl)pyridazine | 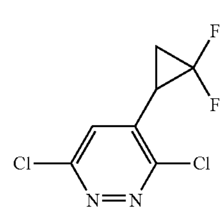 [SMILES: FC1(F)CC1c1cc(Cl)nnc1Cl] | 225/227 |

-continued

| Preparation # | Chemical Name | Chemical Structure | ES/MS (m/z) ($^{35}Cl/^{37}Cl$) |
|---|---|---|---|
| 35 | Rac-trans-3,6-dichloro-4-[2-(difluoromethyl)cyclopropyl]pyridazine | 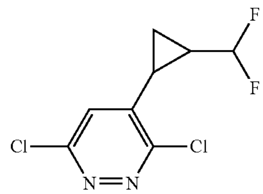 [SMILES: FC(F)C1CC1c1cc(Cl)nnc1Cl] | 239/241 |
| 36 | Rac-trans-3,6-dichloro-4-[2-(1,1-difluoroethyl)cyclopropyl]pyridazine | 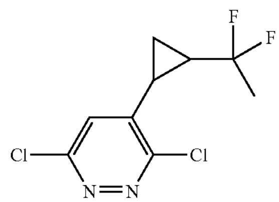 | 253/255 |
| 37 | 3,6-Dichloro-4-cyclobutyl-pyridazine | 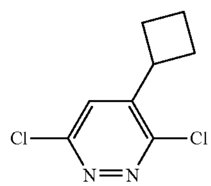 [SMILES: Clc1cc(C2CCC2)c(Cl)nn1] | 203/205 |
| 38 | 3,6-Dichloro-4-(3,3-dimethylcyclobutyl)pyridazine | 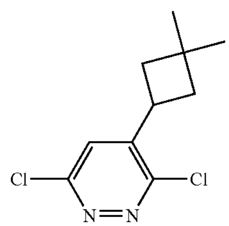 | 231/233 |
| 39 | 3,6-Dichloro-4-(3,3-difluorocyclobutyl)pyridazine | 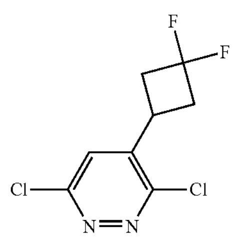 [SMILES: FC1(F)CC(c2cc(Cl)nnc2Cl)C1] | 239/241 |
| 40 | 3,6-Dichloro-4-cyclopentyl-pyridazine | 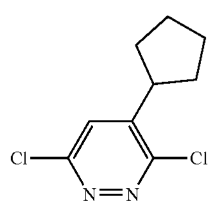 [SMILES: Clc1cc(C2CCCC2)c(Cl)nn1] | 217/219 |
| 41 | 3,6-Dichloro-4-(3,3-difluorocyclopentyl)pyridazine | 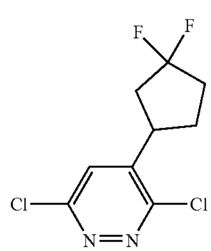 [SMILES: FC1(F)CCC(c2cc(Cl)nnc2Cl)C1] | 253/255 |

| Preparation # | Chemical Name | Chemical Structure | ES/MS (m/z) ($^{35}Cl/^{37}Cl$) |
|---|---|---|---|
| 42 | 3,6-Dichloro-4-cyclohexyl-pyridazine | 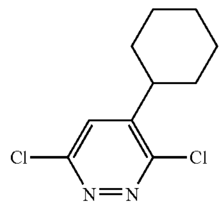 [SMILES: Clc1cc(C2CCCCC2)c(Cl)nn1] | 231/233 |

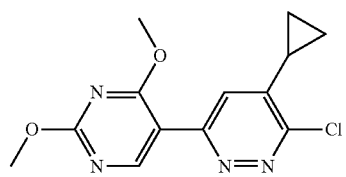 [SMILES: COc1ncc(-c2cc(C3CC3)c(Cl)nn2)c(OC)n1]

Mix (2,4-dimethoxypyrimidin-5-yl)boronic acid (4.60 g, 25.0 mmol), 3,6-dichloro-4-cyclopropyl-pyridazine (5.2 g, 28 mmol) and K$_2$CO$_3$ (4.4 g, 32 mmol), 1,4-dioxane (125 mL) and H$_2$O (42 mL) and degas the mixture with N$_2$ for 10 minutes. Add [1,1'-bis(diphenylphosphino)ferrocene]dichloro palladium(II) dichloromethane complex (1.5 g, 1.8 mmol) and degas further with N$_2$. Stir the resulting mixture at 60° C. for 1 hour. Cool the reaction to RT, add H$_2$O, and extract with EtOAc. Separate the organic layer. Extract the aqueous layer with additional EtOAc. Combine the organics, dry over anhydrous Na$_2$SO$_4$ and evaporate the solvent under reduced pressure. Purify the resulting residue by chromatography over silica, eluting with 70% hexanes/(3:2 Acetone:DCM), to isolate title compound (2.4 g, 33%) as light yellow solid, after solvent removal from the chromatographic fractions. ES/MS (m/z): ($^{35}Cl/^{37}Cl$) 293/295 [M+1]$^+$ The following examples may be prepared essentially as described in Preparation 6.

| Preparation # | Chemical Name | Structure | ES/MS (m/z) ($^{35}Cl/^{37}Cl$) |
|---|---|---|---|
| 44 | Rac-trans-3-chloro-6-(2,4-dimethoxypyrimidin-5-yl)-4-(2-isopropylcyclopropyl)pyridazine | 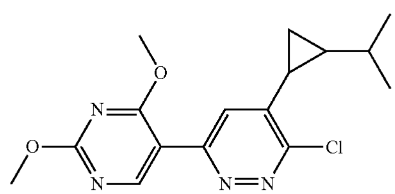 | 335/337 |
| 45 | Rac-3-chloro-4-(2,2-difluorocyclopropyl)-6-(2,4-dimethoxypyrimidin-5-yl)pyridazine | 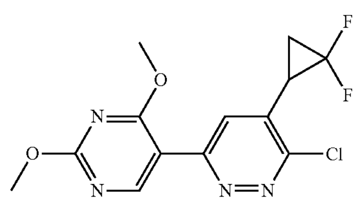 [SMILES: COc1ncc(-c2cc(C3CC3(F)F)c(Cl)nn2)c(OC)n1] | 329/331 |
| 46 | Rac-trans-3-chloro-4-[2-(difluoromethyl)cyclopropyl]-6-(2,4-dimethoxypyrimidin-5-yl)pyridazine | 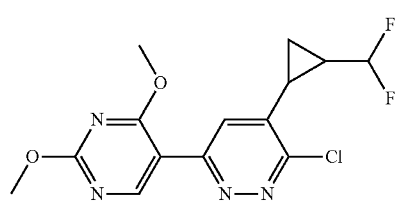 [SMILES: COc1ncc(-c2cc(C3CC3C(F)F)c(Cl)nn2)c(OC)n1] | 343/345 |
| 47 | Rac-trans-3-chloro-4-[2-(1,1-difluoroethyl)cyclopropyl]-6-(2,4-dimethoxypyrimidin-5-yl)pyridazine | 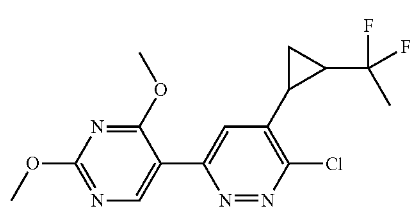 [SMILES: COc1ncc(-c2cc(C3CC3C(C)(F)F)c(Cl)nn2)c(OC)n1] | 357/359 |

-continued

| Preparation # | Chemical Name | Structure | ES/MS (m/z) ($^{35}Cl/^{37}Cl$) |
|---|---|---|---|
| 48 | 3-Chloro-4-cyclobutyl-6-(2,4-dimethoxypyrimidin-5-yl)pyridazine | 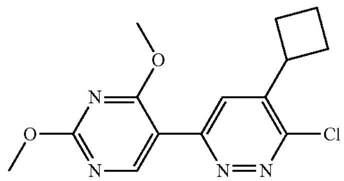 [SMILES: COc1ncc(-c2cc(C3CCC3)c(Cl)nn2)c(OC)n1] | 307/309 |
| 49 | 3-Chloro-6-(2,4-dimethoxypyrimidin-5-yl)-4-(3,3-dimethylcyclobutyl)pyridazine | 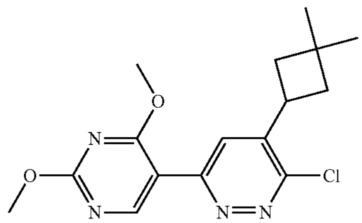 | 335/337 |
| 50 | 3-Chloro-4-(3,3-difluorocyclobutyl)-6-(2,4-dimethoxypyrimidin-5-yl)pyridazine | 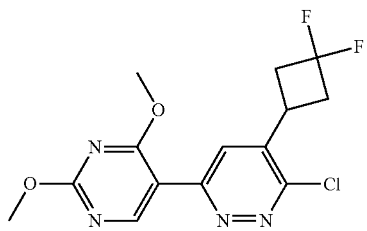 [SMILES: COc1ncc(-c2cc(C3CC(F)(F)C3)c(Cl)nn2)c(OC)n1] | 343/345 |
| 51 | 3-Chloro-4-cyclopentyl-6-(2,4-dimethoxypyrimidin-5-yl)pyridazine | 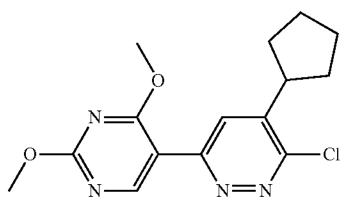 [SMILES: COc1ncc(-c2cc(C3CCCC3)c(Cl)nn2)c(OC)n1] | 321/323 |

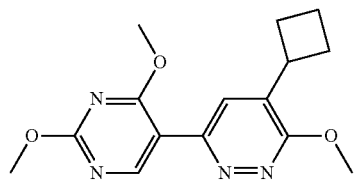

3-Chloro-4-cyclobutyl-6-(2,4-dimethoxypyrimidin-5-yl)pyridazin obtained following preparations 21 and 33 from cyclobutylcarboxylic acid.

Add 3-Chloro-4-cyclobutyl-6-(2,4-dimethoxypyrimidin-5-yl)pyridazine (0.42 g, 1.4 mmol) to a solution of NaOMe prepared by dissolving Na (0.16 g, 6.8 mmol) in MeOH (12 mL). Heat the mixture in a capped vial at 60° C. overnight. Allow the mixture to cool to RT, add 50% saturated aqueous NaCl and extract with DCM (3×). Combine organics and dry over anhydrous $MgSO_4$. Remove solvent under reduce pressure to afford title compound (0.38 g, 93%) as a white solid. ES/MS (m/z): 303 (M+1).

The following examples may be prepared essentially as described in Preparation 52.

| Preparation # | Chemical Name | Structure | ES/MS (m/z) (M + H) |
|---|---|---|---|
| 53 | 4-Cyclopropyl-6-(2,4-dimethoxypyrimidin-5-yl)-3-methoxy-pyridazine | 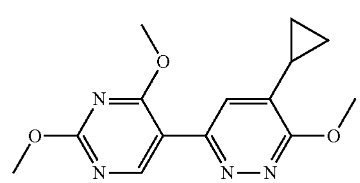 | 289 |

-continued

| Preparation # | Chemical Name | Structure | ES/MS (m/z) (M + H) |
|---|---|---|---|
| 54 | 5-[5-(3,3-Dimethylcyclobutyl)-6-methoxy-pyridazin-3-yl]-2,4-dimethoxy-pyrimidine | 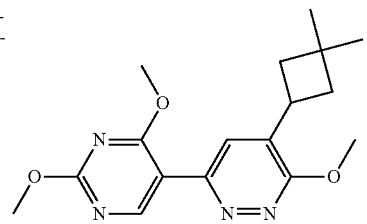 | 331 |
| 55 | 4-(3,3-Difluorocyclobutyl)-6-(2,4-dimethoxypyrimidin-5-yl)-3-methoxy-pyridazine | 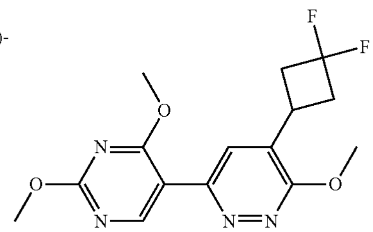 | 339 |
| 56 | 4-(3,3-Difluorocyclopentyl)-6-(2,4-dimethoxypyrimidin-5-yl)-3-methoxy-pyridazine (Isomer 1) | 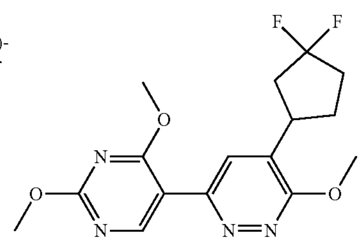 | 353 |
| 57 | 4-(3,3-Difluorocyclopentyl)-6-(2,4-dimethoxypyrimidin-5-yl)-3-methoxy-pyridazine (Isomer 2) | 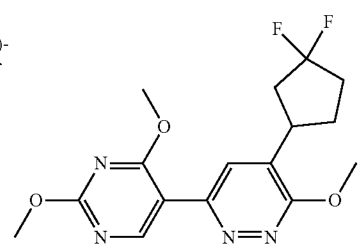 | 353 |
| 58 | 4-Cyclohexyl-6-(2,4-dimethoxypyrimidin-5-yl)-3-methoxy-pyridazine | 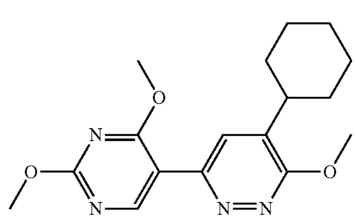 [SMILES: COc1ncc(-c2cc(C3CCCCC3)c(OC)nn2)c(OC)n1] | 331 |

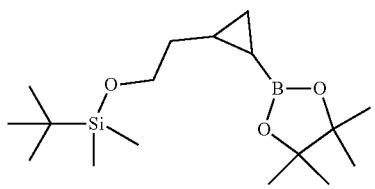 [SMILES: CC1(C)OB(C2CC2CCO[Si](C)(C)C(C)(C)C)OC1(C)C]

May be prepared essentially as described in Preparation 3 from commercially available tert-butyl-dimethyl-[(E)-4-(4,5,5-tetramethyl-1,3,2-dioxaborolan-2-yl)but-3-enoxy]silane. 1H NMR (400.13 MHz, CDCl3): 3.70-3.66 (m, 2H), 1.51-1.38 (m, 2H), 1.23 (s, 12H), 1.04-0.96 (m, 1H), 0.91 (s, 9H), 0.71-0.67 (m, 1H), 0.46-0.41 (m, 1H), 0.07 (s, 6H), −0.38 (dt, J=9.3, 5.8 Hz, 1H).

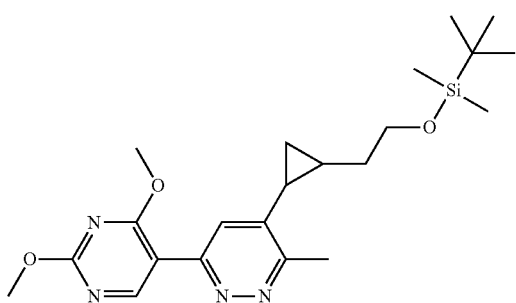 [SMILES: COc1ncc(-c2cc(C3CC3CCO[Si](C)(C)C(C)(C)C)c(C)nn2)c(OC)n1]

May be prepared essentially as described in Preparation 4. ES/MS (m/z): 417 (M+1).

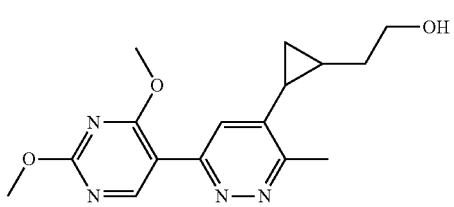 [SMILES: COc1ncc(-c2cc(C3CC3CCO)c(C)nn2)c(OC)n1]

Add tetrabutylammonium fluoride (5 mL, 5 mmol, 1 M in THF) and trans-tert-butyl-dimethyl-[2-[2-[6-(2,4-dimethoxypyrimidin-5-yl)-3-methyl-pyridazin-4-yl]cyclopropyl]ethoxy]silane (1.15 g, 8.9 mmol) in DCM (3 mL) and stir at 60° C. for 1 hour. Cool to room temperature. Diluted with DCM (80 mL) and washed with saturated NH4Cl (3×30 mL). Combine organics, dry over anhydrous Na2SO4, and remove solvent under reduced pressure. Purify by silica gel chromatography, eluent 0-30% MeOH/EtOAc to afford title compound (0.53 g, 53%) as a white solid, after solvent removal from the chromatographic fractions. ES/MS (m/z): 317 (M+1). 1H NMR (399.80 MHz, CDCl3): 8.92 (s, 1H), 7.29 (m, 1H), 4.03 (s, 3H), 4.02 (s, 3H), 3.81 (t, J=6.2 Hz, 2H), 2.76 (s, 3H), 1.73-(m, 3H), 1.26 (m, 2H), 1.03 (m, 2H).

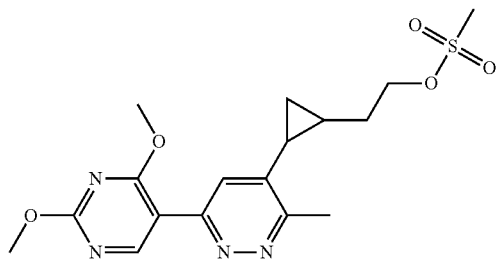 [SMILES: COc1ncc(-c2cc(C3CC3CCOS(C)(=O)=O)c(C)nn2)c(OC)n1]

Add methanesulfonyl chloride (0.2 mL, 3 mmol) to a solution of trans-2-[2-[6-(2,4-dimethoxypyrimidin-5-yl)-3-methyl-pyridazin-4-yl]cyclopropyl]ethanol (0.390 g, 1.22 mmol) and N,N-diisopropylethylamine (0.4 mL, 2 mmol) in DCM (8 mL) at 0° C. under N2. Stir at 0° C. for 40 minutes. Dilute with 50 mL of DCM and wash with 5% NaHCO3 (2×30 mL) and water (30 mL). Combine organics, dry over anhydrous Na2SO4, and evaporate solvent under reduced pressure. Purify by silica gel chromatography, eluent: 0-20% MeOH/EtOAc, to afford title compound as a brown solid (0.280 g, 58%), after solvent removal from the chromatographic fractions. ES/MS (m/z): 395 (M+1). 1H 1H NMR (399.80 MHz, CDCl3): 8.98 (s, 1H), 7.38 (s, 1H), 4.37 (t, J=6.2 Hz, 2H), 4.07 (s, 3H), 4.05 (s, 3H), 3.01 (s, 3H), 2.81 (s, 3H), 2.04 (m, 1H), 1.90-1.78 (m, 2H), 1.27 (m, 1H), 1.06 (t, J=7.1 Hz, 2H).

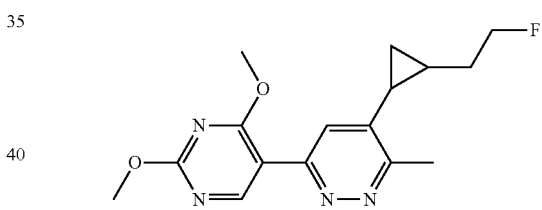

Add tetrabutylammonium fluoride hydrate (3 mL, 3 mmol, 1 M in THF) to a solution of trans-2-[2-[6-(2,4-dimethoxypyrimidin-5-yl)-3-methyl-pyridazin-4-yl]cyclopropyl]ethyl methanesulfonate (0.280 g, 0.71 mmol) in THF (3 mL) Heat at 70° C. for 2 hours. Cool to RT. Dilute with EtOAc, wash with saturated aqueous NaCl, dry over anhydrous Na2SO4, and remove solvent under reduced pressure. Purify by silica gel chromatography, eluent: 0-20% MeOH/EtOAc, to afford title compound as a pale yellow oil (0.170 g, 71%), after solvent removal from the chromatographic fractions. ES/MS (m/z): 319 (M+1). 1H NMR (399.80 MHz, CDCl3): 9.01 (m, 1H), 7.39 (s, 1H), 4.67-4.52 (dt, J H-F 48 Hz, J=6.7 Hz, 2H), 4.08 (s, 3H), 4.07 (s, 3H), 2.83 (s, 3H), 2.00-1.94 (m, 3H), 1.27 (m, 1H), 1.06 (m, 2H).

Chiral separation: column Lux Cellulose-4, 250×21 mm, flow rate 70 g/min, eluent: 40% MeOH/CO2.

Enantiomer 1>99% ee, rt 2.59 min (Lux Cellulose-4, 4.6×150 mm, 40% MeOH/CO2, 5 mL/min, 225 nm). Enantiomer 2>99% ee. rt 3.34 min (Lux Cellulose-4, 4.6×150 mm, 40% MeOH/CO2, 5 mL/min, 225 nm).

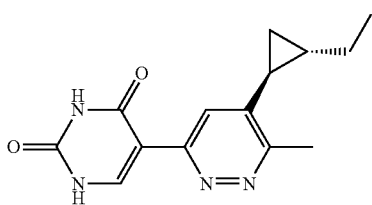 [SMILES: CC[C@H]1C[C@@H]1c1cc(-c2c[nH]c(=O)[nH]c2=O)nnc1C]

Dissolve 5-[5-[(-2-ethylcyclopropyl]-6-methyl-pyridazin-3-yl]-2,4-dimethoxy-pyrimidine isomer 1 (197 mg, 0.66 mmol) in a 1 M aqueous solution of HCl (4 mL) and heat the resulting mixture to 70° C. overnight. Cool the reaction mixture to RT, freeze in an acetone/dry ice bath at −78° C., and remove solvent by lyophilization to afford the title compound (0.176 g, 97%) as a pale yellow solid. ES/MS (m/z): 273 (M+H). $^1$H NMR (d$_6$-DMSO) δ: 1.00 (t, J=7.3 Hz, 3H), 1.11-1.16 (m, 1H), 1.27-1.33 (m, 2H), 1.47-1.52 (m, 2H), 1.92-1.96 (m, 1H), 2.80 (s, 3H), 8.00 (s, 1H), 8.41 (d, J=5.5 Hz, 1H), 11.73 (s, 1H), 11.99-11.91 (m, 1H).

Alternate Procedure for Examples 1-5

Stir a suspension of 5-[5-[(1S,2S)-2-ethylcyclopropyl]-6-methyl-pyridazin-3-yl]-2,4-dimethoxy-pyrimidine (16.2 g, 51.5 mmol) and 1 M aqueous solution of HCl (135 mL, 135 mmol) at 45° C. for 16 hours. Cool to RT, add a 2 M aqueous solution of K$_2$HPO$_4$ to pH~6 (approximately 150 mL), and stir at RT for 16 hours. Filter and collect the resulting solid, wash with water, and dry in vacuum oven at 45° C. for 16 hours to yield title compound (13.8 g, 93%) as a white solid. ES/MS (m/z): 273 (M+1). Crystallization of 5-[5-[(1S,2S)-2-Ethylcyclopropyl]-6-methyl-pyridazin-3-yl]-1H-pyrimidine-2,4-dione 5-[5-[(1S,2S)-2-Ethylcyclopropyl]-6-methyl-pyridazin-3-yl]-1H-pyrimidine-2,4-is dissolved in methanol, stirred at 50° C. for 1 hour and allowed to cool to ambient temperature where it crystallized from solution. The solids are isolated by vacuum filtration and briefly dried under vacuum at 70° C.

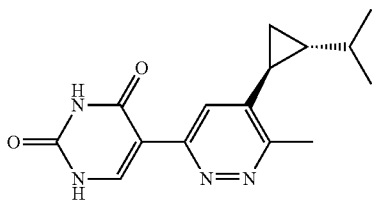 [SMILES: Cc1nnc(-c2c[nH]c(=O)[nH]c2=O)cc1[C@H]1C[C@@H]1C(C)C]

Dissolve trans-5-[5-[2-isopropylcyclopropyl]-6-methyl-pyridazin-3-yl]-2,4-dimethoxy-pyrimidine isomer 1 (628 mg, 2.00 mmol) in MeOH (3 mL). Add 1 M aqueous solution of HCl (5 mL) and heat to 70° C. for 3 hours. Cool to RT, load reaction mixture on MeOH-washed SCX column (20 g, Silicycle SILIABOND Tosic Acid), wash SCX column with MeOH (140 mL) and elute desired product with 2 M NH$_3$/MeOH (140 ml). Concentrate NH$_3$/MeOH fractions to obtain the title compound as a cream colored solid (546 mg, 95%). ES/MS (m/z): 287 (M+H). $^1$H NMR (d$_6$-DMSO) δ: 0.99 (m, 9H), 1.24 (m, 1H), 1.81 (m, 1H), 2.72 (s, 3H), 7.67 (s, 1H), 8.23 (s, 1H), 11.43 (bs, 2H).

Alternate Procedure for Examples 1-5

Stir a suspension of 5-[5-[(1S,2R)-2-isopropylcyclopropyl]-6-methyl-pyridazin-3-yl]-2,4-dimethoxy-pyrimidine (21.5 g, 65.6 mmol) and 1 M aqueous HCl solution (165 mL, 135 mmol) at 45° C. for 16 hours. Cool to RT and extract with MTBE. Discard the organic phase and add to the aqueous phase a 2 M aqueous solution of K$_2$HPO$_4$ until pH 6 (approximately 150 mL). Stir the resulting mixture at RT for 16 hours. Filter and collect the resulting solid, washing with water and drying in a vacuum oven at 45° C. for 16 hours to yield the title compound (14.3 g, 76%) as a white solid. ES/MS (m/z): 287 (M+1).

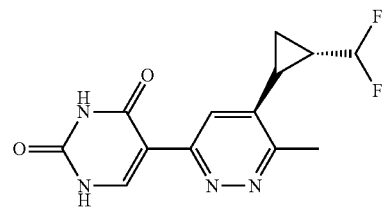

5-[5-[2-(Difluoromethyl)cyclopropyl]-6-methyl-pyridazin-3-yl]-1H-pyrimidine-2,4-dione may be prepared essentially as described in Example 1.

The following examples may be prepared essentially as described in Example 1.

| Example # | Chemical Name | Structure | ES/MS (m/z) (M + H) |
|---|---|---|---|
| 4 | 5-[6-Methyl-5-[rel-(1S,2S)-2-isobutylcyclopropyl]pyridazin-3-yl]-1H-pyrimidine-2,4-dione | 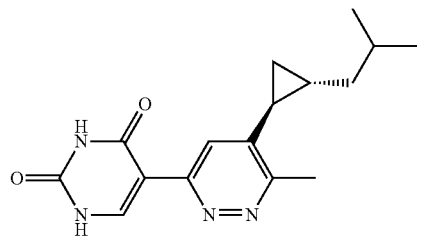 [SMILES: Cc1nnc(-c2c[nH]c(=O)[nH]c2=O)cc1[C@H]1C[C@@H]1CC(C)C] | 301 |

| Example # | Chemical Name | Structure | ES/MS (m/z) (M + H) |
|---|---|---|---|
| 5 | 5-[6-Methyl-5-[rel-(1S,2S)-2-(1,1-difluoroethyl)cyclopropyl]pyridazin-3-yl]-1H-pyrimidine-2,4-dione | 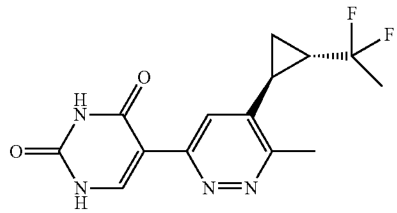 | 309 |
| 6 | 5-[5-[(1S,2S)-2-(Difluoromethyl)cyclopropyl]pyridazin-3-yl]-1H-pyrimidine-2,4-dione | 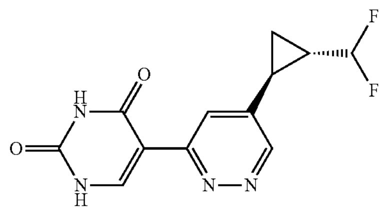 [SMILES: O=c1[nH]cc(-c2cc([C@H]3C[C@@H]3C(F)F)cnn2)c(=O)[nH]1] | 281 |

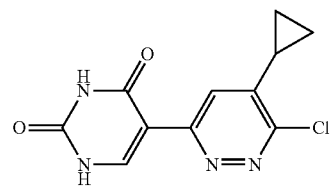 [SMILES: O=c1[nH]cc(-c2cc(C3CC3)c(Cl)nn2)c(=O)[nH]1]

Add 1 M HCl (14 mL, 14 mmol) to a solution of 3-chloro-4-cyclopropyl-6-(2,4-dimethoxypyrimidin-5-yl)pyridazine (1.0 g, 3.4 mmol) in MeOH (17 mL) and stir at 50° C. overnight. Remove solvent under reduce pressure to afford title compound (0.9 g, 100%) as a white solid. ES/MS (m/z): ($^{35}$Cl/$^{37}$Cl) 265/267

The following examples may be prepared essentially as described in Example 7.

| Example # | Chemical Name | Structure | ES/MS (m/z) ($^{35}$Cl/$^{37}$Cl) |
|---|---|---|---|
| 8 | 5-[6-Chloro-5-[rel-(1S,2R)-2-isopropylcyclopropyl]pyridazin-3-yl]-1H-pyrimidine-2,4-dione | 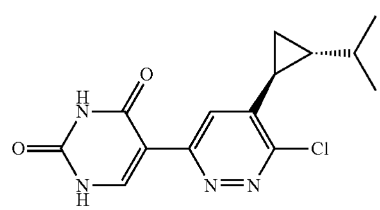 | 307/309 |
| 9 | 5-[6-Chloro-5-[rel-(1R)-2,2-difluorocyclopropyl]pyridazin-3-yl]-1H-pyrimidine-2,4-dione | 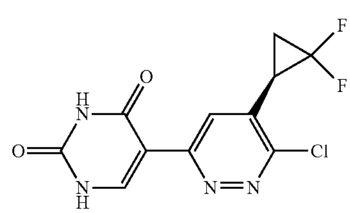 [SMILES: O=c1[nH]cc(-c2cc([C@H]3CC3(F)F)c(Cl)nn2)c(=O)[nH]1] | 301/303 |
| 10 | 5-[6-Chloro-5-[(1S,2S)-2-(difluoromethyl)cyclopropyl]pyridazin-3-yl]-1H-pyrimidine-2,4-dione | 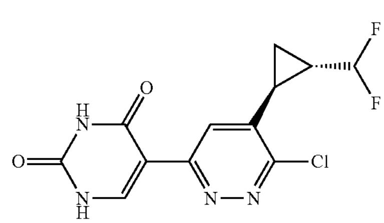 [SMILES: O=c1[nH]cc(-c2cc([C@H]3C[C@@H]3C(F)F)c(Cl)nn2)c(=O)[nH]1] | 315/317 |

| Example # | Chemical Name | Structure | ES/MS (m/z) ($^{35}$Cl/$^{37}$Cl) |
|---|---|---|---|
| 11 | 5-[6-Chloro-5-[rel-(1S,2S)-2-(1,1-difluoroethyl)cyclopropyl]pyridazin-3-yl]-1H-pyrimidine-2,4-dione | 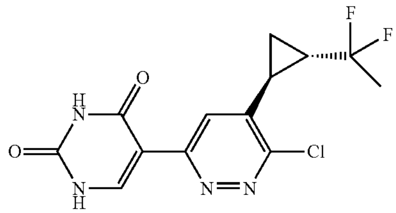 [SMILES: CC(F)(F)[C@H]1C[C@@H]1c1cc(-c2c[nH]c(=O)[nH]c2=O)nnc1Cl] | 329/331 |
| 12 | 5-(6-Chloro-5-cyclobutyl-pyridazin-3-yl)-1H-pyrimidine-2,4-dione;hydrochloride | 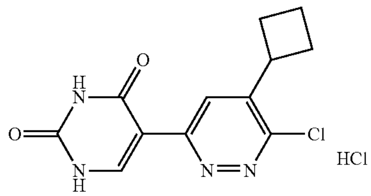 [SMILES: O=c1[nH]cc(-c2cc(C3CCC3)c(Cl)nn2)c(=O)[nH]1 ; Cl] | 279/281 |
| 13 | 5-[6-Chloro-5-(3,3-dimethylcyclobutyl)pyridazin-3-yl]-1H-pyrimidine-2,4-dione | 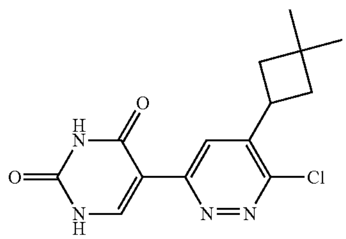 | 307/309 |
| 14 | 5-[6-Chloro-5-(3,3-difluorocyclobutyl)pyridazin-3-yl]-1H-pyrimidine-2,4-dione | 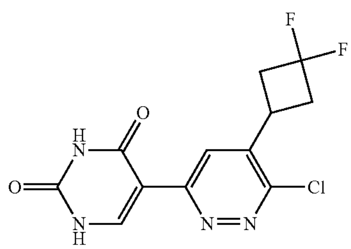 [SMILES: O=c1[nH]cc(-c2cc(C3CC(F)(F)C3)c(Cl)nn2)c(=O)[nH]1] | 315/317 |
| 15 | 5-(6-Chloro-5-cyclopentyl-pyridazin-3-yl)-1H-pyrimidine-2,4-dione | 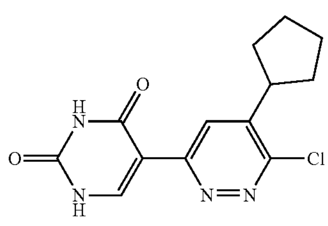 [SMILES: O=c1[nH]cc(-c2cc(C3CCCC3)c(Cl)nn2)c(=O)[nH]1] | 293/295 |

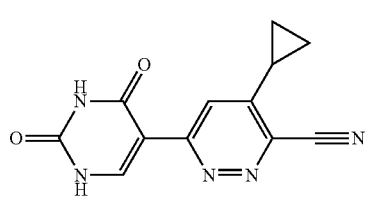 [SMILES: N#Cc1nnc(-c2c[nH]c(=O)[nH]c2=O)cc1C1CC1]

Degas a solution of 5-(6-chloro-5-cyclopropyl-pyridazin-3-yl)-1H-pyrimidine-2,4-dione (A, 57 mg, 0.22 mmol, 100 mass %) in DMF (1 mL, 12.9 mmol) with $N_2$. Add $Zn(CN)_2$ (20 mg, 0.22 mmol), tris(dibenzylideneacetone)dipalladium (0) (5 mg, 0.0054 mmol) and 1,1'-bis(diphenylphosphino)ferrocene (6 mg, 0.011 mmol) and degas further with $N_2$. Cap tightly and heat at 120° C. overnight. Cool to RT and filter through diatomaceous earth. Purify by revere phase chromatography (C18 Gold 15.5 g, gradient 5-20% ACN in 10 mM ammonium bicarbonate; 20 CV) to isolate title compound (0.032 g, 58%) as a pale yellow solid. ES/MS (m/z): 256 (M+1).

The following examples may be prepared essentially as described in Example 16.

| Example # | Chemical Name | Structure | ES/MS (m/z) (M + H) |
|---|---|---|---|
| 17 | 6-(2,4-Dioxo-1H-pyrimidin-5-yl)-4-[(1S,2R)-2-isopropylcyclopropyl]pyridazine-3-carbonitrile | 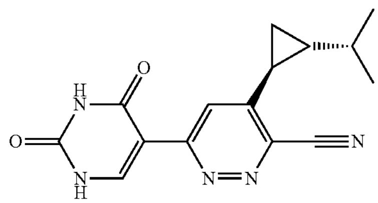 | 298 |
| 18 | 6-(2,4-Dioxo-1H-pyrimidin-5-yl)-4-[rel-(1S,2S)-2-(difluoromethyl)cyclopropyl]pyridazine-3-carbonitrile | 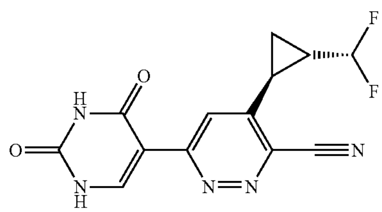 | 306 |
| 19 | 4-Cyclobutyl-6-(2,4-dioxo-1H-pyrimidin-5-yl)pyridazine-3-carbonitrile | 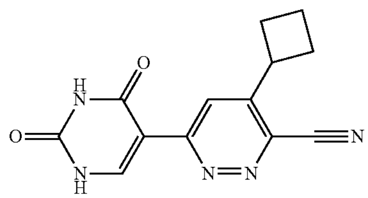 [SMILES: N#Cc1nnc(-c2c[nH]c(=O)[nH]c2=O)cc1C1CCC1] | 270 |
| 20 | 4-Cyclopentyl-6-(2,4-dioxo-1H-pyrimidin-5-yl)pyridazine-3-carbonitrile | 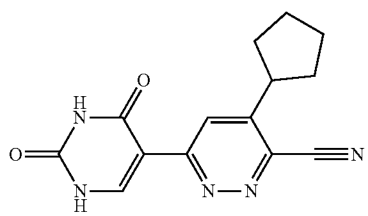 [SMILES: N#Cc1nnc(-c2c[nH]c(=O)[nH]c2=O)cc1C1CCCC1] | 284 |
| 21 | 4-[(1S)-2,2-Difluorocyclopropyl]-6-(2,4-dioxo-1H-pyrimidin-5-yl)pyridazine-3-carbonitrile | 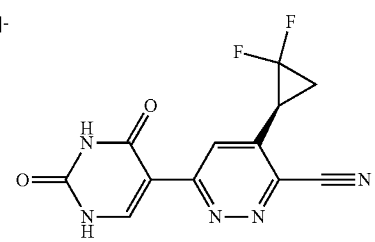 | 292 |
| 22 | 6-(2,4-Dioxo-1H-pyrimidin-5-yl)-4-[(1S,2S)-2-ethylcyclopropyl]pyridazine-3-carbonitrile | 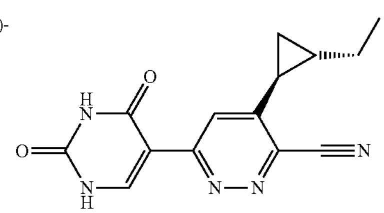 | 284 |

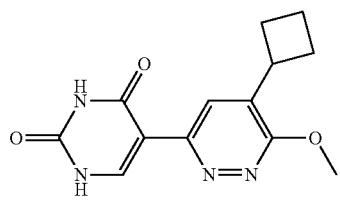 [SMILES: COc1nnc(-c2c[nH]c(=O)[nH]c2=O)cc1C1CCC1]

Add 1 M HCl (5.2 mL, 5.2 mmol) to 4-yclobutyl-6-(2,4-dimethoxypyrimidin-5-yl)-3-methoxy-pyridazine (0.39 g, 1.3 mmol) and stir at 50° C. for 6 hours then at RT overnight. Remove solvent under reduced pressure. Purify through SCX cartridge (10 g, eluents 60 mL DCM, 60 mL 50% MeOH in DCM and 120 mL of 50% 7 M NH$_3$ in MeOH in DCM) to afford title compound (0.337 g, 96%) as a white solid. ES/MS (m/z): 275 (M+1).

The following examples may be prepared essentially as described in Example 23.

| Example # | Chemical Name | Structure | ES/MS (m/z) (M + H) |
|---|---|---|---|
| 24 | 5-(5-Cyclopropyl-6-methoxy-pyridazin-3-yl)-1H-pyrimidine-2,4-dione | 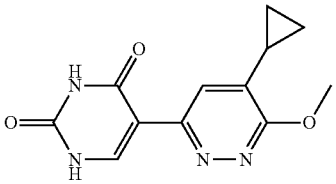 [SMILES: COc1nnc(-c2c[nH]c(=O)[nH]c2=O)cc1C1CC1] | 261 |
| 25 | 5-[5-(3,3-Dimethylcyclobutyl)-6-methoxy-pyridazin-3-yl]-1H-pyrimidine-2,4-dione | 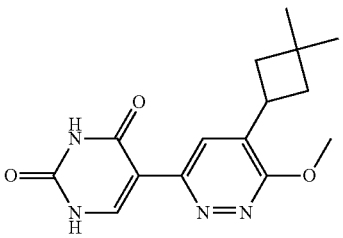 [SMILES: COc1nnc(-c2c[nH]c(=O)[nH]c2=O)cc1C1CC(C)(C)C1] | 303 |
| 26 | 5-[5-(3,3-Difluorocyclobutyl)-6-methoxy-pyridazin-3-yl]-1H-pyrimidine-2,4-dione | 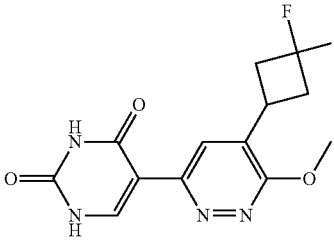 | 311 |
| 27 | 5-[5-(3,3-Difluorocyclopentyl)-6-methoxy-pyridazin-3-yl]-1H-pyrimidine-2,4-dione (Isomer 1) | 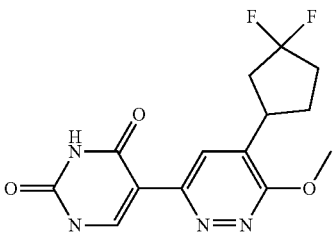 | 325 |
| 28 | 5-[5-(3,3-Difluorocyclopentyl)-6-methoxy-pyridazin-3-yl]-1H-pyrimidine-2,4-dione (Isomer 2) | 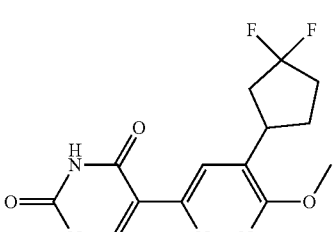 | 325 |
| 29 | 5-(5-Cyclohexyl-6-methoxy-pyridazin-3-yl)-1H-pyrimidine-2,4-dione | 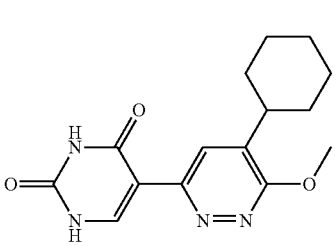 [SMILES: COc1nnc(-c2c[nH]c(=O)[nH]c2=O)cc1C1CCCCC1] | 303 |

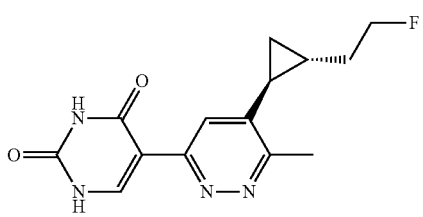 [SMILES: Cc1nnc(-c2c[nH]c(=O)[nH]c2=O)cc1[C@H]1C[C@@H]1CCF]

Add HCl (1 M in H₂O, 2 mL, 2 mmol) to Enantiomer 1 of trans 2,4-dimethoxy-5-[6-methyl-5-[2-(2-fluoroethyl)cyclopropyl]pyridazin-3-yl]pyrimidine (0.043 g, 0.14 mmol) and heat at 50° C. overnight. Remove solvent under reduced pressure. Purify through SCX cartridge (12 g, eluents 70 mL MeOH, 70 mL 2 M NH₃ in MeOH) to afford title compound (0.037 g, 89%) as a white solid ES/MS (m/z): 291 (M+1).

BIOLOGICAL ASSAYS

The following assays demonstrate that the exemplified compounds of the present invention are inhibitors of CD73 activity, and are useful in treating cancer.

CD73 Protein Expression and Purification

C-terminal 6-HIS-Tagged human CD73 (amino acids 1-547) is expressed in HEK293F mammalian cells by transiently transfected the cells with the CD73 gene and purified using Ni²⁺ affinity and Superdex 200 size exclusion chromatography. C-terminal 6-HIS-Tagged mouse CD73 (amino acids 1-549) is expressed and purified as described above. C-terminal 6-HIS-Tagged rat CD73 (amino acids 1-549) is expressed and purified as previously described.

Mass Spectroscopy for Adenosine and Adenosine Purification

An Agilent 300 RapidFire automated extraction system (Agilent, Santa Clara, Calif.) is used with three HPLC quaternary pumps, coupled to an Sciex 6500 triple quadrupole mass spectrometer (AB Sciex, Framingham, Mass.) with an electrospray ionization (ESI) interface source. Load a RapidFire Mass Spec system with reusable RapidFire HILIC (H1) solid-phase extraction (SPE) cartridge (G9203-80109).

Solvent A, used for sample loading and washing, is 50 mM ammonium formate, pH 4.0 containing 5% (v/v) ACN. Solvent B, used for sample elution, is 0.3% formic acid+2% ammonium hydroxide in 70% ACN/30% MeOH. Samples are sequentially analyzed by aspirating 10 μL onto the collection loop under vacuum directly from multiwell plates. Load 10 μL of sample is onto the HILIC cartridge and wash, by quaternary pump 1, using solvent A at a flow rate of 1.25 mL/minute for 3000 ms. The retained analytes elute to the mass spectrometer by quaternary pump 3, using solvent B at a flow rate of 1.25 mL/minute for 3000 ms. The system is re-equilibrated by quaternary pump 1, using solvent A at a flow rate of 1.25 mL/min for 3000 ms.

Equip the triple quadrupole mass spectrometer with an electrospray ionization (ESI) source and monitor analytes using selected reaction monitoring (SRM) in positive mode (M+H)+. Monitor adenosine at m/z 268.05/136.0 and adenosine monophosphate at m/z 348.1/136.0. Calculate area ratio values for adenosine and adenosine monophosphate using 13C5 Adenosine and 15N5 AMP as internal standards, respectively.

Human CD73 Biochemical Assay

The purpose of this assay is to identify and characterize inhibitors of CD73 enzyme activity. Add the reaction mixtures (20 μL) containing 2 μM adenosine monophosphate (Sigma #01930), 10 mM Tris pH 7.5, 100 mM NaCl, 0.01% BSA, 0.2 mM Octyl glucoside, and 50 pM CD73 protein to a 384 well plate (Nunc #264573). After 30 minutes incubation at RT, terminate the reaction by adding 20 μL stop solution containing 2% formic acid and 10 μM ¹³C5-adenosine (ribose labeled with ¹³C5) (Cambridge Isotope Laboratories—#CLM-3678-0) followed by addition of 40 μL dH₂O. Adenosine- and adenosine ribose-¹³C5 (internal standard) levels are determined utilizing mass spectrometry as described above. Use signal ratio (adenosine peak integration/adenosine internal standard peak integration) to quantitate each reaction. Calculate percent inhibition by using the equation {% inhibition=100×[1−(X−MIN)/(MAX−MIN)]} where X equals the well signal ratio, MAX equals median signal ratio of DMSO control and MIN equals signal ratio of enzyme activity in the presence of >10×IC₅₀ of a known competitive inhibitor. For screening purposes, test each compound at 50 μM in 1% DMSO. Determine IC₅₀ of each compound by testing each compound at 10 concentrations from 0.0025 to 50 μM (using a 1:3 dilution scheme).

The IC₅₀ for 5-[5-[(1S,2R)-2-isopropylcyclopropyl]-6-methyl-pyridazin-3-yl]-1H-pyrimidine-2,4-dione is 0.028 μM.

The IC₅₀ for 5-[5-[(1S,2S)-2-ethylcyclopropyl]-6-methyl-pyridazin-3-yl]-1H-pyrimidine-2,4-dione is 0.043 μM.

All of the compounds of the Examples disclosed herein exhibit an IC₅₀ of less than 0.062 μM.

Human CD73 Mechanism Assay

The purpose of this assay is to determine the mechanism of action of the compound of interest. The assay is carried out as indicated above for the Human CD73 Biochemical Assay. Each compound is tested at 8 different concentrations from 0.023 to 50 μM using a 1:3 dilution scheme, but at 8 different concentrations of AMP from 0.023 to 50 μM using a 3-fold dilution scheme. The area ratios for the varying inhibitor and substrate concentrations are plotted using GraphPad Prism 7.00 and fitted using dedicated mixed-model inhibition to determine Vmax, Km, Ki, and alpha values for inhibition {(Vmax$_{app}$=Vmax/(1+[I]/(Alpha*Ki)); Km$_{app}$=Km*(1+[I]/Ki)/(1+[I]/(Alpha*Ki)); Y=Vmax$_{app}$*X/(Km$_{app}$+X), where Alpha, Vmax, Km, and Ki are shared for each compound}.

Each of 5-[5-[(1S,2S)-2-ethylcyclopropyl]-6-methyl-pyridazin-3-yl]-1H-pyrimidine-2,4-dione and 5-[5-[(1S,2R)-2-isopropylcyclopropyl]-6-methyl-pyridazin-3-yl]-1H-pyrimidine-2,4-dione is an uncompetitive inhibitor that binds to the enzyme-phosphate complex, but not the apo-enzyme itself.

Increasing the substrate concentrations of AMP enhances the potency of uncompetitive inhibitors, for example, 5-[5-[(1S,2R)-2-isopropylcyclopropyl]-6-methyl-pyridazin-3-yl]-1H-pyrimidine-2,4-dionem, as its IC50 values is reduced, as shown in Table 1.

TABLE 1

| AMP (uM) | IC50 (uM) |
|---|---|
| 50.0 | 0.008327 |
| 16.7 | 0.006557 |

TABLE 1-continued

| AMP (uM) | IC50 (uM) |
|---|---|
| 5.6 | 0.008799 |
| 1.9 | 0.02028 |
| 0.61 | 0.06279 |
| 0.21 | 0.1513 |
| 0.069 | 0.2903 |
| 0.023 | 0.4094 |

Mouse CD73 Mechanism Assay

The purpose of this assay is to assess inhibitors with regard to their inhibition of mouse CD73 enzyme activity. This assay is carried out as described above for human CD73 biochemical assay, except that 3 μM AMP and 50 pM mouse CD73 enzyme are used.

The $IC_{50}$ for 5-[5-[(1S,2R)-2-isopropylcyclopropyl]-6-methyl-pyridazin-3-yl]-1H-pyrimidine-2,4-dione is 0.175 μM.

Calu6 Human Cell Assay

The purpose of this assay is to test compounds against CD73 in a cell-based assay. Calu6 cells (1500 cells/well) are grown in a 96 well Poly-D-Lysine coated plate (BD #356640) containing 100 μL of media (MEM (Gibco #11095-072)+1% Sodium Pyruvate (Gibco #11360-070)+1% NEAA (Gibco #11140-050)+10% FBS (Hyclone #SH30071). Plates are incubated at RT for 30 minutes, followed by incubation overnight at 37° C./5% $CO_2$. Cells are washed twice with assay buffer (10 mM Tris-HCl pH 7.2, 10 mM D-Glucose, 1 mM KCl, 125 mM NaCl, 2 mM $MgCl_2$)(90 μL/well). Then, 90 μL assay buffer is added to each well followed with addition of 10 μL per well of AMP and compound premix (50 μM AMP, varying concentrations of compound in 1% DMSO). Plates are incubated at room temperature for 60 minutes. Then, 10 μL supernatant per well is removed and added to a new plate followed by addition of 20 μL stop solution (2% formic acid, 1.2 μM Adenosine Ribose-$^{13}C5$ (Cambridge Isotope Laboratories—#CLM-3678-0) and 90 μL ddH2O for mass spectroscopy analysis. Adenosine- and Adenosine Ribose-$^{13}C5$ (internal standard) levels are determined by utilizing mass spectrometry (Agilent RapidFire) as described above for human CD73 biochemical assay. Percent inhibition is also calculated as described above.

The $IC_{50}$ for 5-[5-[(1S,2R)-2-isopropylcyclopropyl]-6-methyl-pyridazin-3-yl]-1H-pyrimidine-2,4-dione is 0.0073 uM (the compound of Example 2).

The $IC_{50}$ for 5-[5-[(1S,2S)-2-ethylcyclopropyl]-6-methyl-pyridazin-3-yl]-1H-pyrimidine-2,4-dione is 0.028 uM.

Ex Vivo Target Inhibition Assay

The purpose of this assay is to test compounds against murine CD73 in mouse blood in an ex vivo based assay. The animals (6/group) are dosed orally with each compound formulated in 20% HPBCD (2-hydroxypropyl-β-cyclodextrin), pH 2 after tumors reach to approximately 400 mm³. After treatment, blood is collected into heparin tubes and used for ex vivo analysis of conversion of $^{13}C10$-$^{15}N5$-AMP to labeled-adenosine, inosine, and hypoxanthine as described for ex vivo assay using whole blood collected from animals subjected to compound treatment via oral dosing.

5-[5-[(1S,2R)-2-isopropylcyclopropyl]-6-methyl-pyridazin-3-yl]-1H-pyrimidine-2,4-dione inhibits the conversion of AMP to adenosine, inosine, and hypoxanthine in mouse whole blood from animals treated with different doses of the compound, as shown in Table 2.

TABLE 2

| Inhibition of AMP conversion to adenosine | | |
|---|---|---|
| Group | Inhibition (%) | p-value |
| Vehicle | 0.0 | 1.000 |
| 1 mg/kg | −10.6 | 0.9139 |
| 2.5 mg/kg | 25.2 | 0.162 |
| 6.4 mg/kg | 37.0 | 0.0127* |
| 16 mg/kg | 56.5 | <0.0001* |
| 40 mg/kg | 88.6 | <0.0001* |
| 100 mg/kg | 94.3 | <0.0001* |

*statistical significance.

The $IC_{50}$ for 5-[5-[(1S,2R)-2-isopropylcyclopropyl]-6-methyl-pyridazin-3-yl]-1H-pyrimidine-2,4-dione is 0.0073 uM.

Calu6 Tumor Based In Vivo Target Inhibition of Human CD73 Assay

The purpose of this assay is to test compounds against human CD73 in xenograft tumors derived from human cancer Calu6 cells in an in vivo target inhibition assay. Calu6 cells (ATCC) are grown in HBSS medium supplemented with 10% fetal bovine serum. Harvest sub-confluent cells with trypsin and rinse twice with growth medium lacking serum. Initiate the growth of subcutaneous tumors by injecting 5×10⁶ in a 1:1 mixture of HBSS and MATRIGEL® (BD Biosciences, Franklin Lakes, N.J.) in the rear flank of nude mice (The Harlon Laboratory). When the mean tumor volume reaches approximately 400-500 mm³, randomize the animals by tumor size and body weight and place into their respective treatment groups as indicated. After treatment, tumor samples (50-80 mg each) are collected and processed in 1 mL of ice cold extraction buffer containing internal standards as described below.

A foil strip and liquid N2 are added to a the mortar to pre-chill. Tumor tissue is dropped onto the foil strip, and liquid N2 is added. Another foil strip is placed on top of the tumor tissue and is hammered with the pestle until the tumors are thoroughly grounded. 50 to 100 mg of tumor tissue is placed into tubes (Fishers Scientific, cat #02-681-302) and placed on dry ice. One metal bead (Qiagen Cat. No. 69989) and 1 ml of 80% of methanol containing the internal standards of $^{13}C_5$-Adenosine, $^{13}C_5$-AMP, $^{15}N_5$-GTP, $^{15}N_4$-inosine 5'-monophosphate, and $^{13}C$-$^{15}N$-Hypoxanthine (Cambridge Isotope Lab and Cayman Chemical) are added to the tubes, and samples are stored at −80° C. until use for LC/MS analysis.

Blood is also collected into heparin tubes and used for ex vivo analysis of conversion of $^{13}C_5$-$^{15}N5$-AMP to labeled-adenosine, inosine, and hypoxanthine as described for ex vivo assay using whole blood collected from animals subjected to compound treatment via oral dosing.

As shown in Table 3, 5-[5-[(1S,2R)-2-isopropylcyclopropyl]-6-methyl-pyridazin-3-yl]-1H-pyrimidine-2,4-dione inhibits the conversion of AMP to adenosine in Calu6 tumors treated with different doses of the compound.

TABLE 3

Inhibition of AMP conversion to adenosine

| Compound Treatment Group (mg/kg) | Inhibition (%) | p-value |
|---|---|---|
| 0.0 | 0 | 1.000 |
| 1.0 | 39.1 | 0.0057* |
| 2.5 | 68.5 | <0.0001* |
| 6.4 | 64.3 | <0.0001* |
| 16.0 | 77.5 | <0.0001* |
| 40.0 | 82.1 | <0.0001* |
| 100.0 | 89.3 | <0.0001* |

*statistical significance.

T Cell Suppression Assay

Carboxyfluorescein diacetate succinimidyl ester (CFSE) is used as a labeling agent Human PBMCs or isolated CD4 cells ($0.5 \times 10^6$-$1 \times 10^8$ cell) are washed with a labeling buffer (RPMI 1640 w/L-glutamine, GIBCO cat #11875) containing 5% HI FBS (Gibco #10082), and suspended in 1 ml of the labeling buffer. Cells are mixed with 110 µl PBS containing 50 µM CFSE (Biolegend cat #423801), and incubated at room temperature for 5 min. Labeled cells are washed once with PBS containing 5% HI FBS (Gibco #10082) and once with T cell normal growth media (X-Vivo 15, Lonza, cat #04-744Q) containing 1× penicillin/streptomycin), and suspended in growth media used for PMBCs and CD4 cells.

T Cell Activation and Treatment

CFSE labeled human PBMCs (600,000 cells/mL) or CD4 cells (500,000 cells/mL) are mixed with Dynabeads® Human T-Activator CD3/CD28 (Gibco, cat #11131D) at a ratio of 1:1 of cell/beads and human IL-2 (60 IU/ml, Roche, cat #: 11011456001). Cells are placed in a 37° C. water bath for 10 min to pre-activate T cells. PBMCs (125 µl/well) or CD4 cells (100 µl/well) are transferred to a 96 well plate (Costar 3799, Corning Inc.). To test compounds using PBMCs, test compounds at various concentrations are prepared in cell normal growth media (125 µL) containing 400-600 µM AMP. To test compounds using CD4 cells, test compounds at various concentrations are prepared in cell normal growth media (100 µL) containing 200-250 µM AMP. Treated cells are cultured at 37° C., 5% $CO_2$ for 68-70 hr.

Medium (160 µl) containing treated PBMCs is transferred to a plate and the remaining medium used for cytokine assay is transferred to AcroPrep 96 plates (AcroPrep 96 Filter plate, Omega 3K NTRL 350 ul well, Pall Life Science Cat #8033) for preparation of samples for LC-MS analysis of metabolites.

Medium (100 µl) containing CD4 cells is transferred to and filtered through AcroPrep plates to another plate via centrifugation at 1500 g for 2 hr. Filtered medium (50 µl/well) is mixed with the same volume of 80% methanol, 1% $NH_4OH$, and internal standards (250 ng/mL $^{13}C_5$-AMP and 250 ng/mL $^{13}C_5$-Adenosine) for LC-MS analysis of metabolites.

Treated PBMCs or CD4 cells are collected and stained for Flow Cytometry to quantify T cell proliferation.

Flow Cytometry

PBMCs or CD4 cells are stained with Zombie Aqua (Biolegend, cat #423102, Lot #B195875) at 1:200 dilution in DPBS for 15 min and followed by blocking with Human Fc Receptor Binding Inhibitor (eBioscience Cat #No. 14-9161-73) at 1:5 dilution for 15 min in flow staining buffer (DPBS-2% HIFBS-0.5% BSA) on ice. PBMCs are stained with a cocktail of APC/Cy7 anti human CD3 (Biolegend cat #300426, 1:20 dilution), APC antihuman CD4 (Biolegend, Cat #317416, 1:20 dilution), and Pacific Blue anti-human CD8a (Biolegend, Cat #300927, 1:20 dilution), and CD4 cells are stained with APC anti-human CD4 (Biolegend, Cat #317416, 1:20 dilution) in flow staining buffer for 30 min on ice.

Flow data are acquired by BD FACS Verse. Each fluorescence channel is appropriately compensated. The data are processed on FloJo ver. 7.6.5 with the following gating strategy: lymphocytes gated on FSC vs SSC dot plot; viable cells of lymphocytes gated on SSC vs Zombie Aqua dot plot; CD3 cells of viable lymphocytes gated on APC-Cy7 vs Zombie Aqua dot plot1; CD4 cell and CD8 cells of CD3 cells gated on APC vs Pacific Blue dot plot; CD4 and CD8 cells further gated on APC vs CFSE(FITC) and Pacific Blue vs CFSE(FITC) dot plots. Proliferation of CD4 and CD8 cells is analyzed by a proliferation tool. Proliferation Index (PI) is defined as total cell number/starting cell number, and compound rescue % is calculated as $(PI_{w/o\ AMP\ w/o\ cpd} - PI_{sample})/(PI_{w/o\ AMP\ w/o\ cpd} - PI_{w\ AMP\ w/o\ cpd})*100$.

As shown in Table 4, inhibition of CD73 by 5-[5-[(1S, 2R)-2-isopropylcyclopropyl]-6-methyl-pyridazin-3-yl]-1H-pyrimidine-2,4-dione rescues the adenosine-mediated inhibition of T cell proliferation, which is correlated with a dose dependent reduction in adenosine levels in the growth medium.

TABLE 4

Rescue of adenosine-mediated inhibition of T cell proliferation

| Compound (uM) | Rescue of T cell proliferation (%) | Adenosine (uM) |
|---|---|---|
| 5.00 | 107 | 0.017 |
| 1.66667 | 106 | 0.027 |
| 0.55556 | 104 | 0.046 |
| 0.18519 | 95 | 0.086 |
| 0.06173 | 37 | 0.15 |
| 0.02058 | −2 | 0.21 |
| 0.00686 | −3 | 0.28 |
| 0.00229 | −6 | 0.28 |
| 0.00 | 0 | 0.30 |

Cytokine Analysis

Culture medium from treated PBMCs is diluted at 1:7.5, 1:2.5 and 1:50 with 1× ELISA/ELISPOT Diluent from cytokine ELISA kits and analyzed for TNFα using Human TNF alpha ELISA Ready-SET-GO! Kit (eBioscience cat #88-7346-22), IL-1β using Human IL-1β ELISA ready-SET-GO! Kit ($2^{nd}$ generation) (eBioscience, cat #88-7261-22) and IFNγ using Human IFN gamma ELISA ready-SET-GO! Kit (eBioscience, cat #88-7316-22) based manufacturer's manuals.

As shown in Table 5, inhibition of CD73 by 5-[5-[(1S, 2R)-2-isopropylcyclopropyl]-6-methyl-pyridazin-3-yl]-1H-pyrimidine-2,4-dione increases TNF-α levels in CD4+ T cells.

TABLE 5

TNF-α release

| Compound (uM) | TNF-α (pg/mL) |
|---|---|
| 6.000 | 1985.5 |
| 2.000 | 1183.9 |
| 0.667 | 1618.1 |
| 0.222 | 1265.5 |
| 0.074 | 782.0 |
| 0.025 | 557.8 |
| 0.008 | 419.9 |

TABLE 5-continued

TNF-α release

| Compound (uM) | TNF-α (pg/mL) |
|---|---|
| 0.003 | 386.3 |
| 0.000 | 357.0 |

As shown in Table 6, inhibition of CD73 by 5-[5-[(1S,2R)-2-isopropylcyclopropyl]-6-methyl-pyridazin-3-yl]-1H-pyrimidine-2,4-dione increases TNF-α levels in CD4+ T cells.

TABLE 6

INF-γ release

| Compound (uM) | INF-γ (pg/mL) |
|---|---|
| 6.000 | 105.3 |
| 2.000 | 99.5 |
| 0.667 | 147.8 |
| 0.222 | 146.7 |
| 0.074 | 59.4 |
| 0.025 | 51.1 |
| 0.008 | 29.5 |
| 0.003 | 34.5 |
| 0.000 | 9.0 |

In Vivo Models

If desired, pre-clinical modeling of the CD73-inhibitory effect of a compound of the present invention, or a pharmaceutically acceptable salt thereof, can be performed, for example, according to methods set forth in the art, for example, in Rongvaux A, et al., *Annual Rev. Immunology* 2013; 31: 635-74, and in literature cited therein; Sanmamed M F, et al., *Annals of Oncology* 2016; 27: 1190-1198, and in literature cited therein.

LC/MS Based Assay for Measuring CD73 Activity in Human Serum

Fresh normal human blood is centrifuged at 1,500 g for 15 minutes at room temperature, and the upper fraction containing serum is collected. Serum (25 ul/well) collected is transferred to a 96-deep well plate (DWP, Analytical Sales & Services Inc. Cat #968820) containing various concentrations of the compound of Example 2 and a fixed concentration of levamisole (1,500 uM). After incubation on ice for 60 min, $^{13}C5$-$^{15}N5$-AMP (50 uM) is added to each well in the plate, and the plate is incubated at room temperature for 15 min. The plate is then placed on dry ice with addition of 200 uL/well of 17.3 TCA followed by shaking at 26 fps for 3 min with a plate-shaking machine (Qiagen). The plate is then centrifuged at 2940 g for 20 min at 4° C. After centrifugation, 100 ul/well of supernatant from each well is transferred to a new 96 deep well plate and mixed with 18.4 ul/well of 2.5M $Na_2CO_3$ on ice followed by addition of 200 ul of extraction solution containing internal standard (IS: $^{13}C5$-AMP, $^{13}C5$-adenosine, $^{13}C5$-hypoxanthine, and $^{15}N4$-inosine). After further centrifugation at 2940 g for 20 min at 4° C., 200 ul/well of the supernatant is used for analysis of $^{13}C10$-$^{15}N5$-adenosine, $^{13}C10$-$^{15}N5$-inosine and $^{15}N5$-hypoxanthine by LC/MS as described above. For EC50 calculations, the concentrations of the CD73 inhibitor in the serum are corrected with the fraction unbound (%) derived from in silico models or experimentally.

Table 7 contains data for inhibition of CD73 activity in human serum by 5-[5-[(1S,2R)-2-isopropylcyclopropyl]-6-methyl-pyridazin-3-yl]-1H-pyrimidine-2,4-dione (the compound of Example 2).

TABLE 7

| Compound of Example 2 (uM) | Inhibition (%) |
|---|---|
| 4.6800 | 76.9 |
| 1.5600 | 71.1 |
| 0.5200 | 56.8 |
| 0.1733 | 39.6 |
| 0.0578 | 25.4 |
| 0.0193 | 15.4 |
| 0.0064 | 8.4 |
| 0.0021 | 3.7 |
| 0.0007 | 0.7 |
| 0 | 0.0 |

Table 8 contains data for inhibition of CD73 activity in human serum by certain compounds disclosed herein.

TABLE 8

| Example | EC50 (uM) |
|---|---|
| 1 | 0.1 |
| 2 | 0.213 |
| 3 | 0.051 |
| 8 | 0.179 |
| 9 | 0.297 |
| 10 | 0.055 |
| 22 | 0.212 |

We claim:

1. A compound of the formula:

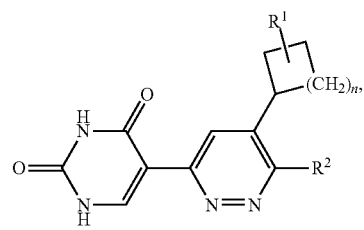

wherein n is 0-3;

$R^1$ is —H, —F, -gem-difluoro, -gem-dimethyl, —$C_{1-4}$ alkyl, —$CHF_2$, —$CF_2CH_3$ or —$CH_2CH_2F$; and $R^2$ is selected from —H, —$CH_3$, —F, —Cl, —CN, or —$OCH_3$;

or a pharmaceutically acceptable salt thereof.

2. The compound according to claim 1, which is:

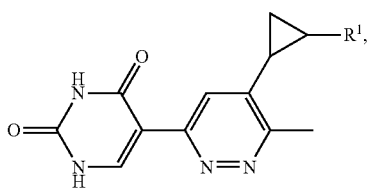

or a pharmaceutically acceptable salt thereof.

3. The compound according to claim 2, which is:

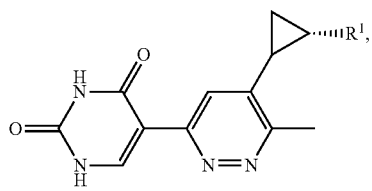

or a pharmaceutically acceptable salt thereof.

4. The compound according to claim 2, which is:

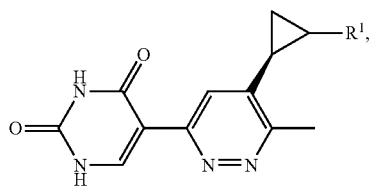

or a pharmaceutically acceptable salt thereof.

5. The compound according to claim 4, which is:

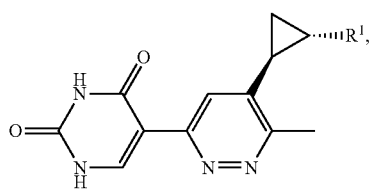

or a pharmaceutically acceptable salt thereof.

6. The compound according to claim 1,
wherein n is 0, $R^1$ is —$C_{1-4}$ alkyl, and $R^2$ is —$CH_3$,
or a pharmaceutically acceptable salt thereof.

7. The compound according to claim 6, wherein $R^1$ is isopropyl, or a pharmaceutically acceptable salt thereof.

8. The compound according to claim 1, which is

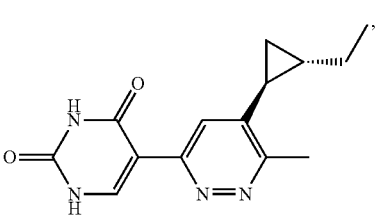

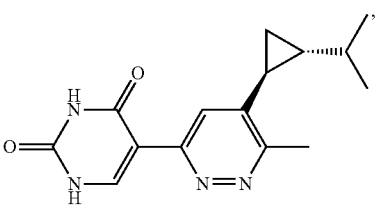

-continued

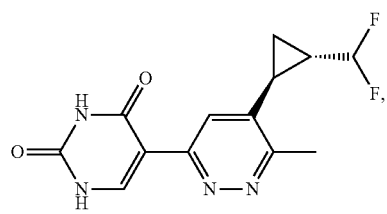

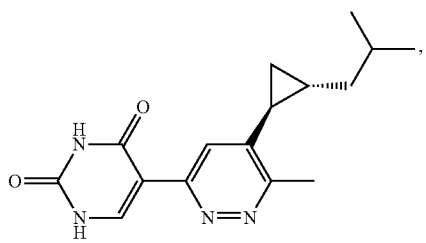

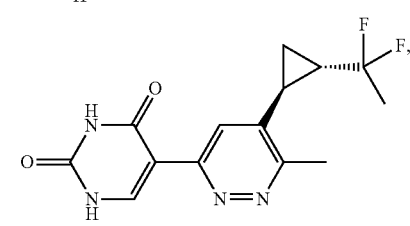

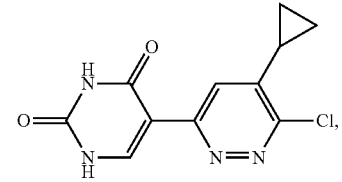

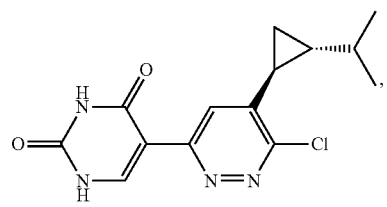

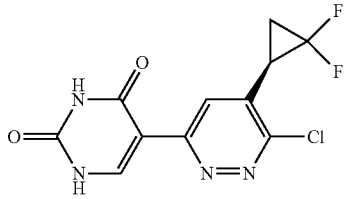

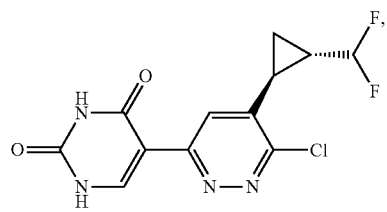

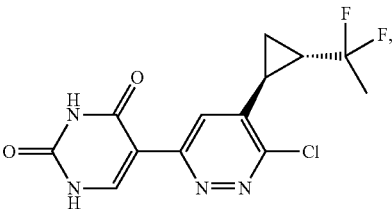

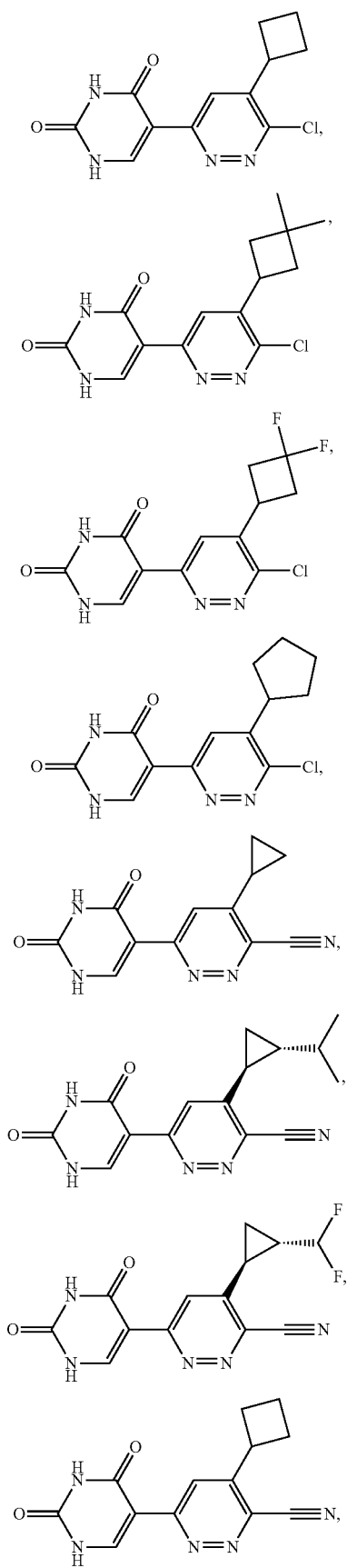
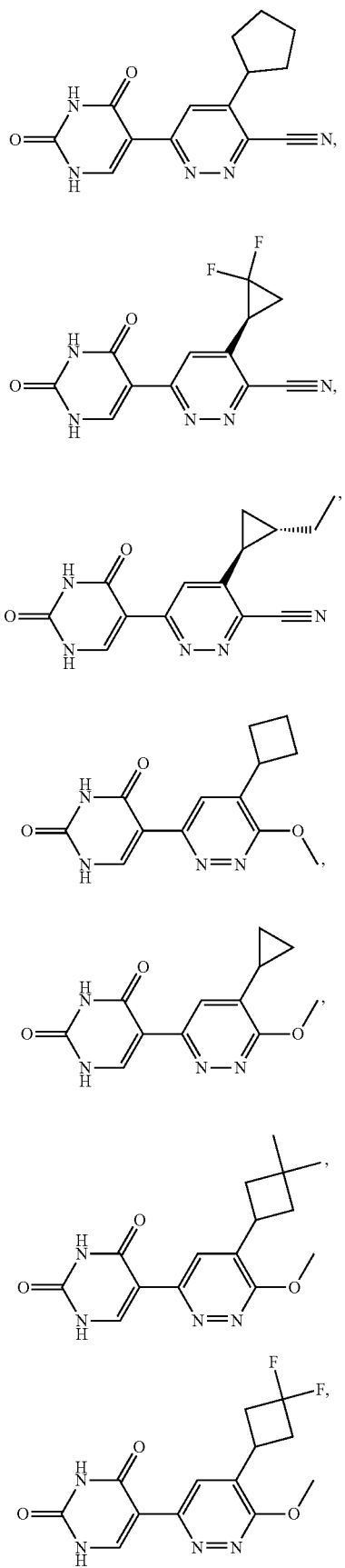

-continued

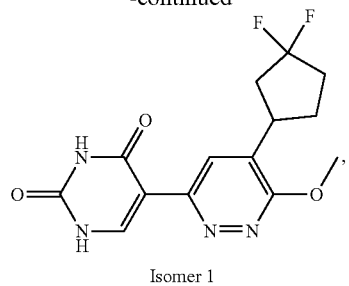

Isomer 1

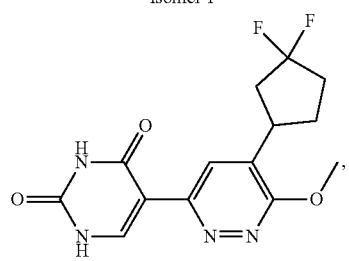

Isomer 2

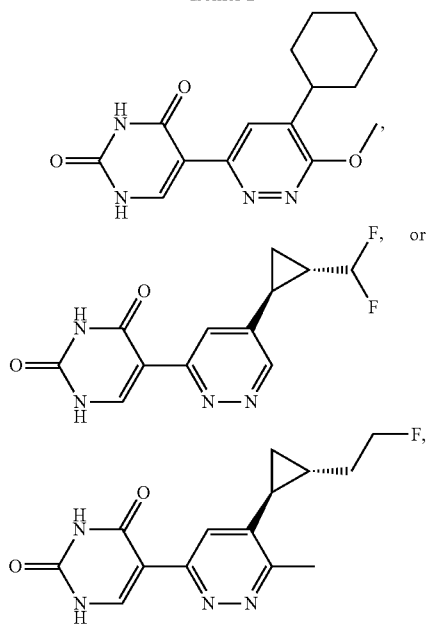

or a pharmaceutically acceptable salt thereof.

9. The compound according to claim 2, which is:

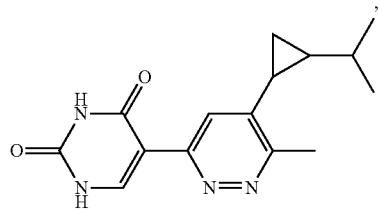 [SMILES: Cc1nnc(-c2c[nH]c(=O)[nH]c2=O)cc1C1CC1C(C)C]

or a pharmaceutically acceptable salt thereof.

10. The compound according to claim 9, which is 5-[5-[(1S,2R)-2-isopropylcyclopropyl]-6-methyl-pyridazin-3-yl]-1H-pyrimidine-2,4-dione, or a pharmaceutically acceptable salt thereof.

11. The compound according to claim 2, which is:

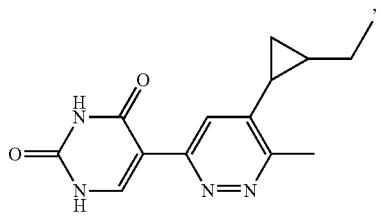 [SMILES: CCC1CC1c1cc(-c2c[nH]c(=O)[nH]c2=O)nnc1C]

or a pharmaceutically acceptable salt thereof.

12. The compound according to claim 11, which is 5-[5-[(1S,2S)-2-ethylcyclopropyl]-6-methyl-pyridazin-3-yl]-1H-pyrimidine-2,4-dione, or a pharmaceutically acceptable salt thereof.

13. A pharmaceutical composition comprising a compound of the formula:

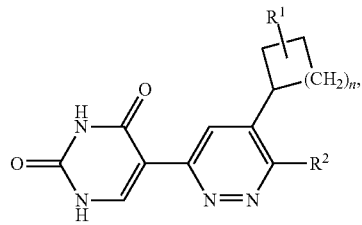

wherein n is 0-3;
$R^1$ is —H, —F, -gem-difluoro, -gem-dimethyl, —$C_{1-4}$ alkyl, —$CHF_2$, —$CF_2CH_3$ or —$CH_2CH_2F$; and
$R^2$ is selected from —H, —$CH_3$, —F, —Cl, —CN, or —$OCH_3$;
or a pharmaceutically acceptable salt thereof, and one or more pharmaceutically acceptable carriers, diluents, or excipients.

14. A method of treating cancer, comprising administering to a patient in need thereof, an effective amount of a compound of the formula:

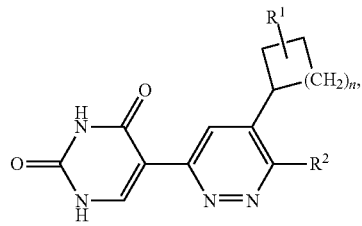

wherein n is 0-3;
$R^1$ is —H, —F, -gem-difluoro, -gem-dimethyl, —$C_{1-4}$ alkyl, —$CHF_2$, —$CF_2CH_3$ or —$CH_2CH_2F$; and
$R^2$ is selected from —H, —$CH_3$, —F, —Cl, —CN, or —$OCH_3$;
or a pharmaceutically acceptable salt thereof,
wherein the cancer is bladder cancer, breast cancer, cholangiocarcinoma, colorectal cancer, colon cancer, gastric cancer, gallbladder cancer, glioblastoma, head and neck cancer, liver cancer, lung cancer, lymphoma, medulloblastoma, melanoma, ovarian cancer, pancreatic cancer, prostate cancer or renal cancer.

15. The method of claim 14, wherein the patient is one in whom serum CD73 activity has been determined.

16. The method of claim 14, wherein the patient is one in whom tissue CD73 expression has been determined.

17. A method, comprising determining CD73 activity in the serum of a patient to whom a compound of the formula:

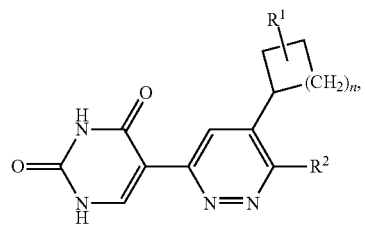

wherein n is 0-3;
R¹ is —H, —F, -gem-difluoro, -gem-dimethyl, —C$_{1-4}$ alkyl, —CHF$_2$, —CF$_2$CH$_3$ or —CH$_2$CH$_2$F; and
R² is selected from —H, —CH$_3$, —F, —Cl, —CN, or —OCH$_3$;
or a pharmaceutically acceptable salt thereof, has been administered.

18. A method, comprising determining CD73 expression in tissue from a patient to whom a compound of the formula:

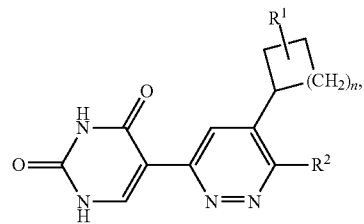

wherein n is 0-3;
R¹ is —H, —F, -gem-difluoro, -gem-dimethyl, —C$_{1-4}$ alkyl, —CHF$_2$, —CF$_2$CH$_3$ or —CH$_2$CH$_2$F; and
R² is selected from —H, —CH$_3$, —F, —Cl, —CN, or —OCH$_3$;
or a pharmaceutically acceptable salt thereof, has been administered.

19. The pharmaceutical composition according to claim 13, wherein the compound is:

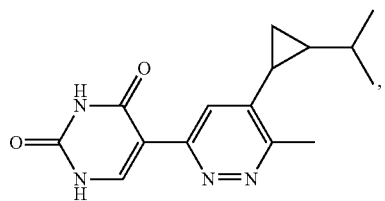 [SMILES: Cc1nnc(-c2c[nH]c(=O)[nH]c2=O)cc1C1CC1C(C)C]

or a pharmaceutically acceptable salt thereof.

20. The pharmaceutical composition according to claim 19, wherein the compound is 5-[5-[(1S,2R)-2-isopropylcyclopropyl]-6-methyl-pyridazin-3-yl]-1H-pyrimidine-2,4-dione, or a pharmaceutically acceptable salt thereof.

21. The method according to claim 14, wherein the compound is:

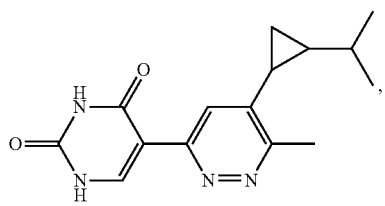 [SMILES: Cc1nnc(-c2c[nH]c(=O)[nH]c2=O)cc1C1CC1C(C)C]

or a pharmaceutically acceptable salt thereof.

22. The method according to claim 21, wherein the compound is 5-[5-[(1S,2R)-2-isopropylcyclopropyl]-6-methyl-pyridazin-3-yl]-1H-pyrimidine-2,4-dione, or a pharmaceutically acceptable salt thereof.

* * * * *